(12) United States Patent
Martin

(10) Patent No.: US 11,609,242 B1
(45) Date of Patent: Mar. 21, 2023

(54) EFFICIENT GAIT DATA MANAGEMENT IN MOBILE

(71) Applicant: David Martin, San Francisco, CA (US)

(72) Inventor: David Martin, San Francisco, CA (US)

( * ) Notice: Subject to any disclaimer, the term of this patent is extended or adjusted under 35 U.S.C. 154(b) by 482 days.

(21) Appl. No.: 16/806,773

(22) Filed: Mar. 2, 2020

Related U.S. Application Data

(63) Continuation-in-part of application No. 16/505,629, filed on Jul. 8, 2019, which is a continuation-in-part of application No. 16/275,323, filed on Feb. 14, 2019, now Pat. No. 10,973,440, application No. 16/806,773, which is a continuation-in-part of application No. 16/275,323, filed on Feb. 14, 2019, now Pat. No. 10,973,440, and a continuation-in-part of application No. 16/044,833, filed on Jul. 25, 2018, said application No. 16/505,629 is a continuation-in-part of application No. 16/044,833, filed on Jul. 25, 2018, application No. 16/806,773, which is a continuation-in-part of application No. 15/706,651, filed on Sep. 15, 2017, now Pat. No. 11,045,116, and a continuation-in-part of application No. 15/296,868, filed on Oct. 18, 2016, now Pat. No. 10,488,222, which is a continuation-in-part of application No. 14/932,591, filed on Nov. 4, 2015, now abandoned, said application No. 16/505,629 is a continuation-in-part of application No. 14/922,174, filed on Oct. 25, 2015, now Pat. No. 10,342,462.

(60) Provisional application No. 62/750,292, filed on Oct. 25, 2018, provisional application No. 62/702,998, filed on Jul. 25, 2018, provisional application No. 62/654,536, filed on Apr. 9, 2018, provisional application No. 62/651,409, filed on Apr. 2, 2018, provisional application No. 62/249,371, filed on Nov. 2, 2015, provisional application No. 62/090,698, filed on Dec. 11, 2014, provisional application No. 62/068,685, filed on Oct. 26, 2014.

(51) Int. Cl.
*G01P 13/00* (2006.01)
*G01P 15/18* (2013.01)
*A61B 5/11* (2006.01)

(52) U.S. Cl.
CPC ............... *G01P 13/00* (2013.01); *G01P 15/18* (2013.01); *A61B 5/112* (2013.01); *A61B 5/1118* (2013.01)

(58) Field of Classification Search
CPC ........ G01P 13/00; G01P 15/18; A61B 5/1118; A61B 5/112
See application file for complete search history.

(56) References Cited

U.S. PATENT DOCUMENTS

| | | | | |
|---|---|---|---|---|
| 2009/0124938 A1* | 5/2009 | Brunner | ............... | A61B 5/1038 600/595 |
| 2011/0009241 A1* | 1/2011 | Lane | ...................... | G06F 3/011 482/8 |
| 2014/0288679 A1* | 9/2014 | McNamee | ............ | A63F 13/211 700/91 |
| 2015/0018013 A1* | 1/2015 | Martin | .................. | H04W 4/027 455/456.3 |
| 2017/0188897 A1* | 7/2017 | Thein | .................... | A61B 5/1118 |

\* cited by examiner

*Primary Examiner* — Steven O Douglas

(57) ABSTRACT

Methods are described for generating a user interface displaying at least a useful image, wherein the useful image has been created in some embodiments by means of: determining, over a period of time, a first set of a first amount of values of a gait attribute, and obtaining, using the first set and leveraging a matrix factorization, a second set of a second amount of values representing colors.

20 Claims, 20 Drawing Sheets

FIG. 12 (Upper detail with highest resolution for FIG. 11)

FIG. 13 (Lower details with highest resolution for FIG. 11)

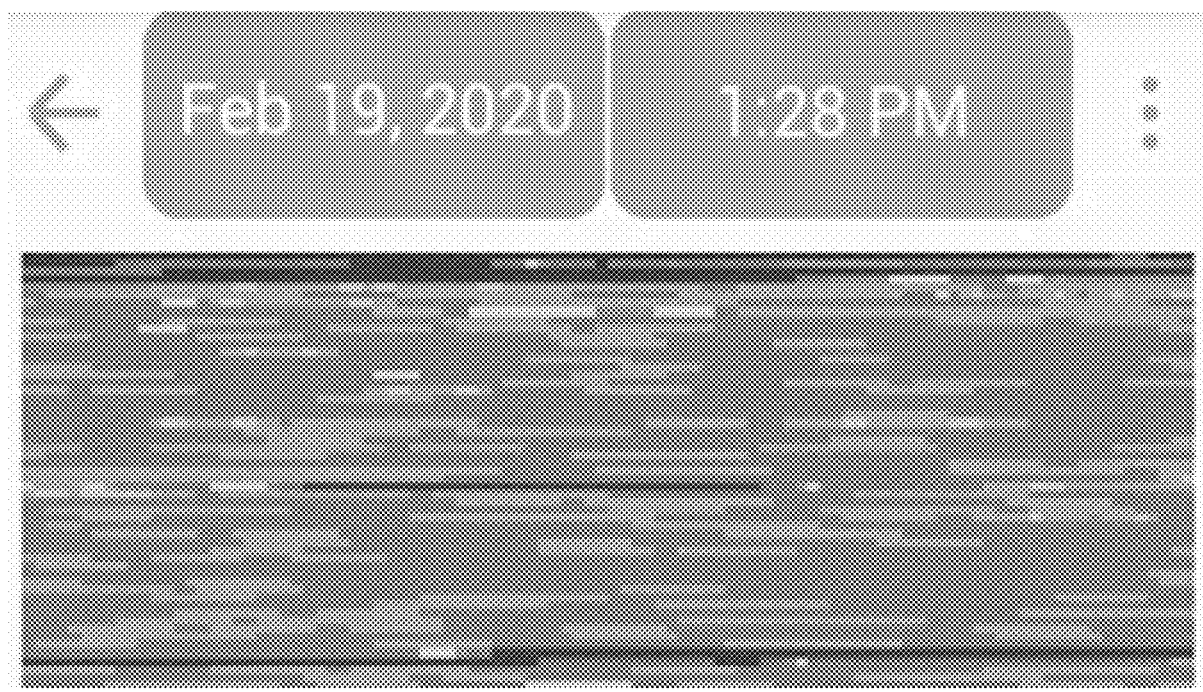
FIG. 14A (Upper details with highest resolution for FIG. 14)

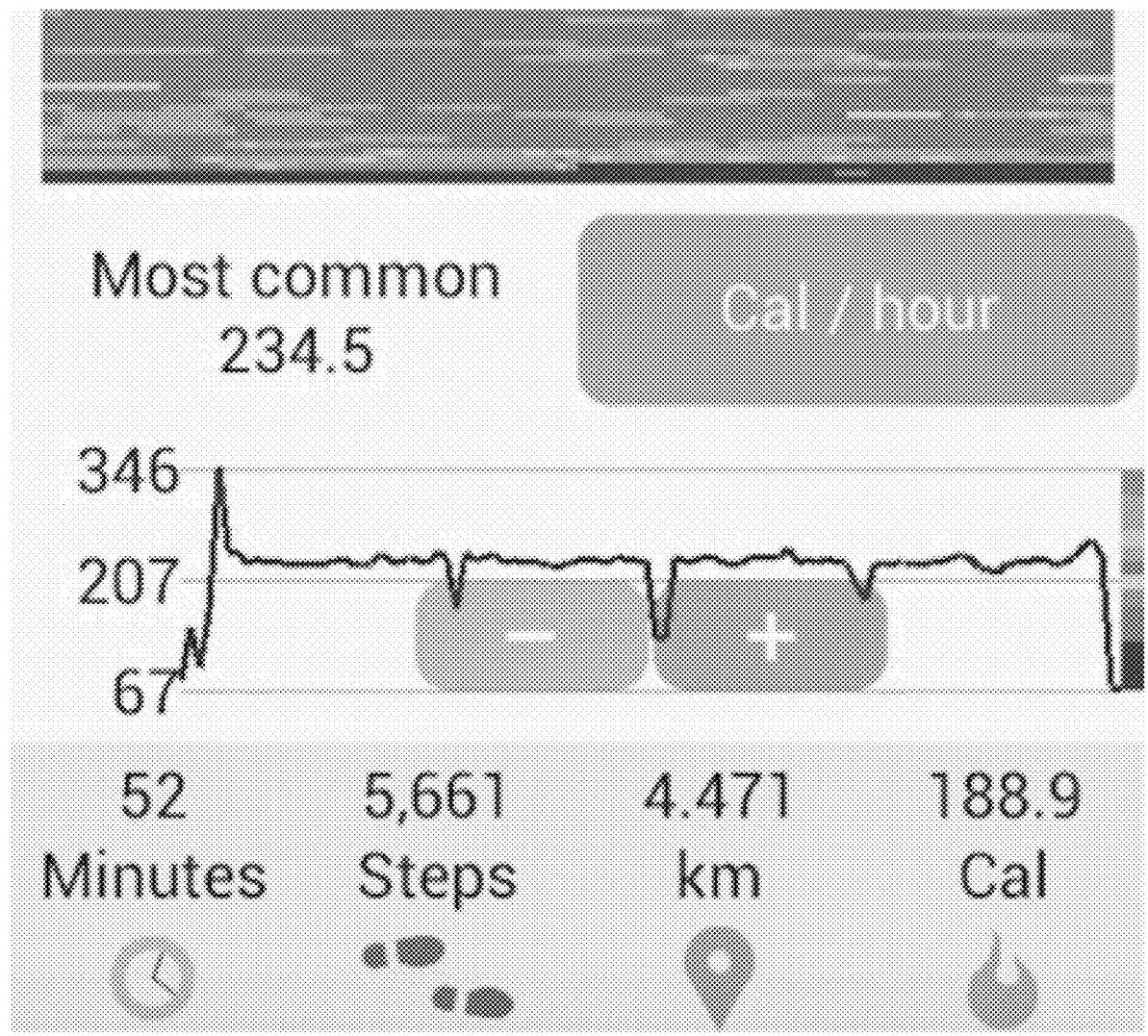
FIG. 14B (Lower details with highest resolution for FIG. 14)

EFFICIENT GAIT DATA MANAGEMENT IN MOBILE

CROSS REFERENCE TO RELATED APPLICATIONS

This application is a continuation-in-part of U.S. application Ser. No. 16/505,629, by David Martin, entitled "Mobile control using gait cadence", filed Jul. 8, 2019, which:
a. claims the benefits of at least the following: U.S. provisional patent application No. 62/702,998, by David Martin, entitled "Leveraging mobility features for precise control", filed Jul. 25, 2018, and U.S. provisional patent application No. 62/750,292, by David Martin, entitled "Gait analysis applied for control", filed Oct. 25, 2018.
b. is a continuation-in-part of U.S. application Ser. No. 14/922,174 (now patent), by David Martin, entitled "Application of Gait Characteristics for Mobile", filed Oct. 25, 2015, which claims the benefits of U.S. provisional patent application No. 62/068,685, by David Martin, entitled "Application of Gait Characteristics for Mobile", filed Oct. 26, 2014.
c. is also a continuation-in-part of U.S. application Ser. No. 14/932,591, by David Martin, entitled "Enhanced Real Time Frailty Assessment for Mobile", filed Nov. 4, 2015, which claims the benefits of U.S. provisional patent application No. 62/090,698, by David Martin, entitled "Enhanced Real Time Frailty Assessment for Mobile", filed Dec. 11, 2014.
d. is also a continuation-in-part of U.S. application Ser. No. 15/296,868 (now patent), by David Martin, entitled "Mobile device control leveraging user kinematics", filed Oct. 18, 2016, which claims the benefits of U.S. provisional patent application No. 62/249,371, by David Martin, entitled "Mobile device control leveraging user kinematics", filed Nov. 2, 2015.
e. is also a continuation-in-part of U.S. application Ser. No. 16/044,833, by David Martin, entitled "Refined Control Leveraging Mobile Characteristics for health care", filed Jul. 25, 2018, which claims the benefits of at least U.S. provisional patent application No. 62/068,685, by David Martin, entitled "Application of Gait Characteristics for Mobile", filed Oct. 26, 2014.
f. is also a continuation-in-part of U.S. application Ser. No. 16/275,323, by David Martin, entitled "Mobile control using gait velocity", filed Feb. 14, 2019, which claims the benefits of at least U.S. provisional patent applications Nos. 62/651,409, 62/654,536, 62/702,998, and 62/750,292 by David Martin.

This application is also a continuation-in-part of U.S. application Ser. No. 16/275,323, by David Martin, entitled "Mobile control using gait velocity", filed Feb. 14, 2019, which claims the benefits of at least:
a. U.S. provisional patent application No. 62/651,409, by David Martin, entitled "Control Strategies For Mobile Using Gait Analysis", filed Apr. 2, 2018, and U.S. provisional patent application No. 62/654,536, by David Martin, entitled "Control For Health Care In Mobile Leveraging Gait Analysis", filed Apr. 9, 2018, and U.S. provisional patent application No. 62/702,998, by David Martin, entitled "Leveraging mobility features for precise control", filed Jul. 25, 2018, and U.S. provisional patent application No. 62/750,292, by David Martin, entitled "Gait analysis applied for control", filed Oct. 25, 2018.

This application is also a continuation-in-part of U.S. application Ser. No. 16/044,833, by David Martin, entitled "Refined Control Leveraging Mobile Characteristics for health care", filed Jul. 25, 2018, which claims the benefits of at least U.S. provisional patent application No. 62/068,685, by David Martin, entitled "Application of Gait Characteristics for Mobile", filed Oct. 26, 2014.

This application is also a continuation-in-part of U.S. application Ser. No. 15/706,651, by David Martin, entitled "Enhanced determination of cadence for control in mobile", filed Sep. 15, 2017.

All of these applications are hereby incorporated by reference in their entireties for all purposes.

BACKGROUND

Field

This application relates to mobile and wearable devices, specifically to methodologies to efficiently manage large amounts of data related to the user's gait.

BACKGROUND

Discussion of Related Art

Common methods to obtain cadence by means of sensors embedded within mobile or wearable devices make use of thresholds, and detect steps when the value of a sensor signal reaches said thresholds. In order to achieve an accuracy improvement, the use of adaptable thresholds has also been proposed. Nevertheless, most of those approaches focus their analysis on the time domain, and although some methods make use of frequency analysis (e.g. using FFT to obtain the fundamental frequency of the signal), their algorithms still rely on thresholding in the time domain, making them prone to errors, especially with weak or noisy motion signals typical of walking. Recent studies with commercially available devices show large errors in the determination of the user's cadence, and those errors increase as the walking velocity decreases. In fact, considerable inaccuracies at low speeds may have important implications in health care applications. Consequently, there is a need for an enhanced methodology to accurately determine the cadence and other gait attributes (e.g. velocity, stride length, calories burned per time unit, activity) of mobile or wearable device users, and enable a new field of applications not possible with existing methodology. Among those applications, the control of a representation of the device user on the device screen, leveraging gait attributes.

Sensors in mobile or wearable devices provide an opportunity to monitor user's data (including gait data, activity data, fitness data, health data, etc.). Existing methods and/or applications (e.g. fitness applications for mobile devices such as smartphones) generally display aggregate data for the user to have only a global look at his/her activities. For example, it is common practice among mobile applications in the fitness and/or health art, to display the total amount of steps taken by the user over a whole day, or display only a few bars indicating the total number of steps taken by the user during each one of the 24 hours of a day. Other gait attributes such as calories burned, speed, distance, etc. are treated similarly by existing mobile applications, in such a way that the user can only see data with a very low resolution or granularity (typically time intervals of 1 day or 1 hour). This very low resolution in the data presented to the user is a problem for many technical fields and for many potential new applications. For example, many users would like to see the variation of their data (e.g. a gait attribute such as speed, calories burned per hour, cadence, stride or step length, etc.) with a high resolution.

BRIEF DESCRIPTION OF THE DRAWINGS

FIGS. 14A and 14B provide higher details of the same.

DETAILED DESCRIPTION OF EMBODIMENTS OF THE INVENTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Some inventive functionality and inventive principles may be implemented with or in software programs or instructions and integrated circuits (ICs) such as application specific ICs. In the interest of brevity and minimization of any risk of obscuring the principles and concepts according to the present invention, discussion of such software and ICs, if any, is limited to the essentials with respect to the principles and concepts within some of the embodiments.

Figure 1A:
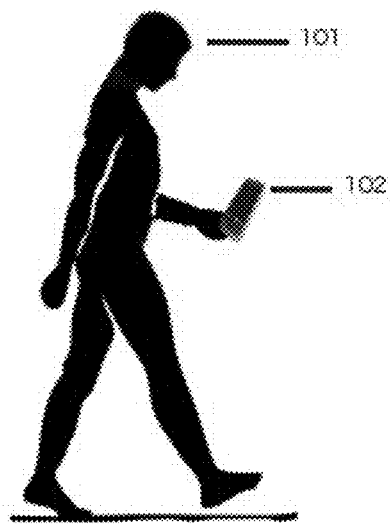
FIG. 1A represents an example of mobile device user walking with the device.
Figure 1B:
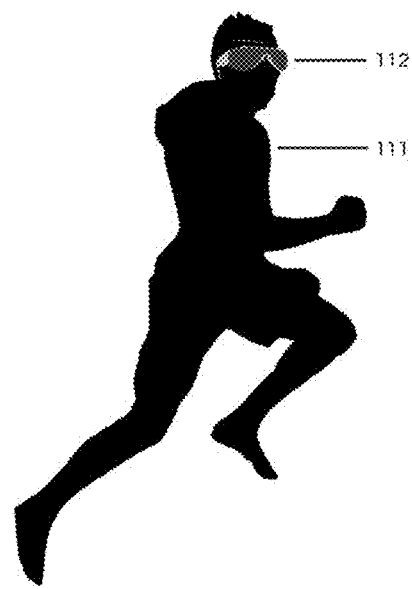
FIG. 1B represents an example of wearable device user running with the device.

FIG. 1A represents an individual, (101), walking with a mobile device, (102). In some embodiments, individual (101) may be performing any kind of walking, jogging, running, sprinting, or any other type of gait activity (including household activities. This Figure and its elements (510), (520), (530), (540), (550), (560), (570), and (580) are further described in U.S. application Ser. No. 14/922,174, by David Martin, entitled "Application of Gait Characteristics for Mobile", filed Oct. 25, 2015, and U.S. application Ser. No. 16/044,833, by David Martin, entitled "Refined Control Leveraging Mobile Characteristics for Health Care", filed Jul. 25, 2018, which are hereby incorporated by reference for all purposes. FIG. 1B represents an example of one embodiment in which individual (111) is running while wearing a device in the form of glasses (112). In some embodiments (112) may represent any type of virtual reality device, eyewear, glasses or any other type of wearable or mobile device that individual (111) is wearing in any way attached or positioned on his/her face, head, or any other place of his/her body. This Figure and its elements are further described in application Ser. Nos. 14/922,174 and 16/044,833.

Figure 1C:
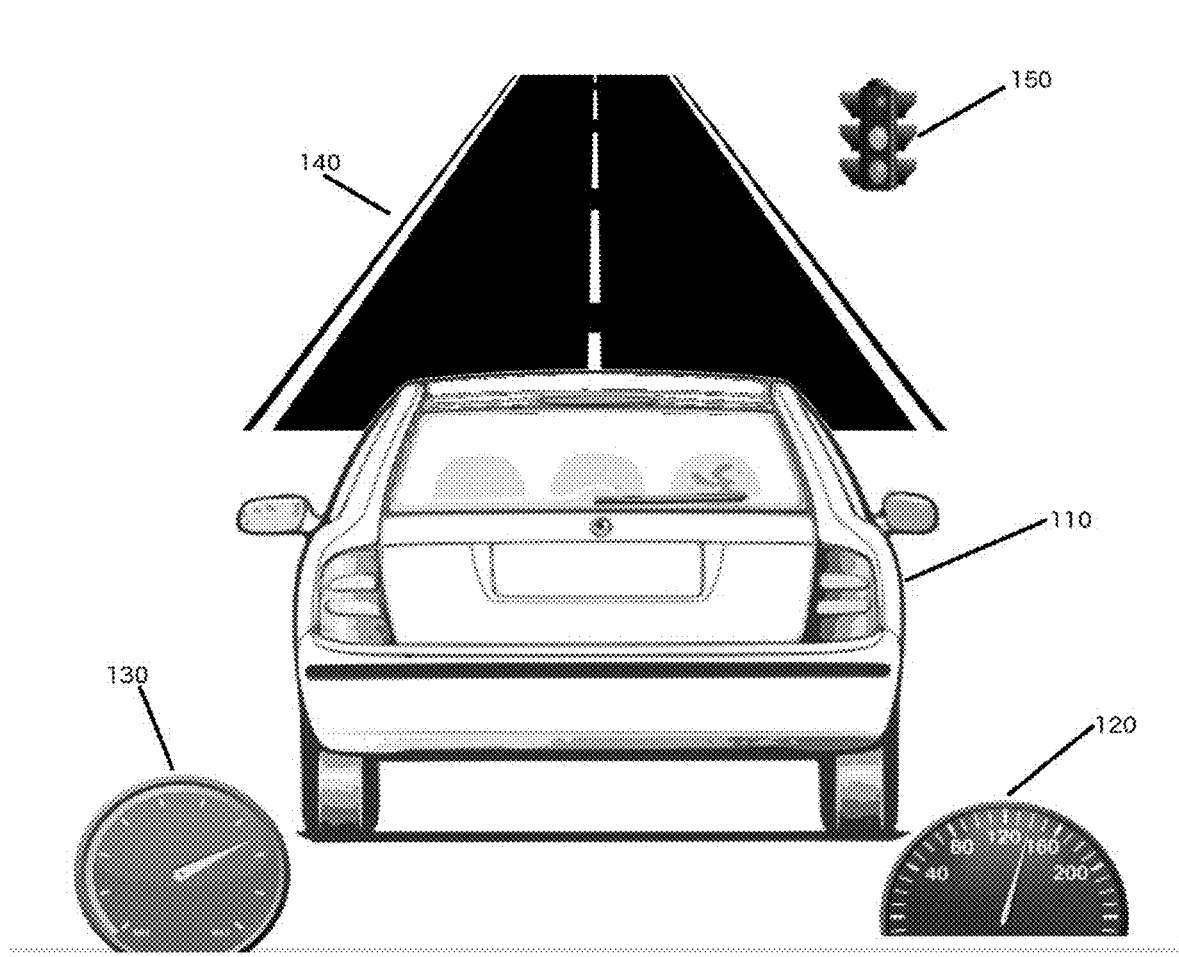
FIG. 1C illustrates an example of virtual environment displayed on the mobile or wearable device according to one embodiment.

In some embodiments, FIG. 1C may illustrate an example of screenshot of the display of devices (102) or (112), representing a virtual environment with which the individual (101) or (111) may interact. By way of example, and not limitation, the display may show a car (110) moving along a road (140) with some elements such as traffic lights (150). Moreover, the display may also show some dashboard elements such as (120) or (130) to indicate certain magnitudes, variables or metrics of any kind. This Figure and its elements are further described in application Ser. Nos. 14/922,174 and 16/044,833.

Figure 2A:
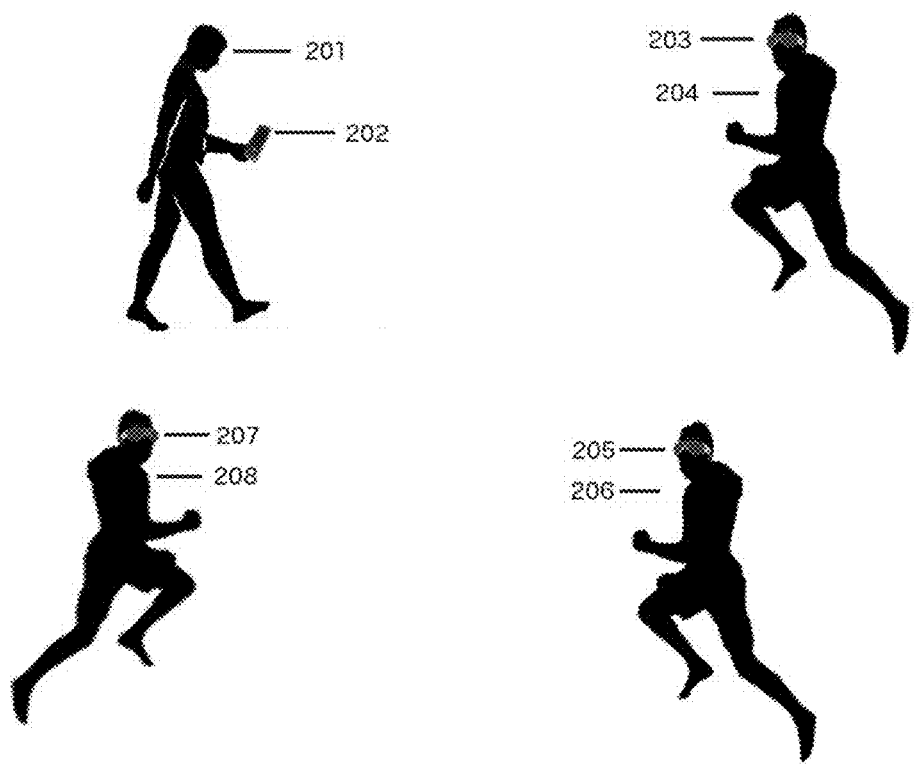
FIG. 2A represents an example of mobile and/or wearable device users performing some gait activity with their devices in a networking environment.

FIG. 2A represents an example of an embodiment in which four individuals (201), (204), (206), (208) participate in a networking environment; in this particular embodiment, each individual has one device: individual (201) is walking and has device (202), which may represent a smartphone, phablet, tablet, or any other type of device. Individual (204) is running and has device (203). In a similar way, individuals (206) and (208) are running and wearing their own devices (205) and (207) respectively. This Figure and its elements are further described in application Ser. Nos. 14/922,174 and 16/044,833.

Figure 2B:
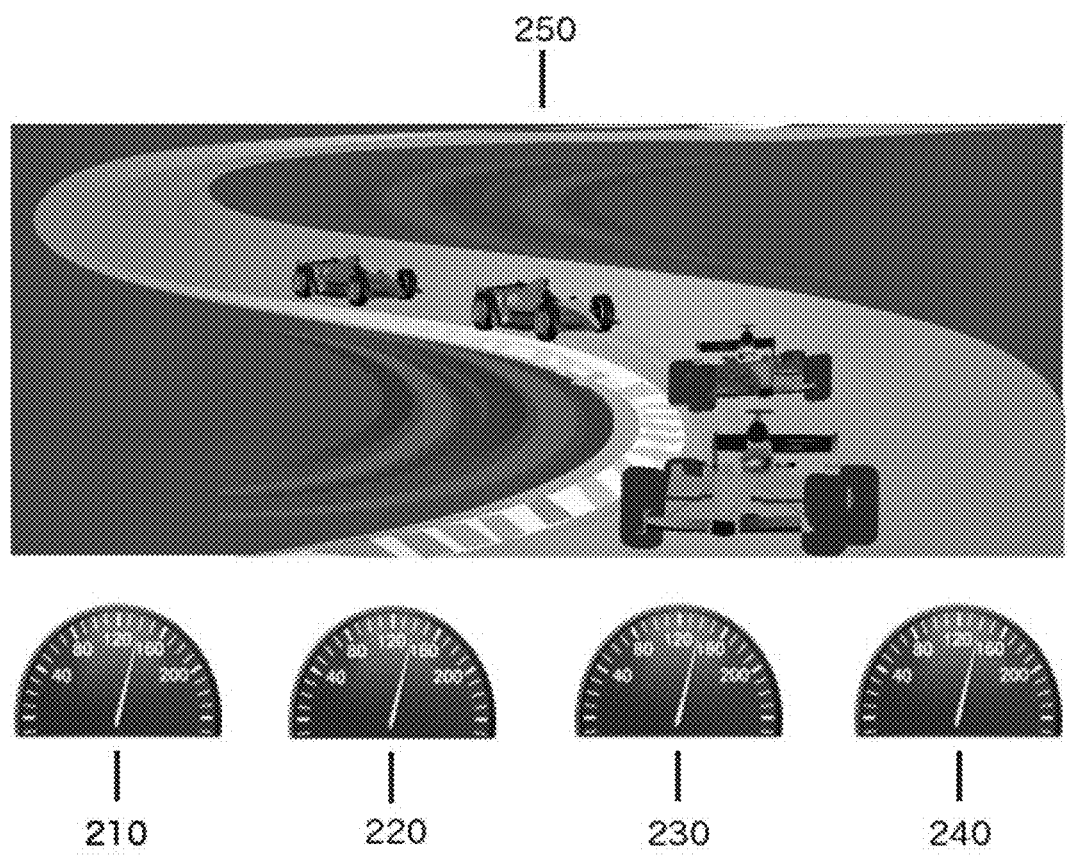
FIG. 2B illustrates an example of virtual environment displayed on the mobile and/or wearable devices in a networking environment according to one embodiment.

FIG. 2B represents an example of an embodiment illustrating an example of screenshot of the display of any or all of the devices (202), (203), (207) or (205). In a particular embodiment corresponding to a networking environment such as the one represented in FIG. 2A, FIG. 2B may represent an example of screenshot seen by individuals (201), (204), (206) and (208) in the display of any or all of their devices. This Figure and its elements (210), (220), (230), (240), and (250) are further described in application Ser. Nos. 14/922,174 and 16/044,833.

Figure 3:
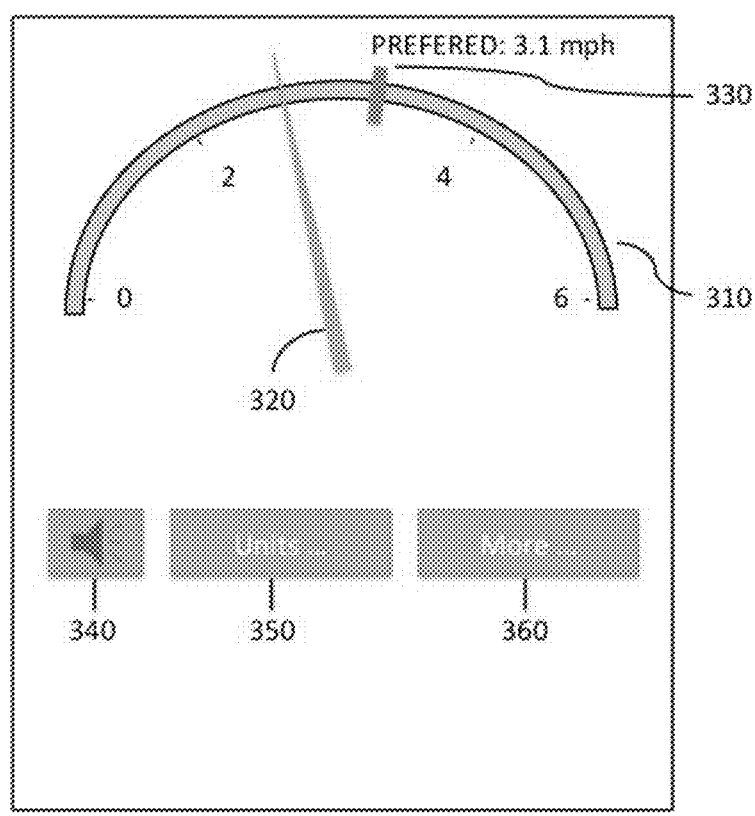
FIG. 3 shows an example of an embodiment of the presentation of contextual information on a mobile and/or wearable device.

In some embodiments, any contextual information may be displayed directly on the user's device display. By way of example and not limitation, the velocity of the user may be displayed in real time (typically, fractions of a second) on the mobile device display as shown in FIG. 3, which illustrates an example of the many possibilities. This Figure and its elements (310), (320), (330), (340), (350), and (360) are further described in application Ser. No. 14/922,174.

Figure 4:
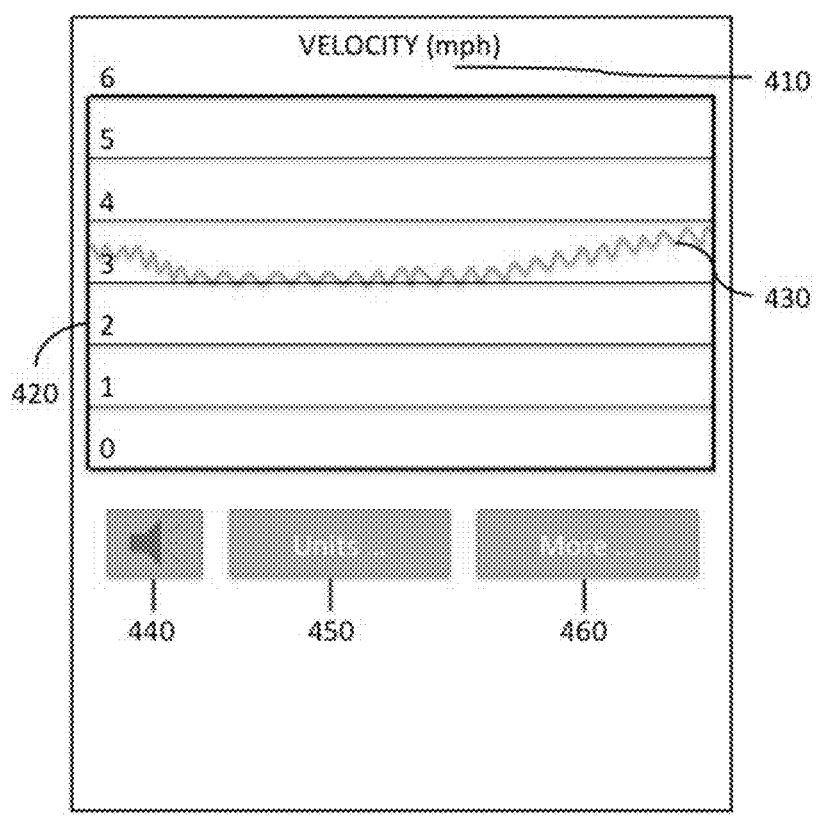
FIG. 4 shows an example of another embodiment of the presentation of contextual information on a mobile and/or wearable device.

FIG. 4 represents an embodiment of a representation of the user's velocity; in other embodiments, any other contextual information and/or gait characteristic or attribute (e.g. stride length, cadence, calories burned, etc. and combinations thereof) or related information may be represented. This Figure and its elements (410), (420), (430), (440), (450), and (460) are further described in application Ser. Nos. 14/922,174 and 16/044,833.

Figure 5A:
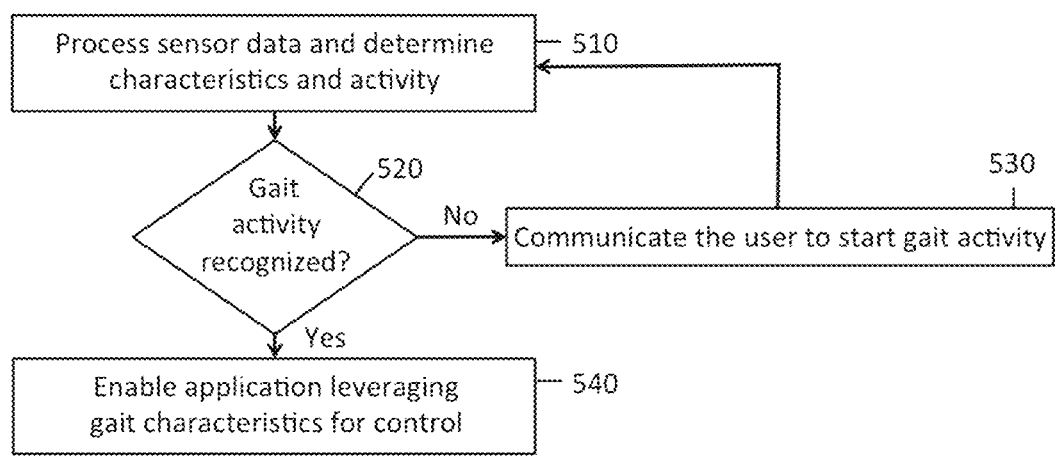
FIG. 5A presents a process flow diagram of an embodiment enabling and controlling an application with the user's gait characteristics.

FIG. 5A represents a flow diagram of possible basic steps of some embodiments enabling and controlling an application with the user's gait characteristics (including cadence, stride length, velocity, calories burned per time unit, activity, device position and/or any other and/or any variations and/or combinations thereof). This Figure and its elements (510), (520), (530), and (540) are further described in application Ser. Nos. 14/922,174 and 16/044,833.

Figure 5B:
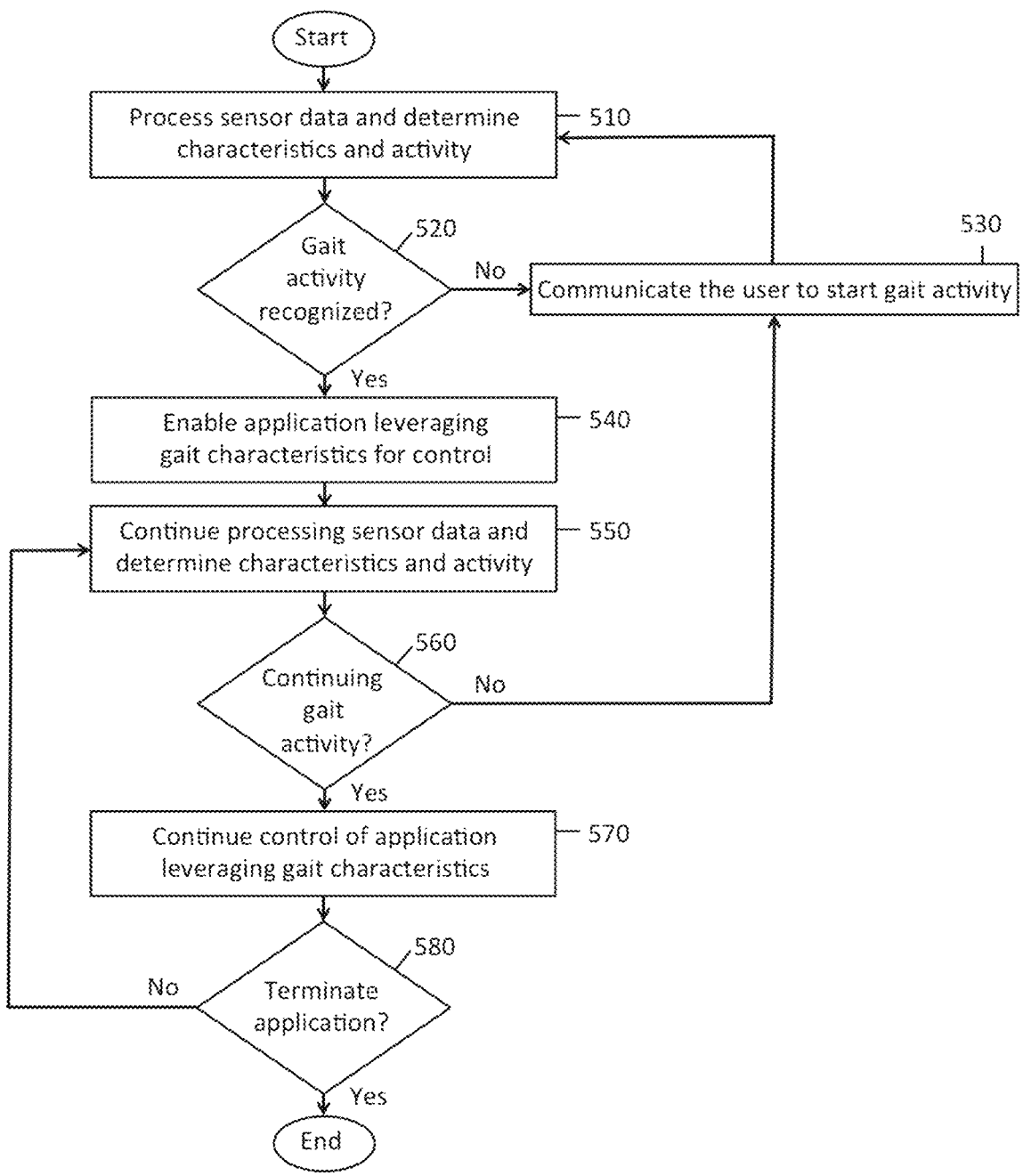
FIG. 5B presents a process flow diagram of another embodiment enabling and controlling an application with the user's gait characteristics.

FIG. 5B represents an extension of the flow diagram of possible basic steps from FIG. 5A that may be applicable to other embodiments. This Figure and its elements (510), (520), (530), (540), (550), (560), (570), and (580) are further described in application Ser. Nos. 14/922,174 and 16/044,833.

Figure 6:
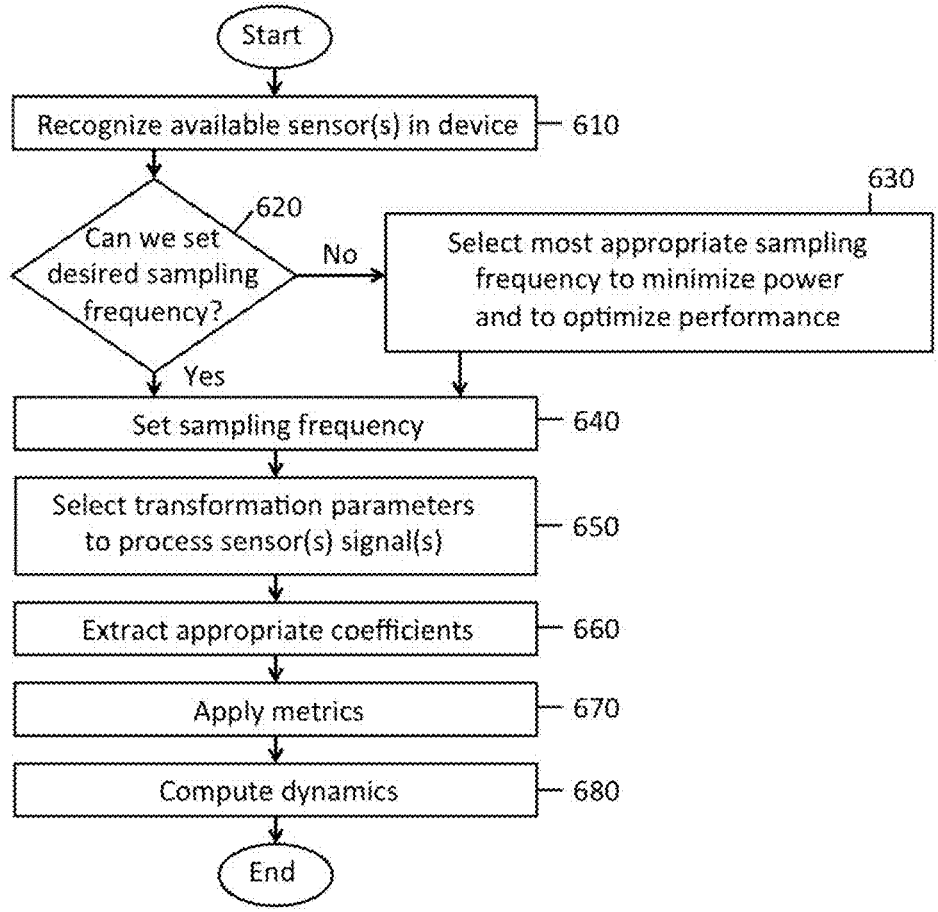
FIG. 6 illustrates a process flow diagram for the user's dynamics information determination according to one embodiment.

FIG. 6 illustrates a flow diagram of one embodiment with possible basic steps of a method for providing a user's dynamics information. In some embodiments, dynamics information may include, by way of example without limitation, velocity, activity, cadence, stride time, stride length, caloric consumption, calories burned per time unit, device position, kinetic energy, etc. and/or any combinations and/or variations thereof. This Figure and its elements (610), (620), (630), (640), (650), (660), (670), and (680) are further described in application Ser. Nos. 14/922,174 and 16/044,833.

Other Background Information Further Described in the Incorporated References:

In some embodiments, an indication of the fundamental frequency or cadence of the gait of a mobile or wearable device user, may be determined through the analysis of a motion sensor signal (e.g. the motion sensor can be a tri-axial accelerometer embedded within the device, and the signal vector module may be analyzed), by means of a Fourier transformation of said signal over a time window. By way of example without limitation, choosing a time window of four seconds (some embodiments may use windows with different time lengths, including by way of example without limitation, 2, 4, 6, 8, 20, 40 seconds or any other amount of seconds) for the motion sensor signal, the Fourier transformation of said signal may provide a representation of its frequency components; in some cases, the strongest frequency component in said representation may coincide with the fundamental frequency of the user's gait or cadence; however, it must be noted that in some conditions, the analysis through the Fourier transformation may deliver misleading results, and special considerations may need to be taken into account to correct those results; by way of example without limitation, the combination of Fourier transformation with other techniques (e.g. wavelet transformation, Hilbert transformation, peak counting, correlation, autocorrelation, thresholding in time domain, and/or any other and/or combinations thereof) may help increase the accuracy in the determination of the user's cadence. By way of example without limitation, a cadence solution obtained through Fourier transformation analysis can be confirmed or rejected by a cadence solution obtained independently by any other technique (in case of rejection, priority can be given, for example, to the solution closest to the past (previous processing) cadence value); and in case of several techniques being used, a majority vote could be employed to decide on the final solution in case of discrepancies. Additional examples of combinations of techniques to obtain cadence are included in the rest of this specification. Any variations of any said elements and/or parameters and/or techniques and/or procedures and/or any combinations thereof may also be possible.

In some embodiments, an indication of the fundamental frequency of a motion sensor signal (or an indication of the cadence of a mobile or wearable device user's gait) can be determined by means of an autocorrelation of the motion sensor signal over a time window. By way of example without limitation, selecting the motion sensor signal over a four seconds time window and performing an autocorrelation of said signal, delivers another signal (for clarity purposes, called second signal, which typically consists of a central maximum surrounded by secondary minima and maxima), from which the inverse of the time distance between the central maximum of said second signal and the largest secondary maximum of said second signal, represents an indication of the fundamental frequency of the original motion sensor signal over said four seconds time window. Some embodiments may use a different length of the time window (e.g. two seconds, six seconds, eight seconds, twenty seconds, sixty seconds, or any other length based on criteria comprising computational costs, dynamism of the solution, accuracy of the solution, frequency content, update frequency, and/or any others). Some embodiments may use different approaches to obtain the previously called second signal, comprising by way of example without limitation, a further division of the signal by its variance, and/or using a pre-processing phase to filter the original motion sensor signal at a particular frequency band (e.g. using a dynamic filter whose central frequency is updated over time based on a previously determined fundamental frequency of the motion signal obtained by means of a frequency transformation; or using the wavelet transformation to filter the motion signal over a range of frequency bands, in response to an indication that the mobile device has experienced a substantial orientation change, wherein said indication is obtained through the analysis of the motion signal with the Fourier transformation), and/or pre-conditioning the original motion sensor signal with any type of filter in any way, and/or using a pre-processing phase to offset the original motion signal in any direction by any amount, and/or using a post-processing phase to perform any of the previously mentioned approaches to reverse some or all of those changes, or to amplify some or all of said changes, or for any other purposes; criteria to follow any of these approaches include: increased accuracy, optimization of computational costs, increased dynamism in the solution, or any other. In some embodiments, any of the mentioned and/or any other additional approaches/methods/techniques/elements/processes and/or any variations and/or any combinations thereof may be used during the pre-processing, post-processing, and in-processing stages, in any way, for any purposes, and according to any criteria.

In some embodiments, the motion sensor leveraged to obtain the user's gait cadence may be an accelerometer; in some embodiments, the motion sensor may be a single-axis accelerometer; in some embodiments, the motion sensor may be a triaxial accelerometer, and each one of the axis may be used independently; in other embodiments, the motion sensor may be a triaxial accelerometer embedded within the device, and the three axial components may be leveraged to obtain a signal vector module; in other embodiments, the motion sensor may be a triaxial accelerometer, and the three axial components may be leveraged to obtain different combinations of correlations, which may be processed to obtain the fundamental frequency of the motion of the device; by way of example without limitation, some embodiments may use the correlation between accelerations of x and y axis and/or the correlation between x and z axis, and/or the correlation between y and z axis, and analyze the resulting signals in the time domain (e.g. event detection by means of thresholding using a moving average of the signal as threshold) or in the frequency domain (e.g. leveraging Short Time Fourier Transform), or by means of any other approach or combinations thereof (e.g. leveraging the wavelet transformation to obtain both time and frequency information of the signal), or any other techniques and/or combinations thereof for any purposes.

In some embodiments, the motion sensor may be embedded within the device; in other embodiments, the motion sensor may be in a wearable unit independent from the mobile device, and positioned in any way and in any location; in some embodiments the motion sensor may be a gyroscope; in other embodiments the motion sensor may comprise an accelerometer (uni-axial or tri-axial) and/or a gyroscope (uni-axial or tri-axial) and/or a magnetometer (uni-axial or tri-axial) and any sensor fusion techniques (e.g. Kalman filtering, particle filtering, or any other) may be leveraged to increase the accuracy of the solution or for any other purposes; in other embodiments, any or all of the mentioned sensors (accelerometer and/or gyroscope and/or magnetometer) may be embedded within the mobile device, and/or independently positioned in any location by means of separate wearable units in any way. Some embodiments may use any combinations of any of the previously mentioned approaches, and/or aspects, and/or elements, and/or processes, and/or any other, in any fashion.

In some embodiments, the time window considered to process the motion sensor signal may be offset over time in any fashion as additional samples from said motion sensor keep arriving for processing. By way of example without limitation, a four seconds time window may overlap 50% with the next four seconds time window selected for the next processing; in other words, the last half of the first time window coincides with the first half of the second time window. In other embodiments, different lengths of time window (e.g. 2, 4, 6, 20, 40 seconds or any other amount of seconds) and/or different overlapping factors and/or different approaches and/or combinations thereof may be used for the continuous processing of the motion sensor signal. In another example of embodiment, a four seconds time window may be selected to process the motion sensor signal every half a second, regardless of the motion sensor sampling frequency (downsampling, upsampling, filtering, and/or any other technique and/or combinations thereof may be leveraged to adapt to particular hardware and/or software conditions); in this example, the overlapping factor is larger than in the previous example, and the update frequency and dynamism (e.g. capability to quickly adapt to changes) of the solution have increased. In some embodiments, any possible overlapping factor, length of time window, update frequency, dynamism of the solution, and/or any other element/feature and/or combinations thereof may be selected. By way of example without limitation, a fixed length time window may be selected and said time window may be offset every time a new sample arrives from the motion sensor (accepting the new arriving sample and discarding the oldest sample from the fixed length time window (again, downsampling, upsampling, filtering, and/or any other technique and/or combinations thereof may be leveraged to adapt to particular hardware and/or software conditions, if needed)), in such a way that the update frequency of the solution may be equal to the sampling frequency of the motion sensor; in other words, we may obtain the fundamental frequency (or cadence) of a mobile device user with an update frequency equal to the motion sensor sampling rate; in some embodiments, by way of example without limitation, the device motion sensor sampling rate may be equal to 60 Hz, or 120 Hz, thus obtaining an update frequency for the user's cadence greater than the user's step frequency; this is an important aspect for certain applications requiring increased dynamism in the solution (for example to control an aspect of an application or to control a process in a mobile device with the user's cadence, with an update frequency greater than the user's step frequency, thus improving the user's experience over other approaches). In other embodiments, we may work with any other motion sensor sampling rates and leverage upsampling, downsampling, filtering or any other technique to obtain an update frequency for the user's cadence higher or lower than the user's step frequency.

In some embodiments, during the processing of the original motion sensor signal (e.g. signal from an accelerometer within the device) over a time window to determine the fundamental frequency (or cadence) using autocorrelation, a pre-processing phase may be included to filter said motion sensor signal in any fashion (e.g. filter as a result of a frequency analysis, e.g. Fourier analysis or any other, of said signal); by way of example without limitation, said signal may be applied a Fourier transformation from where the frequency components of said signal may be analyzed; in particular, focusing on the frequency components below a threshold of, for example, 0.5 Hz, and above 0 Hz, if these low frequency components are stronger than the rest of frequency components of the signal (e.g. their amplitudes in the Fourier transformation domain are larger than the amplitudes of the rest of frequency components of said Fourier transformation above 0.5 Hz), that may indicate a substantial orientation change experienced by the device. Additional descriptions on this and other topics can be found at least in the incorporated references.

Traditional approaches to determine cadence may fail when facing abrupt changes in cadence, because their processing of the motion signal may assume, for instance, a selected minimum time length of the user's step, or a selected frequency range of the user's cadence; the problem may be specially important when the abrupt changes in cadence (e.g. from 1 Hz to 2 Hz) result in the new cadence value (2 Hz) occupying some harmonic frequency of the previous values of cadence (1 Hz), in such a way that traditional methods may think of the new cadence value (2 Hz) as an harmonic of the previous cadence value (1 Hz), and find a subharmonic (½) of the new cadence (2 Hz) to be considered as the real cadence because it matches previous cadence values (1 Hz); consequently, traditional approaches would keep wrongly tracking said subharmonic as the fundamental frequency. Other examples may comprise any possible combinations and/or modifications of any of the concepts (including harmonics, subharmonics, and their orders) and/or figures and/or elements of the previous examples. It is worth noting that the problems may also arise with changes in cadence not necessarily involving integer multiples and/or submultiples of the original fundamental frequency.

In some embodiments, abrupt changes in the device user's cadence may be detected leveraging frequency and time information of the motion sensor signal (e.g. accelerometer signal, wherein said accelerometer is within the device). Additional descriptions on this and other topics can be found at least in the incorporated references.

Some embodiments may leverage the previously mentioned information about the user's steps in combination with other metrics to enhance user's dynamics information, comprising velocity and activity. It is worth noting that in some embodiments, the user's cadence may be considered as the user's step frequency (inverse of the user's step time period). Some embodiments may leverage the obtained information on user's steps in combination with the information on user's dynamics to determine stride length. By way of example without limitation, using the physics principle velocity equals distance over time, once we have determined velocity, we can obtain distance (e.g. stride or step length) by using the time of each stride or step (step frequency (cadence) equals inverse of the user's step time period). Some embodiments may leverage the information on user's dynamics to compute distance. Some embodiments may enhance distance through the combination of user's dynamics information with localization information. Some embodiments may use different techniques, principles and/or methodologies to obtain all the previous information and metrics, including but not limited to machine learning. In some embodiments, all the computation, processing, information presentation, and other steps may be carried out within a single mobile device without the need of external resources. In some embodiments, the computation or some other step or combinations of steps may be performed external to the mobile device, or with the assistance of some external element, such as external sensor, server, database or any other element. In some embodiments, software may be stored on the mobile or wearable device, for instance, in its memory for execution by its processor or processors. Some embodiments may store data structures and code on computer readable storage medium, which by way of example, and not limitation, may comprise field-programmable gate arrays, application-specific integrated circuits, magnetic and/or optical storage devices, etc.

In some embodiments, the sensor portion of the device or the device itself or any other device containing a sensor and with the capability to communicate in any fashion with the user's device, or any other type of device or accessory may be positioned or attached to any part of the user, including by way of example without limitation, the wrist, arm, hand, face, head, waist, chest, pocket, hat, shoe, any type of clothing, accessories and any combinations thereof and in any way. In some embodiments, the system may be trained to recognize and/or learn activity, motion type, attachment position of the device, movement characteristic, etc. In some embodiments, analysis of acceleration signature may help determine activity, motion type, attachment position of the device, movement/gait characteristic, etc. By way of example without limitation, the acceleration signal may be processed to identify maximums, minimums, mean, standard deviation, frequency components, period, orientation, distribution of peaks, patterns, etc. and/or combinations thereof in order to help determine activity, motion type, attachment position of the device, movement/gait characteristic, etc. In some embodiments, Fourier analysis, any kind of filtering, peak counting, determination of frequency components leveraging the wavelet transform or any other method and combinations thereof may also be utilized to determine user's gait activity, characteristics, etc. In some embodiments, any type of prompt to the user may also be leveraged to request information about his/her activity, motion type, attachment position of the device, movement/gait characteristic, etc. In some embodiments, activity, motion type, attachment position, movement/gait characteristic, etc. may be determined through correlation of any type of sensor values or any type of parameter or metric generated with them, based on any type of model that has been calibrated in any fashion for a particular activity, motion type, attachment position, movement characteristic, etc. In some embodiments, any other sources, means, methods and/or configurations may be leveraged to determine activity, motion type, attachment position, movement/gait characteristic, etc., including by way of example without limitation, the use of sensors and/or signals obtained independently of the sensed acceleration (e.g. GPS), the use of statistics and/or any other empirical information, algorithms, databases or other information stored anywhere and in any fashion, combinations thereof, etc. In some embodiments, the referred methods, configurations, systems, etc. may be modified, updated and/or calibrated in any way, periodically or continuously over any time interval.

Some embodiments may include any external sources to obtain any parameter or information about movement, environment, context, etc. including by way of example without limitation, speed and/or distance monitors, any number of portable electronic devices (e.g. GPS receivers, any kind of computing and/or communications device, etc.), databases and/or networks. In some embodiments, other types of inputs may also be utilized, including by way of example without limitation, buttons, keys, keyboards, keypads, touchpads, joysticks, etc., which may be used in any fashion. Any type of satellite based navigation systems, cellular communications networks and other systems/networks may also be used to obtain speed in some embodiments (and/or provide feedback to help correct errors) under certain conditions.

In some embodiments, additional inputs may include traces from touch-sensitive screens, button presses, gesture recognition, voice commands, switches, and/or any other type of technological, physical or any nature means that allow the user to interact, and combinations thereof. In some embodiments, in addition to using gait characteristic for control, further control may be performed through any additional movements that the user may perform with the device, such as any type of tilting or any kind of gestures, including by way of example without limitation, any kind of raise, swing, twist, touch, press, swipe, drag, double touch, pinch, etc., and combinations thereof, regardless of performing them with or without direct contact to the device screen or any other element (e.g. the user may perform the pinch gesture touching a screen or in the air without touching a solid element). In some embodiments, any type of method may be employed to distinguish between different types of gestures, swings, twists, etc. that the user makes while he/she performs a pedestrian activity (e.g. walk, jog, run, etc.); by way of example without limitation, frequency analysis, filtering, acceleration thresholding, analysis of projection of gravity vector, feedback from other sensors, or any other technique/method and combinations thereof may be employed.

In some embodiments, the acceleration sensor may be an electrostatic or capacitance-coupling type, or any other technology (e.g. piezoelectric or piezoresistance type) now existing or later developed, and may be configured to deliver three-axis, two-axis, or one-axis acceleration. In some embodiments, in addition to accelerometers, any other type of technologies and/or sensors such as gyroscopes, magnetometers, pressure sensors, cameras, GPS, etc. may be used in any way to enhance accuracy or for any other purposes. In some embodiments, the user may have any number of any type of sensors, sensor units, devices, or accessories located anywhere in any fashion to determine the characteristics of his/her movement and/or for control or any other purposes.

In some embodiments, any processing, detection, recognition, or any other actions or operations may be performed regardless of the mode, state or any other condition of the device, application or any other entity, process or element. In other embodiments, any number of conditions and/or criteria of any type must be satisfied before proceeding with any of said actions or operations.

Any of the embodiments herein described may be implemented in numerous ways, including as a method, an apparatus, a device, a system, a computer readable medium, etc., and also be applicable in any environment, application (game, non-game, etc.), condition, etc. regardless of number of users, physical proximity, communication means, device, or any other factor.

Other configurations are also possible. By way of example, and not limitation, in some embodiments, all or part of the processes may be performed by chip-level systems, third-party applications, operating system kernel, firmware, or any other combination of hardware and/or software. In some embodiments, the software may be delivered in a variety of forms, including but not limited to, as stand-alone application, as library, as application programming interface, etc. In general, the functions of particular embodiments may be achieved by any means as is known in the art. Some embodiments may use distributed, networked sensors and/or systems, components, servers, databases, and/or circuits, and/or any combination of additional hardware and/or software and/or processing techniques and methodologies. Some embodiments may use any other type of sensor and/or system.

In some embodiments, sensors may be any of several types including, by way of example, and not limitation, any type of device, transducer or any other type of apparatus which may measure some quantity; in some embodiments, sensors may be implemented in any size, with any type of technique and technology, including but not limited to electronic, microelectronic, nanoelectronic, etc. By way of example, and not limitation, sensors may comprise any type of accelerometer, magnetometer, gyroscope, pressure sensor, proximity sensor, etc. and any other type of device sensitive to radio-frequency, sound, ultrasound, light, etc. including but not limited to, GPS antennas and/or their sensitive elements, WiFi antennas and/or their sensitive elements, and any other type of radio-frequency technology antennas and/or their sensitive elements. In some embodiments, sensors are integrated within the mobile or wearable device. In some embodiments, sensors or other mobile or wearable devices may be distributed outside the main mobile or wearable device, and they may communicate with the main mobile or wearable device by any means. Communication or transfer of data may be wired, wireless, or by any other means. In some embodiments, the user or other entity may rearrange characteristics of the components, or other features or elements of the system and the system may automatically adjust to new settings or arrangements.

Figure 7:
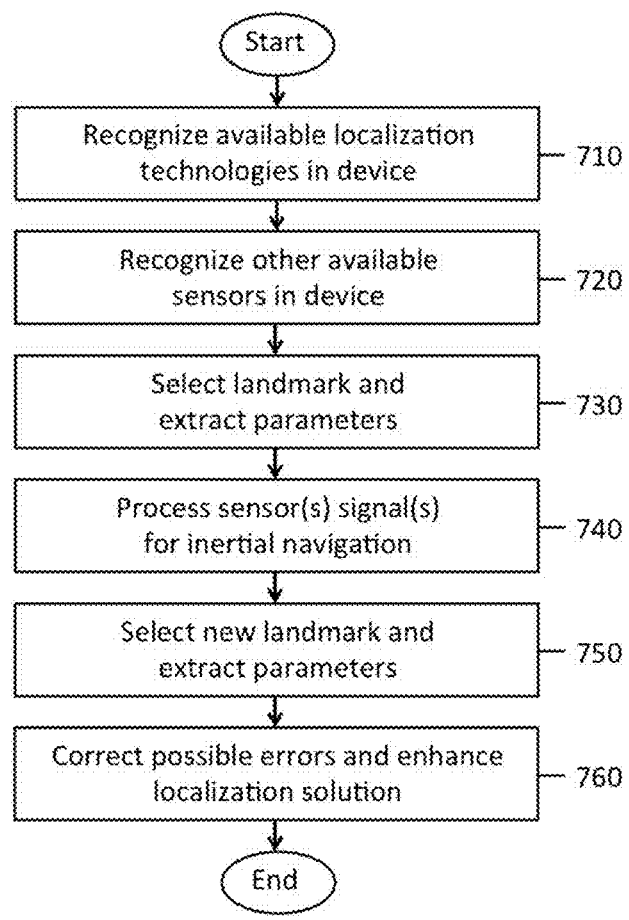
FIG. 7 illustrates a flow diagram for the process to enhance a user's dynamics and localization information according to one embodiment.
Figure 8:
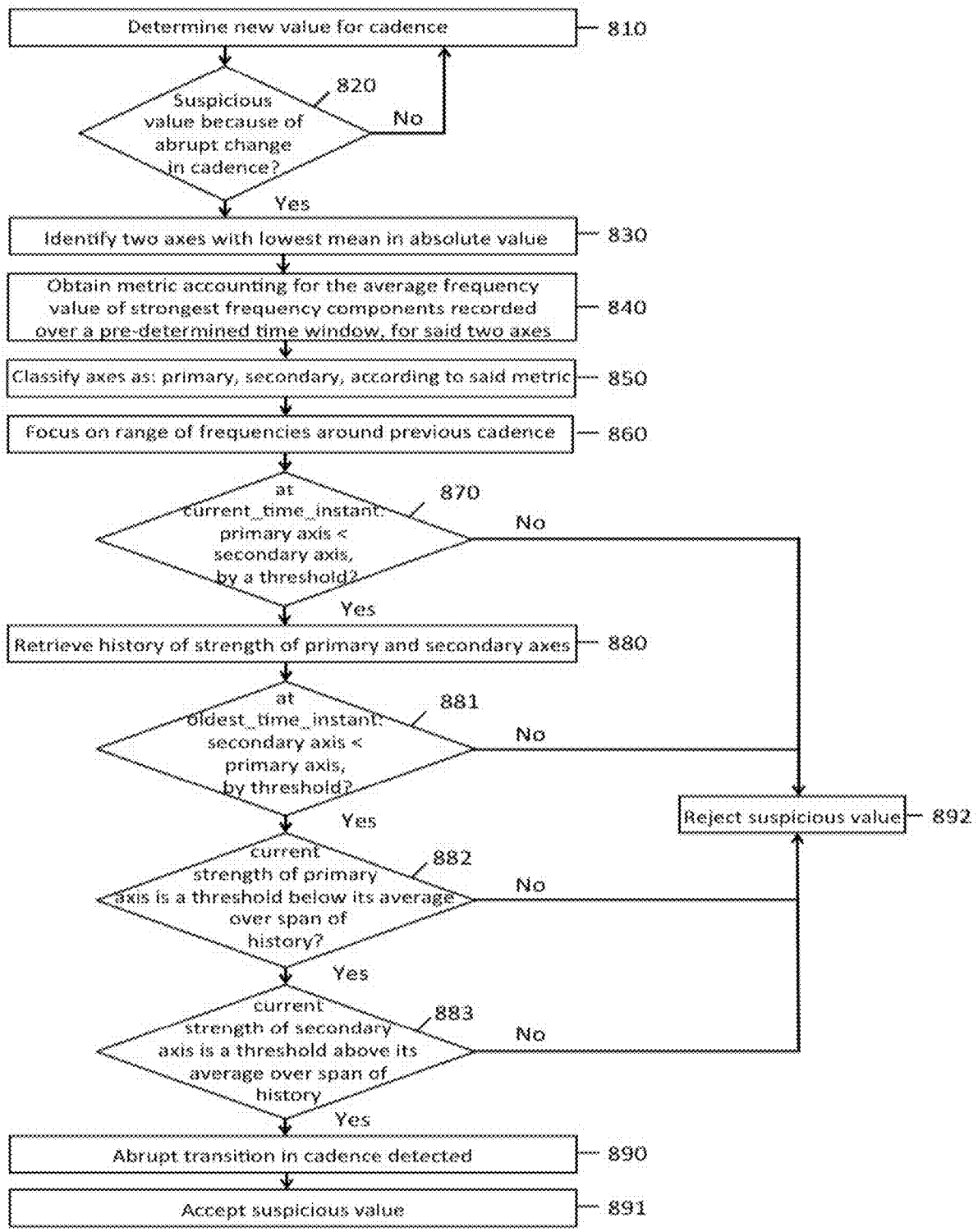
FIG. 8 illustrates a flow diagram for the process to detect an abrupt change in cadence according to one embodiment.

In some embodiments, a method for enhancing a user's dynamics and localization information may be used as shown in FIG. 7, which illustrates a flow diagram of possible basic steps. This Figure and its elements (710), (720), (730), (740), (750), and (760) are further described in application Ser. Nos. 14/922,174 and 16/044,833.

Some embodiments may use all the available information to identify the position (and transitions between positions) of the mobile device within the user's body, as described in application Ser. No. 16/044,833.

Analogously, some embodiments may leverage any machine learning algorithm/methodology (e.g. support vector machine, decision tree, Naïve Bayes, or any other) to determine any gait attribute(s) (e.g. velocity and/or stride length and/or calories burned per time unit and/or activity and/or device position and/or other and/or any variations and/or combinations of any number of them), in a device process and/or application and/or in the context of controlling a user's representation, making use of the determined user's cadence (or fundamental frequency) as a feature for the determination of said gait attribute(s). For example, we can follow any of the procedures described within this application or any other to determine a gait attribute leveraging a machine learning algorithm and a training set of data to model said attribute, so that said model can be implemented in the device process and/or application and/or in the context of controlling a user's representation, and used to determine said gait attribute(s) by leveraging a set of features computed for said determination (in real time and with an update frequency larger than the user's step frequency or any other). In some embodiments, the features computed for said determination include the user's gait cadence; consequently, cadence will need to be also computed and recorded during the gathering of training data; in some embodiments, the features computed for said determination include the user's gait cadence and/or mean and/or variance and/or standard deviation and/or skew and/or kurtosis and/or principal frequency component and/or energy in selected frequency bands, and/or any other obtained from e.g. accelerometer data over a time window; in other embodiments, any variations and/or combinations thereof may also be possible. Some embodiments may use any of the procedures/strategies/methodologies described within this application and/or any other for the determination of the user's cadence to be used as a feature, including, by way of example without limitation: 1) analyzing a motion sensor signal using a combination of techniques comprising: wavelet transformation, Fourier transformation, and autocorrelation and/or 2) detecting abrupt changes in the user's cadence leveraging frequency and time information of the motion sensor signal.

FIG. 9A, 9B, 9C, 9D, 9E, 9F show scaled representations of images strip files used for animation. They have been scaled to fit in the document of this patent application, but their sizes can be chosen depending on a plurality of criteria, including by way of example without limitation, the available memory for the application using said images strips in the mobile or wearable device, the amount of heap memory expected to be used by the application in the mobile or wearable device, the screen size (e.g. physical size in terms of height millimeters*width millimeters or height pixels*width pixels) of the mobile or wearable device where said images strips are going to be used, the proportion of the device screen expected to be occupied by the animation, the density of the screen of the device (e.g. number of pixels per squared inch), the available storage capacity of the mobile or wearable device, any design and/or esthetic choices made by the developer of the application, and/or any other criteria and/or variations thereof and/or any combinations of any of the elements, criteria, and/or any other.

In a particular embodiment intended for an application in an Android device, FIG. 9A, 9B, 9C, 9D, 9E, 9F may represent images strip files with png extension (other file formats, e.g. jpg extension or others, may also be possible) stored in the "assets" folder of the mobile application, or in the "res/drawable-mdpi" folder of the mobile application, or in any other appropriate possible location chosen by the application developer. Criteria to choose folder in which to store the images strip files may include, by way of example without limitation: the expected density of the device screen (e.g. folder name with extension of: mdpi is usually assigned to resources for medium-density (mdpi) screens (~160 dpi), ldpi to resources for low-density (ldpi) screens (~120 dpi), hdpi to resources for high-density (hdpi) screens (~240 dpi), xhdpi to resources for extra-high-density (xhdpi) screens (~320 dpi), xxhdpi to resources for extra-extra-high-density (xxhdpi) screens (~480 dpi), xxxhdpi to resources for extra-extra-extra-high-density (xxxhdpi) uses (~640 dpi), etc.), the way the operating system of the device handles image files (bitmap files) in memory, the resources of the device (e.g. storage capabilities, memory, etc), and/or any other and/or any variations and/or combinations thereof. In one example of embodiment, FIG. 9A, 9B, 9C, 9D may be images strip files with png extension stored in the "assets" folder, with dimensions: 3146 pixels*145 pixels (again, sizes can be chosen depending on a plurality of criteria, as discussed above), with color space RGB (although in this patent application drawings have been grayscaled), containing 26 (in other embodiments, may contain 22, 16, or other numbers depending on criteria such as: type of activity being displayed, expected gait frequency of the activity, etc.) frames (sub-images) corresponding to a complete gait cycle (e.g. 26 frames span one complete gait (walking, jogging, running, or any other activity) cycle). In other words, these images strip files contain 26 frames (26 sub-images of 121 pixels*145 pixels each) arranged consecutively and timely ordered in such a way that displaying the frames consecutively in a device screen one after the other fast enough (e.g. frequency larger than 12 Hz) to make the human eye perceive them as continuous movement, we can achieve the effect of animation; this is a well-known technique used for example in cinemas, displaying consecutive frames fast enough (e.g. frequency of approximately 25 Hz), to achieve the illusion of animation to the human eye. By way of example without limitation, if the 26 frames are displayed on the device screen sequentially and continuously and cyclically repeated (frame 1, frame 2, frame 3, . . . , frame 25, frame 26, frame 1, frame 2, frame 3, . . . , frame 25, frame 26, frame 1, frame 2, . . . , and again and again), the device user will have the illusion that the person in the frames is walking continuously.

Figure 9A:
FIG. 9A, 9B, 9C, 9D, 9E, 9F show images strip files for a representation of a user with different gait attributes according to one embodiment.
Figure 9B:
Figure 9C:
Figure 9D:
Figure 9E:
Figure 9F:

FIG. 9E, 9F may represent images strip files with png extension, stored in the "assets" folder, with dimensions: 2662 pixels*145 pixels and 1936 pixels*145 pixels respectively (again, sizes can be chosen depending on a plurality of criteria, as discussed above), with color space RGB (although in this patent application drawings have been grayscaled), containing a number of frames of 22 and 16 respectively. In this example of embodiment, FIG. 9E, 9F represent complete cycles of running for a person, in contrast with FIG. 9A, 9B, 9C, 9D, which represent complete cycles of walking. It is worth noting that in this particular embodiment, FIG. 9E, 9F may have a number of frames (e.g. 22, 16) different from FIG. 9A, 9B, 9C, 9D (e.g. 26 frames), because FIG. 9E, 9F represent running cycles, while FIG. 9A, 9B, 9C, 9D represent walking cycles. In general, running cycles may be carried out faster than walking cycles, so the number of frames needed to cover a whole cycle (achieving good illusion of animation to the human eye) may be smaller for running than for walking. And even representing the same activity (e.g. running), an images strip file may have even smaller number of frames (e.g. 16 instead of 22) if the running activity represented in said strip is expected to be carried out at a faster frequency (e.g. FIG. 9F represents a running mode faster than the one represented in FIG. 9E, and consequently, it can use a smaller number of frames to complete the cycle, still achieving good illusion of animation to the human eye). On the other hand, some embodiments may use the same number of frames for all image strips regardless of the activity represented, following criteria including, by way of example without limitation, prevention of memory management problems (e.g. images strip files with different number of frames generally will have different sizes in terms of number of pixels (pixels height*pixels width), which will translate into allocations of blocks of memory of different sizes (typically the amount of memory allocated for an image file or a bitmap file may be equal to the number of pixels in height of the image, multiplied by the number of pixels in width of the image, multiplied by 4, if the amount of information bits used per pixel is 4); for instance, in the previous example, where the walking images strips have a size of 3146 pixels*145 pixels, the amount of memory allocated for each strip is: 3146*145*4~=1.8 MB; if the application is running low on memory, a procedure called garbage collection may be triggered to free unused blocks of memory; however, if we need to allocate a new image and the available memory is fragmented into small blocks of different sizes, none matching with the size required to allocate our new image, the application could face an "out of memory" error, which in some circumstances could be prevented if we use image files of the same size, and release or recycle an unused image file before trying to allocate a new image file). Different embodiments may have images strips with different numbers of frames (even if the strips represent the same type of activity). Other embodiments may use different approaches/methodologies and/or any others and/or any variations and/or combinations thereof.

In some embodiments, the user's representation shown in the images strip files (e.g. the person in FIG. 9A, 9B, 9C, 9D, 9E, 9F, 10A, . . . 10F) may take any other form(s), including, by way of example without limitation, any type of person, avatar, object, vehicle, robot, and/or any of the entities/forms mentioned in reference to element (110) in FIG. 1C, and/or any other elements in FIG. 1C and FIG. 2B, with any characteristics, and/or any other, and/or any variations and/or combinations thereof.

Figure 10A:
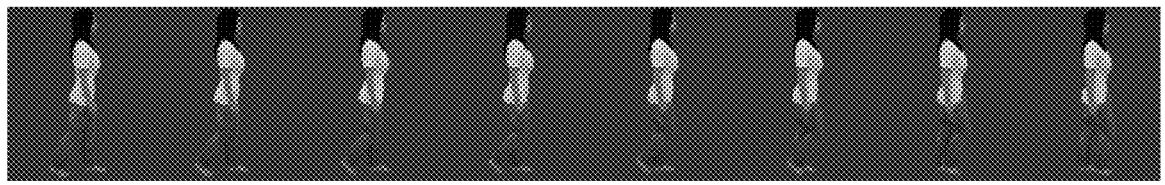
FIG. 10A, 10B, 10C, 10D, 10E, 10F show scaled portions of the previous images strip files for a representation of a user with different gait attributes according to one embodiment.
Figure 10B:
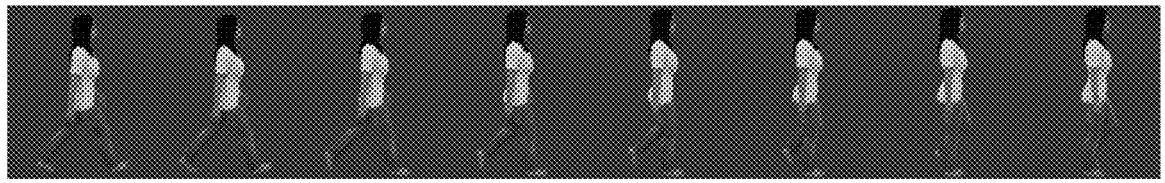
Figure 10C:
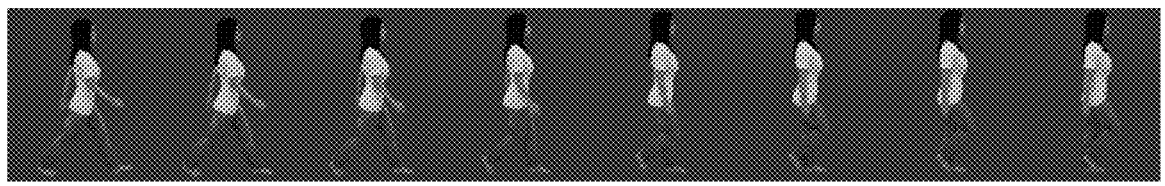
Figure 10D:
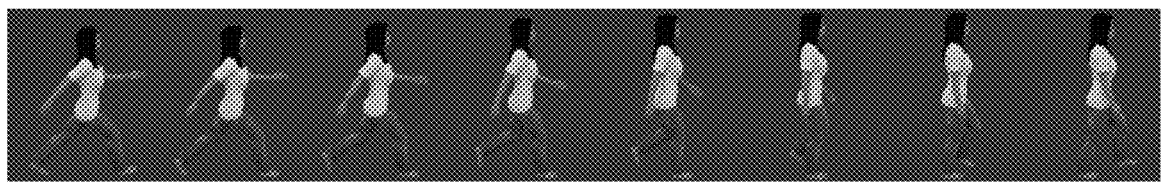
Figure 10E:
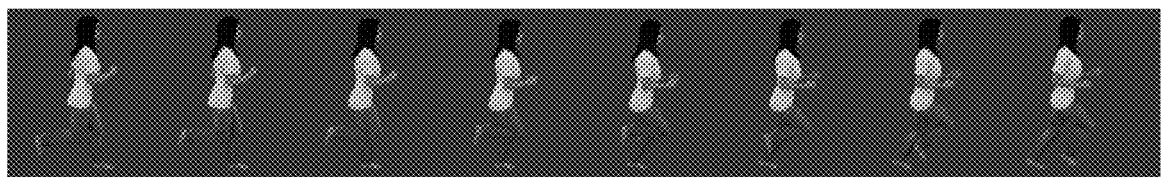
Figure 10F:
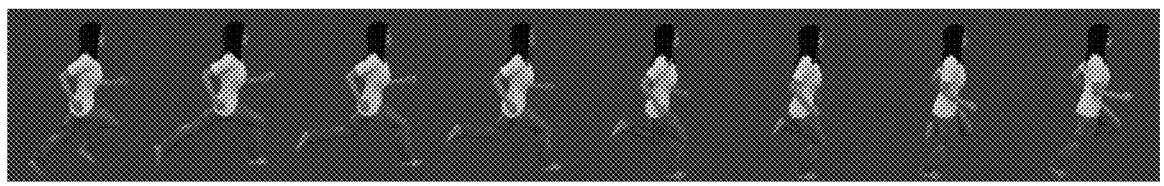

Since we want to show in real time changes in the user's representation being displayed on the device screen when the device user changes his/her gait (and/or gait attribute(s)), we can use different images strip files with different characteristics to show the differences brought by the change in the user's gait. By way of example without limitation, FIG. 9A, 9B, 9C, 9D represent walking cycles, but with different characteristic for the person being displayed on the screen; for instance, FIG. 9A displays a relatively short stride length for the person displayed, while FIG. 9B shows a bit larger stride length, FIG. 9C shows a larger stride length, and FIG. 9D shows a very large stride length; on the other hand, FIG. 9E, 9F represent running cycles, but also with different characteristic for the person being displayed on the screen; for instance, FIG. 9E displays a relatively short stride length for the person displayed as running, while FIG. 9F shows a larger stride length for the person displayed as running. These and other details can be observed more clearly in FIG. 10A, 10B, 10C, 10D, 10E, 10F, which represent scaled (zoomed in) portions of FIG. 9A, 9B, 9C, 9D, 9E, 9F respectively; in particular, we can see that the walking cycles represented in FIG. 10A, 10B, 10C, 10D, present different characteristics in the person being displayed; for instance, the stride length increases progressively from FIG. 10A to FIG. 10D, but there are also progressive changes in other details, such as, by way of example without limitation, the swing of the arms, the angles of the knees when taking new steps, the angles of the elbows, the back and forth movement of the head (achieved e.g. through appropriate rotations of the bone(s) controlling the head movement), the rotation of the hips, the rotation of the shoulders, the rotations of the feet, the change in elevation of the hips, the forward angle of the upper body, etc; these details and additional ones may be seen more clearly in FIG. 10E, 10F, which represent different running cycles, also showing differences in, by way of example without limitation, the way the fingers in the hands are grouped together in the form of a fist, the way the forearms shake, the way and angles in which the arms rotate, the angles of the thighs with the vertical direction, the angle at which the feet land on the ground with every step, the way the hair moves and bounces with every step, etc. In some embodiments, all the parts of the body shown in any of the figures FIG. 9, FIG. 10, may be controlled (e.g. their location, rotation, scale, surface texture, material, color, etc. may be chosen/modified/controlled by the designer rendering them appropriately, and/or by a programmer selecting their values/features programmatically, etc.) following any criteria.

In one example of embodiment, the effect of animation to the human eye can be achieved as described next. First, we are making the following assumptions for this particular example of embodiment: the mobile device the user is carrying is a smartphone; the operating system of the mobile device is Android; other embodiments may use different devices (e.g. smart glasses, smart watches, and/or any other type of mobile or wearable device, running in any type of operating system (by way of example without limitation, iOS by Apple, or any other)); the version of the operating system is Android 6.0.1. The mobile device has a touch screen of 4.5 inches (480 pixels*854 pixels), a 1.1 GHz Quad Core chipset, 1 GB RAM+8 GB ROM, supports microSDXC card up to 32 GB, and has the typical wireless and other type of functionalities of an average smartphone. An application is developed for said example of smartphone (again, other embodiments may use any other type of device, characteristics, elements, and/or any other and/or any variations and/or combinations thereof) using any of the available software and/or hardware and/or any other type tools (e.g. a MacBook Pro with OS X El Capitan, processor of 2.4 GHz, memory of 8 GB, equipped with integrated development environment such as Eclipse or Android Studio, together with any available plugins, tools (e.g. Android Development tools, Android SDK tools, or any other), and/or any other elements if needed). One possible example of embodiment for the developed Android application can be described with the help of the Java-style pseudocode shown below, which will be used to discuss details of how the animation (or control of the user's representation) can be achieved on a mobile device screen in one embodiment. Different embodiments may use different approaches, and even the same approach can be tackled in different ways using a variety of alternative software and/or hardware resources; any modifications and/or combinations of any elements and/or procedures and/or any other type of entity may also be possible in some embodiments. As shown in the pseudocode below, a class extending the SurfaceView class and implementing the SurfaceHolder.Callback interface may be created, named AnimationView; one of the purposes of the SurfaceView class is to provide a surface in which a secondary thread can render into the screen; when used in this way, we should to be aware of some threading semantics: 1) All SurfaceView and Surface Holder.Callback methods will be called from the thread running the SurfaceView's window (typically the main thread of the application). They thus need to correctly synchronize with any state that is also touched by the drawing thread. 2) It is important to ensure that the drawing thread only touches the underlying Surface while it is valid—between SurfaceHolder.Callback.surfaceCreated( ) and SurfaceHolder.Callback.surfaceDestroyed( ). The SurfaceHolder.Callback interface may be implemented to receive information about changes to the surface.

Part 1 of Pseudocode

```
class AnimationView extends SurfaceView implements SurfaceHolder.Callback {
    class AnimationThread extends Thread implements SensorEventListener, OnTouchListener {
        Bitmap imagesStrip;
        long frame_0_StartTime;
        boolean beginning_manageCurrentFrame=true;
        long timeIntoCompleteAnimation;
        int frameCount=26;
        int completeAnimationPeriod=1000; //To be programmatically changed.
        int currentFrame=0;
        int frameWidth=300, frameHeight=360;
        Rect frameToDraw=new Rect(0,0,frameWidth,frameHeight);
        float personXPos=0, personYPos=0;
        RectF whereToDraw=new RectF(personXPos,personYPos,personXPos+frameWidth,personYPos+frameHeight );
        //Additional code not included for clarity purposes.
        public void manageCurrentFrame( ) {
            long time=System.currentTimeMillis( );
            if (beginning_manageCurrentFrame && currentFrame==0) {
                frame_0_StartTime=time;
                beginning_manageCurrentFrame=false;
            }
            timeIntoCompleteAnimation=time-frame_0_StartTime;
            currentFrame=
            (int)(timeIntoCompleteAnimation*frameCount/completeAnimationPeriod)
```

```
        % frameCount;
    frameToDraw.left=currentFrame*frameWidth;
    frameToDraw.right=frameToDraw.left+frameWidth;
    }
Part 2 of Pseudocode
    private void doDraw(Canvas canvas) {
        manageCurrentFrame( );
        canvas.drawBitmap(imagesStrip,frameToDraw,where-
            ToDraw,null);
    }
    public void setAnimationImagesStrip(int stripResource) {
        imagesStrip.recycle( );
        imagesStrip=null;
        AssetManager assets=getResources( ).getAssets( );
        InputStream buffer;
        String myFilename=" ";
        if (strip Resource==0) {
            myFilename="firstImagesStripFile.png";
        } else if (stripResource==1) {
            myFilename="secondImagesStripFile.png";
        } else if (stripResource==2) {
            myFilename="thirdImagesStripFile.png";
        }
        try {
            buffer=new  BufferedInputStream(assets.open(my-
                Filename));
            imagesStrip=BitmapFactory.decodeStream(buffer);
        } catch (IOException e) {e.printStackTrace( );}
        imagesStrip=
    Bitmap.createScaledBitmap(imagesStrip,
frameWidth*frameCount,frameHeight,tru e};
    }
    }
}
Part 3 of Pseudocode
    public void onSensorChanged(SensorEvent event) {
        if(event.sensor.getType(  )==Sensor.TYPE_ACCELER-
            OMETER){
            double x_acceleration=(double)event.values[0];
            double y_acceleration=(double)event.values[1];
            double z_acceleration=(double)event.values[2];
            double signal_vector_module_acceleration=
                Math.sgrt((x_acceleration*x_acceleration)+
                (y_acceleration*y_acceleration)+
                (z_acceleration*z_acceleration));
            double[ ] array_returned_from_determine_gait_param-
                eters=
                determine_gait_parameters(x_acceleration,y_accel-
                    eration,
                z_acceleration,signal_vector_module_acceleration);
            double
                velocity=array_returned_from_determine_gait_
                parameters[0];
            double calories=array_returned_from_determine_gait_
                parameters[1];
            double
                cadence=array_returned_from_determine_gait_
                parameters[2];
            double activity=array_returned_from_determine_gait_
                parameters[3];
            int previous_completeAnimationPeriodInMsec=
                completeAnimationPeriod;
            int    new_completeAnimationPeriodInMsec=(int)
                (1000*2/cadence);
            if
(new_completeAnimationPeriodInMsec!=previous_
completeAnimationPeriodInMsec){
                long time_now=System.currentTimeMillis( );
                frame_0_StartTime=time_now-(int)(
new_completeAnimationPeriodInMsec*
                (timeIntoCompleteAnimation % previous_completeAni-
mationPeriodInMsec)/
                (double)previous_completeAnimationPeriodInMsec);
                completeAnimationPeriod=new_completeAnimation
                    PeriodInMsec;
            }
        }
    }
```

Within the AnimationView class, a class named AnimationThread may be created extending the Thread class and implementing the interfaces SensorEventListener (used for receiving notifications from the SensorManager when sensor values have changed), and OnTouchListener (for a callback to be invoked when a touch event is dispatched to the view. The callback will be invoked before the touch event is given to the view). A Thread is a concurrent unit of execution. It has its own call stack for methods being invoked, their arguments and local variables. Each application has at least one thread running when it is started, the main thread, in the main ThreadGroup. The runtime keeps its own threads in the system thread group. There are two ways to execute code in a new thread. You can either subclass Thread and overriding its run( ) method, or construct a new Thread and pass a Runnable to the constructor. In either case, the start( ) method must be called to actually execute the new Thread. Each Thread has an integer priority that affect how the thread is scheduled by the OS. A new thread inherits the priority of its parent. A thread's priority can be set using the setPriority(int) method.

Focusing on the pseudocode, the 12 lines following the first 2 lines, are used to declare some variables needed for the management and drawing of the images. For instance, imagesStrip is defined as a Bitmap to hold the information (in memory) of the image strip file we want to work with; frame_0_StartTime is defined as a long variable to hold the time (in milliseconds) at which the 0th (in other words, first) frame was started to be displayed on the screen, thus serving as an origin reference point in time; beginning_manageCurrentFrame is defined as a boolean variable (initially set to true) to indicate whether we are entering the manageCurrentFrame method for the first time; once said method is entered (and if currentFrame is equal to zero), beginning_manageCurrentFrame will be set to false; timeIntoCompleteAnimation is defined as a long variable to hold the time (in milliseconds) elapsed since an origin reference point in time, thus allowing us to know how deep into a complete animation cycle we are in terms of time; frameCount is defined as an integer variable (set to 26 in this particular example, but any other values are also possible, and it could even be changed programmatically in the application), and its purpose is to account for the number of frames (sub-images) in the images strip file(s) (e.g. with extension png) we are working with; in some embodiments, it may be advisable to keep frameCount constant across different images strip files to prevent memory segmentation that could lead to "out of memory" errors under some circumstances (e.g. low memory conditions); completeAnimationPeriod is defined as an integer variable, and its purpose is to hold the amount of milliseconds a complete animation period should last (initially set as 1000 in this particular example, for instance, assuming 2 Hz cadence, the complete animation (2 steps) period=1 second=1000 milliseconds; nevertheless this value should be programmatically changed based on the determined cadence or fundamental frequency of the user; for instance, if the determined cadence is 1 Hz, the complete animation (2 steps) period=2 seconds=2000 milliseconds); currentFrame is defined as an integer (initially set to zero), and its purpose is to account for the order of the frame (e.g. from 0 to 25 if we work with 26 frames, and cyclically repeating (e.g. . . . , 24, 25, 0, 1, . . . )) within the images strip file we are working with, that is to be displayed on the screen for the purpose of achieving animation to the human eye; frameWidth and frameHeight are defined as integers (initialized to 300 and 360 in this particular example, but other values are also possible), and their purpose is to set the actual dimensions of the frame when displaying it on the device screen, in terms of the actual number of pixels the frame will occupy on the screen of the device.

It is worth noting that these values can be modified in any way for other embodiments depending on a plurality of criteria, including by way of example without limitation, the physical size of the screen of the device, the density of pixels of the screen, the amount of heap memory an application is allocated in the device, the amount of heap memory an application is expected to allocate for bitmaps, design criteria of the developer, and/or any variations and/or combinations thereof; it is also worth noting that these numbers do not need to match the actual physical dimensions of the frames in the images strip file (e.g. png extension), because Android OS allows scaling (increase or reduction) of the bitmaps in memory, before displaying them on the screen of the device; frameToDraw is defined as a Rect variable (rectangle), specifying the rectangular region to be selected from the scaled bitmap (to be obtained from the images strip file), to be displayed on screen; said rectangular region is delimited by means of the (x,y) coordinates of its top-left point (in this example, (0,0)) and the (x,y) coordinates of its bottom-right point (in this example, (frameWidth,frameHeight)); in this particular example of initialization, Rect(0, 0,frameWidth,frameHeight), we are delimiting the rectangular region covered by the first frame within the scaled bitmap obtained from the images strip file to be drawn on the device screen; personXPos and personYPos are defined as float variables, and their purpose is to account for the x and y coordinates (in pixels) of the top-left point of the rectangular region in the device screen where the frame to be displayed will be placed; whereToDraw is defined as a RectF variable (rectangle delimited by float coordinates), and its purpose is to specify the rectangular region to be selected from the device screen to draw the frame we are dealing with; said rectangular region is delimited by means of the (x,y) coordinates of its top-left point (in this example, (personXPos, personYPos)) and the (x,y) coordinates of its bottom-right point (in this example, (personXPos+ frameWidth, personYPos+frameHeight)); in this particular example of initialization, RectF(personXPos,personYPos, personXPos+frameWidth,personYPos+frameHeight), we are delimiting a rectangular region of dimensions equal to the frame to be displayed, where the top-left point is defined by (personXPos, personYPos), in this case (0,0), thus coinciding with the upper left corner of the device screen.

It is worth noting that although (personXPos, personYPos) coordinates are not changed in the pseudocode presented in the pseudocode, some embodiments may change these values programmatically, thus making the frame displayed on the device screen change its position within the device screen (in other words, the rectangular region defined to hold the frame in the device screen is translated across the screen, since its defining coordinates have been changed by changing (personXPos, personYPos)); the effect of these changes would be the illusion of the person displayed in the frames moving across the screen of the device; this is different from moving (walking, running, etc.) in place, that is, moving in a fixed position in the device screen, as if the person was moving (walking/running, etc.) over a treadmill; some embodiments may choose to translate across the screen some other image bitmap displayed as a background over which the person in our frames is drawn, thus achieving the illusion that the person in our frames is moving across the background image bitmap, even if the person in our frames is moving (walking/running/etc.) in a rectangular region fixed in the device screen; in other words, the background image bitmap is translated across the device screen while the person in our frames moves in place (in a fixed position), thus giving the illusion that the person in our frames is translating across the scene displayed in the background image bitmap; other embodiments may use any variations and/or combinations of any said elements/ changes/strategies and/or any other, including, by way of example without limitation, the translation and/or rotation and/or scaling of the person's image bitmap and/or the background's image bitmap and/or any other image bitmap to achieve any of the effects and/or illusion of animation of any kind (including navigation through virtual environments) and/or any other. Other embodiments may use any other variations and/or combinations of any of said elements/devices/specifications/characteristics/tools/variables/ initializations/methods/approaches/techniques and/or any other tools/library/API, or any other in any fashion and for any purpose, including by way of example without limitation, achieving similar or different and/or variations and/or combinations of any effects described above.

Continuing with the pseudocode, the method manageCurrentFrame( ) may be used to select the appropriate frame in the scaled bitmap of the images strip in order to achieve the illusion of animation (or control of the user's representation, or control of an attribute (e.g. cadence, stride length, velocity, activity, calories burned per time unit, etc.) of the user's representation) to the human eye; in simple words, the illusion of animation can be achieved by quickly displaying ordered and consecutive frames showing static postures of the user's representation; if the frames are displayed fast enough (e.g. frames refreshed with a frequency larger than approximately 12 Hz), they will look as a continuous and smooth transition to the human eye, achieving the effect of animation; in this example of embodiment, we first obtain the current time in milliseconds, and store it in a variable called time; next, if this is the first time accessing this method and we are starting the application (circumstance characterized by beginning_manageCurrentFrame being true, and currentFrame being 0), then we set the origin of time reference (frame_0_StartTime) equal to the previously obtained time, and we set beginning_manageCurrentFrame as false to avoid further changes; next, we obtain timeIntoCompleteAnimation as the difference between the previously determined time and frame_0_StartTime; next, we determine currentFrame as the integer value of (timeIntoCompleteAnimation*frameCount/completeAnimationPeriod) being applied the modulus operand (%) with frameCount (in order to obtain the rest of the division between (timeIntoCompleteAnimation*frameCount/ completeAnimationPeriod) and frameCount); next, frameToDraw.left=currentFrame*frameWidth and frameToDraw.right=frameToDraw.left+frameWidth update the rectangular region borders within the scaled images strip to be drawn; in particular, the left border of said rectangular region is defined multiplying the currentFrame number by the frameWidth, while the right border of said rectangular region is defined as its left border plus frameWidth, the frame width; other embodiments may use any other approaches, and/or software, and/or libraries, and/or APIs, and/or variables, and/or methodologies, and/or any other and/or variations and/or combinations thereof to achieve the same or similar effects.

Continuing with the pseudocode, the method doDraw (Canvas canvas) is mainly used to draw (render) on the device screen; first, the method manageCurrentFrame( ) is called to select the frame (rectangular region) within the scaled images strip to be drawn; next, canvas.drawBitmap performs the drawing or rendering on the device screen (canvas) of the specified rectangular region (frameToDraw) of the scaled images strip bitmap (imagesStrip), scaling/translating automatically to fill the destination rectangle (whereToDraw); it is worth noting that within this doDraw method, additional calls to canvas.drawBitmap can be performed to draw different images (e.g. background images, or images of other elements to be drawn within the device screen, etc. defined in analogous ways to how the imagesStrip bitmap is defined), which can be rendered in different positions (again, modifying the borders or coordinates of delimiting points of their defining rectangular (or other shape) regions), (and/or rendered with different rotations and/or scaling factors) within the device screen, as desired, thus achieving the effect or illusion of different types of movement across the device screen; it is also worth noting that some embodiments may leverage additional software methods implemented by the developer or provided by the device operating system to achieve any of the effects or any other in any fashion, including any variations and/or combinations thereof; by way of example without limitation, some embodiments may leverage Android operating system methods to perform rotations, scaling, translations or any other and/or variations and/or combinations thereof to achieve any effect in any fashion, for instance to achieve an illusion of movement/displacement of a person (e.g. a representation of the device's user) within a virtual environment displayed on the device screen; it is also worth noting that the doDraw method may be triggered (e.g. called within the main Thread) fast enough to achieve illusion of animation to the human eye (typically every 16 milliseconds, or a frequency of 60 Hz, although other frequencies may also be possible); some embodiments may use any variations and/or combinations of any terms/elements/procedures or any other in any fashion.

Continuing with the pseudocode, the method setAnimationImagesStrip(int stripResource) is mainly used to select the images strip file (e.g. extension png) from which its frames are to be drawn on the device screen; the input parameter of this method, stripResource, is an integer to identify the images strip file we want to work with; for sake of simplicity, in this particular example of embodiment, we are assuming 3 images strip files ("firstImagesStripFile.png", "secondImagesStripFile.png", "thirdImagesStripFile.png") stored in the assets folder of the application, and stripResource will take values of 0, 1, and 2 to identify the first, second and third images strip files respectively; in this particular example, we may assume that said images strip files may correspond to FIG. 9A, FIG. 9B, and FIG. 9C respectively. Other embodiments may have a smaller or larger number of images strip files following any criteria including memory management, storage capabilities, design strategies, granularity in the changes of attributes of the representation, and/or any other including any variations and/or combinations thereof; by way of example without limitation, some embodiments may use 6 images strip files, corresponding to FIG. 9A, FIG. 9B, FIG. 9C, FIG. 9D, FIG. 9E, and FIG. 9F or any variation of them; in one embodiment, FIG. 9E and FIG. 9F may have the same number of frames (e.g. 26) as FIG. 9A, FIG. 9B, FIG. 9C, and FIG. 9D for efficient memory management purposes (e.g. to avoid heap memory fragmentation); other embodiments may use a very large number of images strip files, each one of them with the person (or user's representation) whose gait cycle is being displayed presenting, by way of example without limitation, a different value for a gait (or any other type) attribute (or one or more attributes) we may be focusing on; for instance, we could have 21 (or any other number) images strip files of 26 frames each, and each images strip file would present the person performing the gait activity (walk/run/jog or any other type of activity) with a different value (or any characterizer) of attribute(s).

Focusing by way of example without limitation on stride length, it may range for example from 15 inches to 45 inches (these values in inches may correspond to an exemplary user, and to a natural scale representation of a user, but it is obvious that the images strip files show scaled representations of a user, and consequently the stride length values of the person being shown in these images strip files are scaled values of the previously referred ones (e.g. 15 inches to 45 inches could accordingly be scaled down to 15 millimeters to 45 millimeters, or any other values following any criteria including by way of example without limitation, design)), with the first images strip file showing a stride length accordingly scaled to represent a real user's stride length of 15 inches, the second images strip file presenting a stride length accordingly scaled to represent a real user's stride length of 16.5 inches, the third images strip file illustrating a stride length accordingly scaled to represent a real user's stride length of 18 inches, and so on; consequently, we can control (e.g. by selecting the appropriate images strip file (with the appropriate value of attribute) to be rendered on the screen) in real time the stride length of the representation of the device user being displayed on the device screen, and we can replicate the values of stride length of the user with the values of stride length of the representation (obviously accordingly scaled to fit within the device screen), with a granularity (in this example, 1.5 inches) equal to the range in the values of stride length (in this example, 30 inches=45 inches−15 inches) divided by the number of images strip files we have minus 1 (in this example, 20=21−1). By way of example without limitation, the user's representation's stride length (or one or more attributes) may be controlled by setting its value proportional to the value of the user's determined stride length. Analogously, an aspect of an application or process in the device may be controlled by setting its value proportional to the value of the user's determined stride length (e.g. the value of brightness of the screen (and/or any aspect of user interface, settings, etc.) may be set proportionally to the value of the determined stride length), or by triggering/stopping/controlling in any way any procedure/process/application depending on the value of the determined stride length (e.g. if stride length is equal to 20 inches, then trigger (e.g. software activation) an out-loud reader), or in any other way. In some embodiments, the control over the stride length of the representation of the user can be performed with an update frequency larger than the user's step frequency, e.g. performing the selection of the appropriate images strip file (with the appropriate value of attribute (e.g. stride length)) to be rendered on the screen, with an update frequency larger the user's step frequency; some embodiments may achieve this, for example, by calling the setAnimationImagesStrip method with the desired frequency and/or as soon as a new images strip file is needed; for this, some embodiments may call the setAnimationImagesStrip method from within the manageCurrentFrame method (e.g. called from within the doDraw method, which may be typically triggered with a frequency of 60 Hz); other embodiments may choose to call the setAnimationImagesStrip method from outside the manageCurrentFrame method, but within the onSensorChanged method (e.g. may be triggered with a frequency equal to the accelerometer sampling rate, which may be larger than the user's step frequency); other options are also possible; additional details are provided throughout the rest of this application.

It is also interesting to note that the setAnimationImagesStrip method presented in the pseudocode may be modified in some embodiments: for example, the application may create and hold in memory the Bitmaps for each one of the images strip files stored in the assets folder (keeping for example several Bitmap variables, named e.g. imagesStrip1, imagesStrip2, imagesStrip3, etc.) and work directly with these Bitmaps rather than working with a single Bitmap and recycling it and assigning it the information of a new images strip file every time a new images strip file is needed; other embodiments may use any other strategies and/or any variations and/or combinations thereof.

It is worth noting that stripResource (e.g. in the pseudocode) can be easily set programmatically, by way of example without limitation, using "if else" structures leveraging the value of, for example, the determined stride length (e.g. if the determined stride length is equal to (or less than) 15 inches, then stripResource is equal to 0; else, if the determined stride length is equal to (or less than) 16.5 inches, then stripResource is equal to 1; else, if the determined stride length is equal to (or less than) 18 inches, then stripResource is equal to 2; and so on); other embodiments may use alternative approaches, and leverage additional variables to programmatically set the value of stripResource; additional descriptions on this and other topics can be found in the incorporated references.

It is also worth noting that, following any criteria referenced above, or any other, some embodiments may call the setAnimationImagesStrip method within the manageCurrentFrame method (which is called within the doDraw method), achieving an update frequency of the images strip file being displayed equal to the screen refresh rate (typically 60 Hz); additional descriptions on this and other topics can be found in the incorporated references.

It is also worth noting that a single one of the user's determined attributes (e.g. stride length), may control one or more attributes of the user's representation being displayed on the device screen; for example, as described above, the user's determined stride length may control the stride length of the user's representation being displayed on the device screen; this may be achieved in some embodiments by controlling, leveraging the value of determined user's stride length, the selection of an appropriate images strip file where the user's representation has the appropriate value of stride length (e.g. in pseudocode: if (determined_stride_length==value1) {then, images_strip_file="file1.png";} else if (determined_stride_length==value2) {then, images_strip_file="file2.png";} . . . and so on); in some embodiments, said user's representation may change other attributes besides stride length if we compare it with different images strip files; in other words, when we select the appropriate images strip file with the new value of stride length, other attributes in the user's representation may have also changed besides the stride length; for example, looking at FIG. 9A, 9B, 9C, 9D, (or FIG. 10A, 10B, 10C, 10D for more details) we see progressive enlargements in the stride length of the user's representation, but at the same time we also see changes in, by way of example without limitation: the swing of the arms, the vertical displacement of the hips (and the whole upper body), the rotations of the hips on the horizontal plane, the rotations of the shoulders on the horizontal plane, the rotations of the neck (and head) on the forward-backward direction, the angles of the thighs with the vertical direction, etc. Further details may also be appreciated in FIG. 10E, 10F, where, by way of example, the hair of the user's representation is changed (e.g. it bounces with every step), or the angle of the feet at landing on the ground is also changed. Other embodiments may choose to modify or control these and/or any other attributes in any way. Consequently, the determined stride length of the user may control the stride length of the user's representation being displayed on the device screen, and it may also control additional attributes of said representation (even if it is because of indirect reasons); as described in the rest of this application, said control may be performed in real time and with an update frequency larger than the user's step frequency, because for example in some embodiments said control is based on the same principles ruling the control of the user's representation's stride length with the user's stride length.

The same reasoning may be extended to any other attribute of the user, since in some embodiments, a user's determined gait attribute (e.g. cadence, activity, velocity, calories burned per time unit, etc.) may control one or more attributes of the user's representation being displayed on the device screen. By way of example without limitation, the user's representation's cadence (or one or more attributes) may be controlled by setting its value proportional to the value of the user's determined cadence. Analogously, an aspect of an application or process in the device may be controlled by setting its value proportional to the value of the user's determined cadence (e.g. the value of brightness of the screen (and/or any aspect of user interface, settings, etc.) may be set proportionally to the value of the determined cadence), or by triggering/stopping/controlling in any way any procedure/process/application depending on the value of the determined cadence (e.g. if cadence is equal to 2 Hz, then trigger (e.g. software activation) an out-loud reader), or in any other way. For example, as shown in the pseudocode, the user's determined cadence may control the user's representation's cadence in real time and with an update frequency larger than the user's step frequency; additional descriptions on this and other topics can be found in the incorporated references.

Analogous reasoning may be extended to any of the other determined user's gait parameters. By way of example without limitation, the determined user's activity, velocity, calories burned per time unit, and device position, may be leveraged analogously to the way the variable completeAnimationPeriod may be used to control one or more attributes of the user's representation in real time and with an update frequency larger than the user's step frequency, as described in application Ser. No. 16/044,833.

Continuing with the pseudocode, within the setAnimationImagesStrip method, the first line: imagesStrip.recycle( ) is intended to free the memory resources being assigned to the currently used images strip file, because in this example of embodiment we want to assign those memory resources to hold a new different images strip file; it is worth noting that other embodiments may not need this step, but instead use additional memory allocations to handle different images strip files; this decision may depend on the available heap memory for the application, the size of the images strip files being handled, or any other criteria; additional descriptions on this and other topics can be found in the incorporated references.

It is also worth noting that some embodiments may leverage the onSensorChanged method provided by the SensorEventListener interface (used for receiving notifications from the SensorManager when sensor values have changed); the pseudocode shows schematic squeleton pseudocode for the onSensorChanged method for an example of embodiment, which would include this method within the AnimationThread class of the pseudocode; multiple additions and/or variations and/or alternatives and/or combinations thereof are also possible in some embodiments. The "public void onSensorChanged(SensorEvent event)" method is called when sensor values have changed; detailed information on this and other topics can be found online at the android developer website or any other online sources (e.g. https://developer.android.com https://developer.android.com/reference/android/hardware/SensorListener.html); basically, to summarize in simple words, every time the accelerometer, if(event.sensor.getType( )==Sensor.TYPE_ACCELEROMETER), has new measurements, the onSensorChanged method is triggered and the new acceleration values can be read (e.g. double x_acceleration=event.values[0]; double y_acceleration=event.values[1]; double z_acceleration=event.values[2]); some embodiments may use the read acceleration values as inputs for a method that may determine the device user's gait velocity, calories burned per time unit, cadence, and activity (and/or any other gait (or any other type) attribute, such as stride length, and/or any other, and/or any variations and/or combinations thereof, including any number of them (e.g.: velocity, cadence, and activity; or velocity, cadence, activity, and stride length; etc.)) following any of the procedures/methodologies described in this specification or any other and/or any variations and/or combinations thereof; for example, the method determine_gait_parameters(double x_acceleration, double y_acceleration, double z_acceleration, double z_acceleration, double signal_vector_module_acceleration), may return an array of doubles containing the determined gait parameters: e.g. double[ ] gait_parameters=determine_gait_parameters(x_acceleration, y_acceleration, z_acceleration, signal_vector_module_acceleration); by way of example, the method determine_gait_parameters may be called directly from within the onSensorChanged method, thus determining the gait parameters with a frequency equal to the accelerometer sampling rate, which may be larger than the user's step frequency.

Some embodiments may determine (e.g. using the determine_gait_parameters method) only one of the device user's gait attributes (e.g. only velocity, or only cadence, or only activity, or only stride length, or only calories burned per time unit, or any other possibilities), while other embodiments may determine one or more (or any number) of the device user's gait (or any other type) attributes; again, it is worth noting that some embodiments may determine said attributes in real time simultaneously (or nearly simultaneously, e.g. one after the other, but with very small time differences, since some embodiments may determine them all with very high update frequencies (e.g. 60 Hz or higher)); other embodiments may use different approaches and/or variations and/or combinations thereof; for example, some embodiments may hold the read acceleration values in arrays that can be passed as inputs to the determine_gait_parameters method at desired time intervals, thus achieving a desired update frequency for the determination of the gait parameters; other embodiments may use upsampling/downsampling/filtering/or any other techniques to help in the setting of a desired update frequency for the determination of gait parameters; other embodiments may perform storing of acceleration values (e.g. creating a time window of acceleration values) within the determine_gait_parameters method and only trigger the actual determination of parameters when a desired amount of acceleration values (or a desired time interval in a time window) has been reached; other embodiments may use different approaches and/or variations and/or combinations thereof. Some embodiments may use the determine_gait_parameters method to determine any gait parameters or any others leveraging any possible methodology, including by way of example without limitation, the stride length (e.g. stride length equals the gait velocity divided by the gait cadence (or frequency)), the calories burned by the device user (for instance, the relationship between velocity and calories burned has been extensively studied (e.g. "Medicine and Science in Sports and Exercise", 2011, by Ainsworth B E, Haskell W L, Herrmann S D, Meckes N, Bassett Jr D R, Tudor-Locke C, Greer J L, Vezina J, Whitt-Glover M C, Leon A S), and said relationship (e.g. Calories burned per second equal to the user Weight (in Kg) multiplied by MET/3600, where MET is well known (e.g. MET for walking equals 1 plus velocity in mph times 0.7663 if velocity lower than 3.5, or −6.69 plus velocity in mph times 2.642 otherwise)) may be leveraged in some embodiments in order to determine the calories per time unit burned by a mobile device user), or any other (e.g. calories burned by the user equal the calories burned per time unit multiplied by the time under consideration (e.g. time unit=second)). Some embodiments may leverage the determine_gait_parameters method to compute only a few of said gait parameters (e.g. only velocity, cadence and activity), and compute additional parameters (e.g. stride length, calories burned, etc.) in additional methods (or in any other place within the application) leveraging the determined velocity, cadence and activity, in a way that all parameters are determined in real time with an update frequency larger than the user's step frequency; other embodiments may leverage the determine_gait_parameters method to compute all desired parameters (e.g. velocity, calories burned per time unit, cadence, activity and stride length, and any others) directly, also in real time with an update frequency larger than the user's step frequency; some embodiments may leverage any techniques/methodologies (e.g. upsampling, downsampling, filtering of any kind, use of specific time windows (with specific overlapping factors) to hold sensor values before the time window of those sensor values is being processed to determine parameters, and/or any other, and/or any variations and/or combinations thereof) to control the time intervals between determinations of parameters (or to control the determination update frequency), allowing determination in real time with an update frequency larger than the user's step frequency, or lower than the user's step frequency, or any other, following any criteria. Some embodiments may use any variations and/or combinations thereof.

Regarding the activity of the device user, some embodiments may determine it in real time within the determine_gait_parameters method, leveraging the acceleration values (or any sensor values), which may be processed over a desired time window or in any other way, together with other gait parameters already determined within said method (e.g.

velocity, cadence, stride length, calories burned per time unit and/or any others, although some embodiments may not use all or any of these gait parameters), and/or any additional parameters computed making use of any of the previously referred inputs (e.g. mean and/or variance and/or standard deviation and/or skew and/or kurtosis and/or principal frequency component and/or energy in selected frequency bands, and/or any other obtained from acceleration (and/or any other sensor(s) values) signal vector module over a selected time window (e.g. 4 seconds time window), and/or from x, y, z components of acceleration (and/or any other sensor(s) values) over a selected time window (e.g. 4 seconds time window) or any other); in some embodiments all said parameters may be computed in real time within the determine_gait_parameters method, for example after determining the user's velocity, cadence, stride length and calories burned per time unit, and all (or some of them) may be leveraged as features to compute activity by means of a model (in some embodiments it may be a simple formula or a simple structure of conditionals or more complex structures or any other) generated (e.g. offline in a desktop PC, or directly within the device using appropriate software, or any other way and/or variations and/or combinations thereof) using machine learning or any other algorithms/methods and training data previously gathered from volunteers replicating/performing the range of activities (and/or any gait characteristics/attributes (e.g. velocity, cadence, stride length, calories burned per time unit, etc.) and/or any other such as the position of the device) we try to recognize using the device while their data on acceleration (and/or any other sensor(s) values), the type of activity (and/or values of gait attributes such as velocity, cadence, stride length, calories burned per time unit, device position, etc.) and any other parameters (including the features) are being recorded to create a training set; by way of example without limitation, any of the available software packages (e.g. MATLAB and Toolboxes, python and modules, weka, etc.) may be leveraged for modeling purposes (e.g. the model may be obtained leveraging the training set and using support vector machine, Naive Bayes, k-nearest neighbors, decision trees, random forests, logistic regression, linear regression or any other method/algorithm and/or any variations and/or combinations thereof, depending on criteria including without limitation: type and number of activities (and/or gait attributes and/or others) we try to recognize, accuracy, complexity, qualities of training set, and/or any other); an example of embodiment may use support vector machine to recognize between walking (e.g. coded with value 0) and running (e.g. coded with value 1), while other embodiments may use any alternative methods (and recognize any other activities, e.g. walking, jogging, jumping, cooking, household activities, running, cycling, driving, or any other), and some embodiments may leverage as features to determine activity and/or any gait attribute (e.g. velocity, stride length, cadence, calories burned per time unit, device position, and/or any other): 1) the user's velocity and the user's cadence, or 2) the user's velocity and the user's cadence and the mean, standard deviation, principal frequency component and energy in selected frequency bands of the acceleration (and/or any other sensor(s) values, and again, taken as x, y, z components and/or signal vector module) over a desired time window, or 3) the user's velocity and the user's cadence and the mean, variance, standard deviation, skew, kurtosis, principal frequency component and energy in selected frequency bands of the acceleration (and/or any other sensor(s) values, and again, taken as x, y, z components and/or signal vector module) over a desired time window, or 4) the mean, variance, standard deviation, skew, kurtosis, principal frequency component and energy in selected frequency bands of the acceleration (and/or any other sensor(s) values, and again, taken as x, y, z components and/or signal vector module) over a desired time window, or 5) any or all of the previous features and/or any other additional ones, and/or any variations and/or combinations thereof. In some embodiments any or all of said features may be determined in real time with an update frequency larger than the user's step frequency, and leveraging said features the user's activity (and/or any gait attribute (e.g. velocity, stride length, cadence, calories burned per time unit, device position, and/or any other)) may be determined in real time with an update frequency larger than the user's step frequency. In some embodiments, the determined user's activity may be used to control the activity of the user's representation on the device screen in real time with an update frequency larger than the user's step frequency: by way of example, by selecting an appropriate images strip file whose frames are to be displayed on the device screen (e.g., if activity is "walking" (e.g. coded as 1), then the images strip file may be any of FIG. 9A, 9B, 9C, 9D or any other representing a walking activity; or if the activity is "running" (e.g. coded as 2), then the images strip file may be any of FIG. 9E, 9F, or any other representing a running activity, etc.).

By way of example without limitation, some embodiments may employ the same (or similar) procedure described above for the determination of activity, to determine in real time and with an update frequency larger than the user's step frequency, the velocity (and/or cadence an/or calories burned per time unit and/or stride length and/or device position and/or any other attribute) of the user, as described in application Ser. No. 16/044,833.

It is interesting to note that the last block of 8 lines in the pseudocode summarizes the way some embodiments may handle the change in the user's cadence through the variable completeAnimationPeriod, which may be used to select the appropriate frame from the appropriate images strip file to be displayed on the device screen to adequately control the cadence of the user's representation on the device screen (as shown for example in the manageCurrentFrame method defined in the pseudocode); additional descriptions on this and other topics can be found in the incorporated references.

Again, some embodiments may use any variations and/or modifications and/or combinations of any said elements, concepts, procedures, methods, or any other additional ones, in any fashion. Definitions and/or further details for each one of the concepts, terms, etc. can be found online (e.g. https://developer.android.com or any other website).

Figure 11:
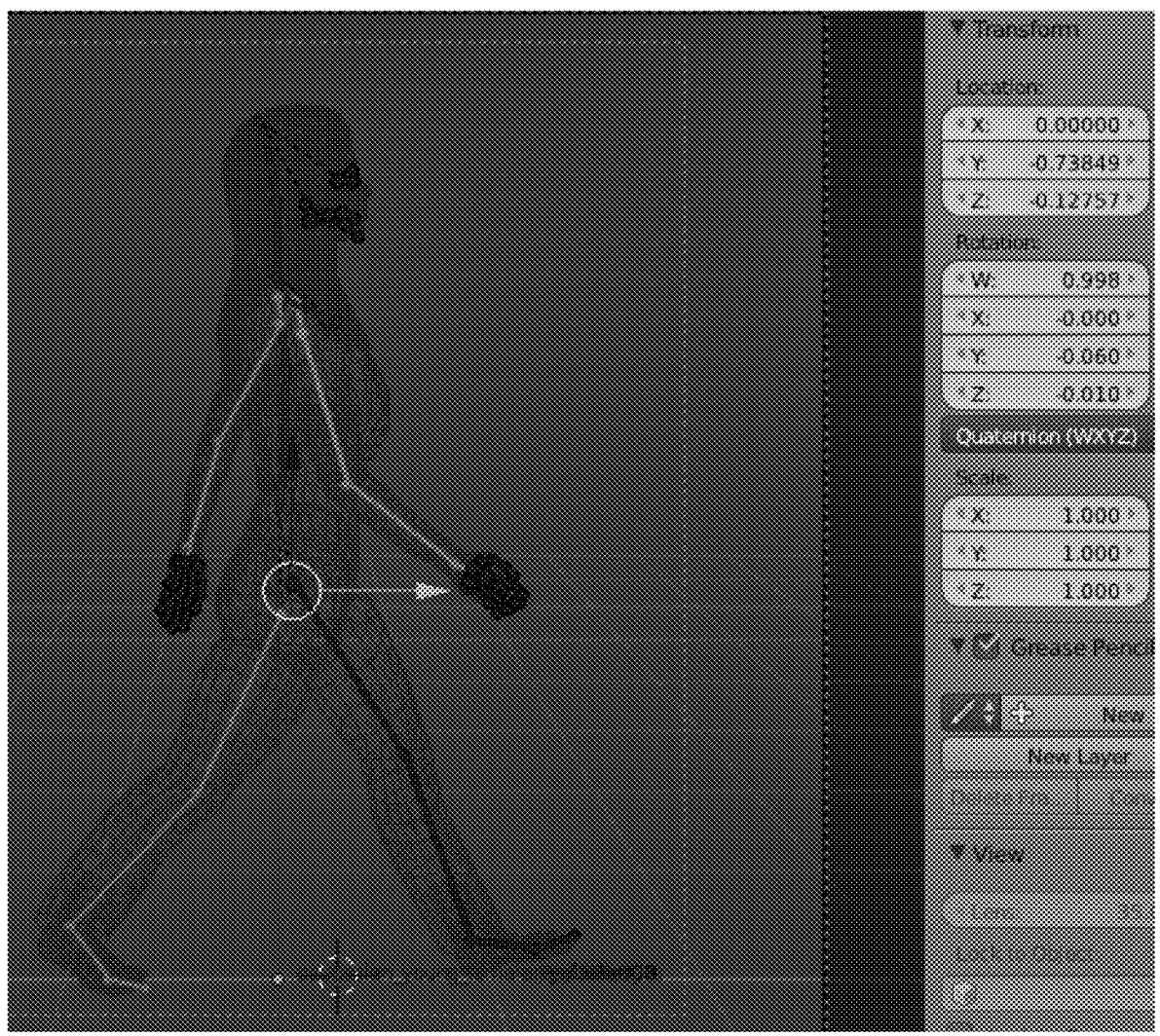
FIG. 11 illustrates part of the user interface of the open-source 3D computer graphics software Blender used in one embodiment.
Figure 12:
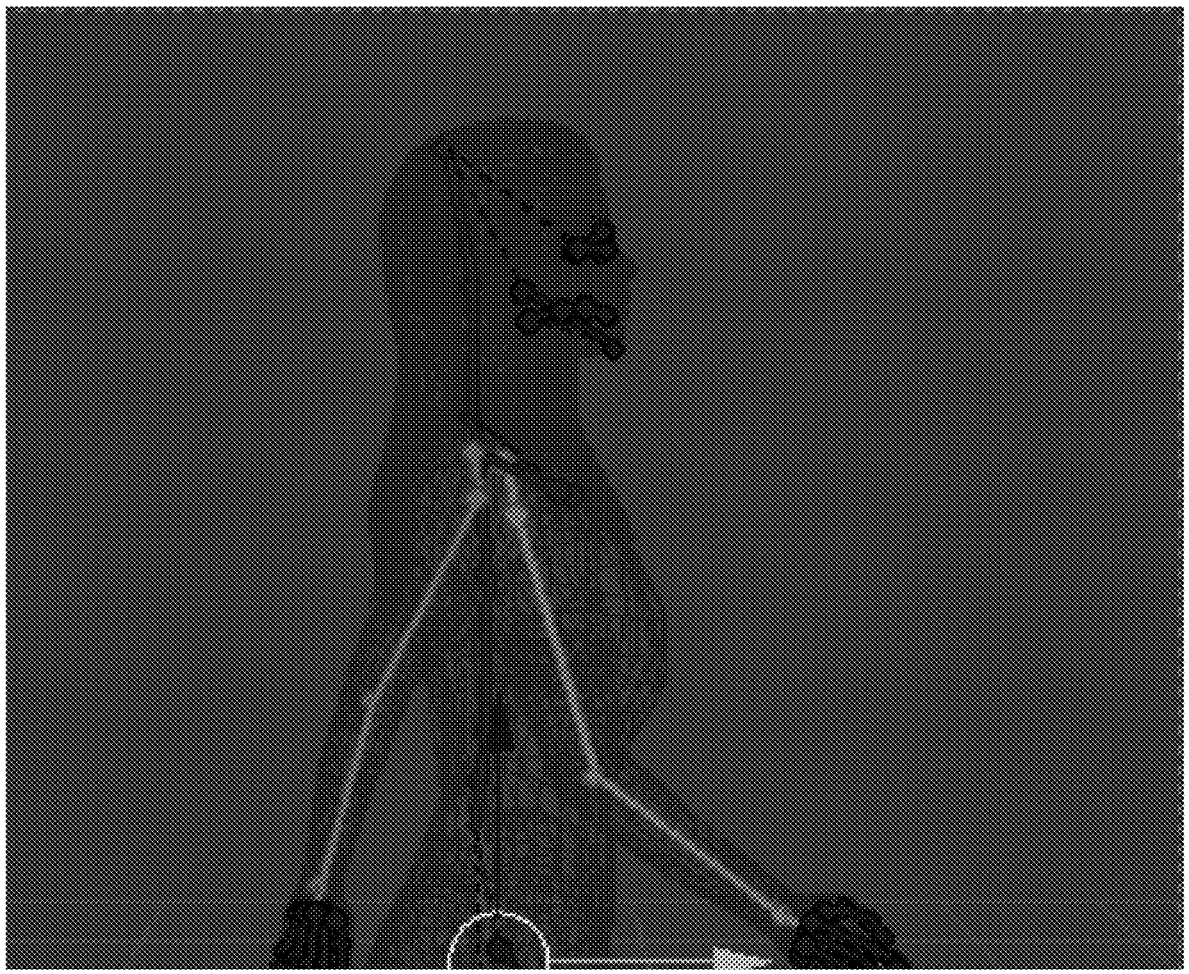
FIGS. 12 and 13 provide higher details of the same.
Figure 13:
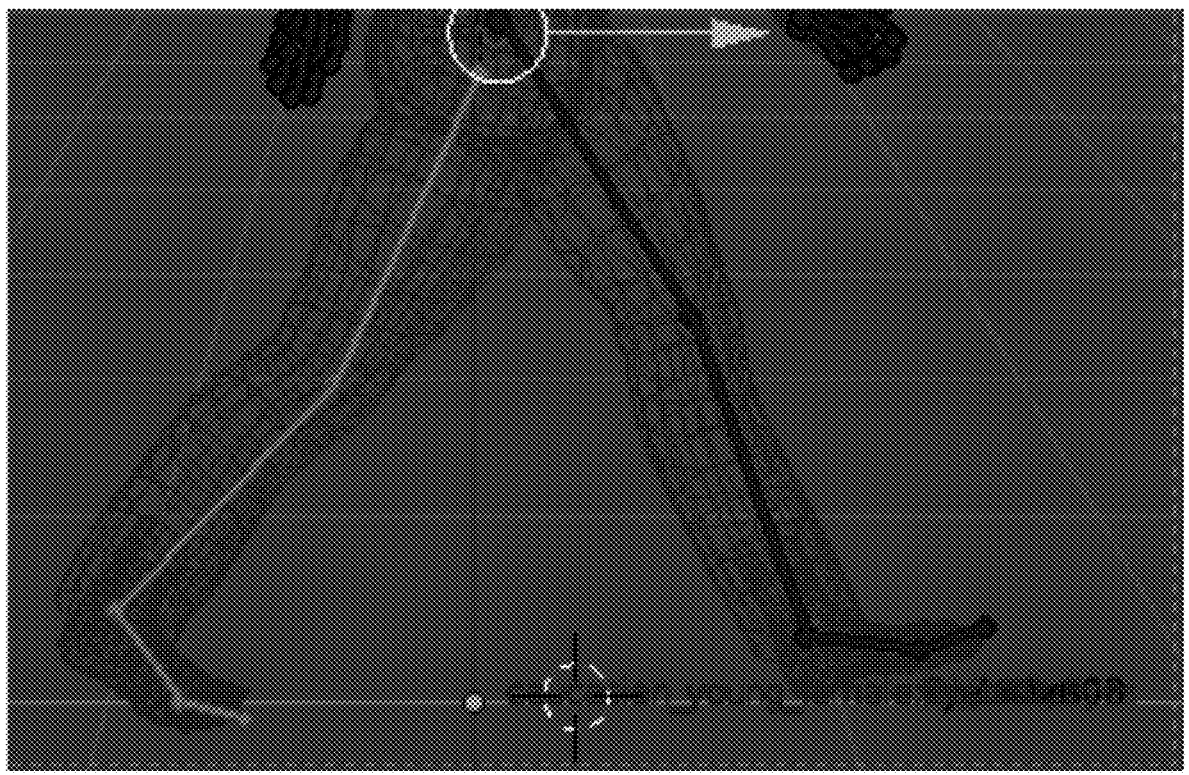

FIG. 11 shows a screenshot of part of the Blender software's user interface that may be used in some embodiments. Blender is a professional, free and open-source 3D computer graphics software toolset used for creating animated films, visual effects, art, 3D printed models, interactive 3D applications and video games. Additional descriptions on this and other topics can be found in the incorporated references.

Some embodiments may use any type of smartphones, mobile devices, wearable devices and/or sensors, or any other types of devices or combinations of them, including but not limited to, personal digital assistants, personal navigation systems, portable electronic devices, tablets, laptops, computers, and their peripheral devices. In some embodiments, the definition of mobile device may comprise any type of mobile phone, smartphone, wearable device and/or sensor, or any other types of device or wearable or combinations of them.

Some embodiments may use combinations of strategies and techniques, including, by way of example, and not limitation, machine learning techniques, probabilistic models, sensor fusion techniques, extraction of statistics, employment of filter banks, application of dimensionality reduction techniques, a variety of approaches for classification, etc. Details are omitted to improve the clarity of the description. In addition, some embodiments may use a variety of programming languages and methodologies in combination with varied hardware configurations and execution strategies.

Applications of some embodiments may comprise monitoring a variety of information of people in a variety of circumstances or contexts, including but not limited to, health-care, army, sports, etc., as described in application Ser. No. 16/044,833.

Efficient Management of Large Amounts of Data Related to Gait:

Sensors in mobile or wearable devices provide an opportunity to monitor user's data (including gait data, activity data, fitness data, health data, etc.). Existing methods and/or applications (e.g. fitness applications for mobile devices such as smartphones) generally display aggregate data for the user to have only a global look at his/her activities. For example, it is common practice among mobile applications in the fitness and/or health art, to display the total amount of steps taken by the user over a whole day, or display only a few bars indicating the total number of steps taken by the user during each one of the 24 hours of a day. Other gait attributes such as calories burned, speed, distance, etc. are treated similarly by existing mobile applications, in such a way that the user can only see data with a very low resolution or granularity (typically time intervals of 1 day or 1 hour). This very low resolution in the data presented to the user is a problem for many technical fields and for many potential new applications. For example, many users would like to see the variation of their data (e.g. a gait attribute such as speed, calories burned per hour, cadence, stride or step length, etc.) with a high resolution; for instance, athletes would be able to improve their running techniques by knowing how particular events or circumstances during their workouts affect their gait attributes; by way of example without limitation, an athlete would be very interested in knowing how his/her speed, cadence, calories burned per time unit, step length, etc. changed during the first 15 seconds of minute 5 of his/her race, during which he/she was going through a ground with grass rather than concrete, for example to know if he/she needs to avoid the ground with grass in order to improve his/her performance in a long distance race; or it could be useful for an athlete to know how his/her speed, cadence, calories burned per time unit, step length, etc. changed during the first 10 seconds of minute 0 of his/her race, until he/she stabilized his/her pace, in order to improve his/her performance in medium range races; or it could be useful for an athlete (sprinter) to visualize how his/her speed, cadence, calories burned per time unit, step length, etc. changed every 0.25 seconds for the 11 seconds of his/her race in order to improve his/her performance (e.g. trying to strengthen a weak point in his performance, like e.g. trying to focus on increasing stride length at the very start of his/her race). In a similar sense, a doctor or a patient looking at fitness data would find it useful to have more information than just the total number of steps taken by the user over a whole day; for instance, a doctor or a patient would find it useful to be able to see the variability of the user's gait attributes with a high resolution in time (e.g. being able to see how the gait attributes change every second, or every half of a second (or less)) in order to help diagnose potential medical conditions associated to gait variability; for example, certain medical conditions are known to increase the variability of the gait attributes of the user; in order to help diagnose, and/or monitor and/or treat said conditions, there is a need to determine gait attributes with high time resolution, and present the determined data to the user and/or doctor and/or relatives with a high time resolution (e.g. a data point corresponding to a gait attribute for every half of a second (or less, e.g. approximately every quarter of a second)). Existing mobile applications lack a high time resolution in the data presented to the user; the reasons for this may include the fact that existing applications determine gait data with low time resolution, and the fact that mobile devices are constrained in size, posing a difficulty to present large amounts of data in a simple way; another reason for the lack of resolution in the data displayed to the user may be the lack of accurate methodologies being applied in existing mobile applications to determine gait attributes at a relatively high update frequency (as emphasized in this patent application, determining a gait attribute with an update frequency larger than e.g. 2 Hz can improve the accuracy of the determination (e.g. using the context of recently determined data can help in accurately determining new data by relying on the known data for cases in which there may be a doubt in the solution)); for example, it is common practice among existing mobile applications to present to the user the total number of steps taken through the day as a number, or as a histogram containing 24 bars, one bar for each hour of the day (thus the time resolution of existing mobile applications is 1 hour or 1 day, which is not enough to enable potential applications such as the examples above). To solve these problems, this patent application introduces novel techniques to determine gait attributes with high time resolution (e.g. with an update frequency greater than 2 Hz, or with an update frequency greater than the user's step frequency, or with an update frequency greater than a threshold of e.g. 0.2 Hz (for instance, 0.25 Hz, and/or 0.5 Hz, and/or 1 Hz, and/or 2 Hz, and/or 4 Hz, and/or 8 Hz, and/or 16 Hz, etc.) and lower than another threshold of e.g. 190 Hz, and/or 400 Hz, and/or 1000 Hz, while some embodiments may use any other values of thresholds and/or any values in between, and/or any variations and/or combinations thereof), bringing the additional improvement of enhanced dynamism in the solution, and thus enhanced user experience, and consequently bringing improvements to numerous technical fields as explained in the current disclosure (this Specification and references)), and to efficiently store the increased amounts of generated data without posing a burden to the user and/or his/her mobile device, and to create useful images to be displayed in the mobile or wearable device in order to present the data (increased amounts of data, since the time resolution will be higher than the time resolution currently offered by existing applications) to the user in an easy to understand way, and efficiently leveraging the constrained sizes of mobile or wearable devices. Consequently, the claimed inventions of this patent application provide improvements to numerous technologies or technical fields. These improvements are also emphasized throughout the rest of this patent application.

In some embodiments, the disclosure relates to systems and processes for monitoring attributes (or gait characteristics) of a user's physical activity or inactivity, and for generating user interfaces for displaying the same. One example user interface can include multiple indicators that represents an attribute and/or attributes of a user's physical activity. Some embodiments also relate to systems and processes for monitoring a user's workout, and for generating user interfaces for displaying the same. In some embodiments, an electronic device that includes a display and a touch-sensitive surface is used. It should be understood, however, that the electronic device optionally includes one or more other physical user-interface devices, such as a physical keyboard, a mouse, and/or a joystick. The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a health-monitoring application, a steps-counting application, a digital music player application, and/or a digital video player application. The various applications that are executed on the device optionally use at least one common physical user-interface device, such as a touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user. A touch-sensitive display is sometimes called a "touch screen" for convenience and is sometimes known as or called a "touch-sensitive display system." A touch-sensitive display in some embodiments of touch screen is, optionally, analogous to the multi-touch sensitive touchpads described in the following U.S. Patents: U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. In some embodiments, a touch screen may display visual output from the device, whereas touch-sensitive touchpads do not provide visual output. A touch-sensitive display in some embodiments of the touch screen may be as described in the following applications: (1) U.S. patent application Ser. No. 11/381,313, "Multipoint Touch Surface Controller," filed May 12, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety. In some embodiments, a touch screen may optionally have a video resolution in excess of 100 dpi. In some embodiments, the touch screen has a video resolution of approximately 160 dpi. The user optionally makes contact with touch screen using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user. In some embodiments, a graphics module may include various known software components for rendering and displaying graphics on a touch screen or other display, including components for changing the visual impact (e.g., brightness, transparency, saturation, contrast, or other visual property) of graphics that are displayed. In some embodiments, graphics includes any object that can be displayed to a user, including, without limitation, text, web pages, icons (such as user-interface objects including soft keys), digital images, videos, animations, and the like. In some embodiments, a graphics module may store data representing graphics to be used. Each graphic is, optionally, assigned a corresponding code. A graphics module may receive, from applications etc., one or more codes specifying graphics to be displayed along with, if necessary, coordinate data and other graphic property data, and then generates screen image data to output to display controller. In some embodiments, in conjunction with a touch screen, a display controller, a contact/motion module, a graphics module, an audio circuitry, a speaker, an RF circuitry, a text input module, an e-mail client module, and browser module, online video module includes instructions that allow the user to access, browse, receive (e.g., by streaming and/or download), play back (e.g., on the touch screen or on an external, connected display via an external port), send an e-mail with a link to a particular online video, and otherwise manage online videos in one or more file formats, such as H.264. In some embodiments, instant messaging module, rather than e-mail client module, is used to send a link to a particular online video. Additional description of online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety. Exemplary descriptions regarding user interfaces can be found at least in U.S. patent application Ser. No. 14/839,916, "Physical activity and workout monitor," filed Aug. 28, 2015, which is hereby incorporated by reference in its entirety. An important number of world population suffers from health conditions that can be attributed to a sedentary lifestyle. For example, lack of physical activity can increase the risk of developing certain medical conditions, obesity, and health problems. An interface displaying useful images showing the user's activity can be used to easily track the inactivity of the user and prompt users to be active. A user interface can include one or more visual representations of a user's gait activity, and can also include numerical representations comprising a length of time that the user has been active, as measured by a timer of the device. Any other variations and/or combinations are also possible in some embodiments.

Some embodiments may determine a gait attribute (or a gait related information, or a gait characteristic) of the user (e.g. calories burned per time unit (e.g. per hour), and/or velocity, and/or cadence, and/or stride (or step) length, and/or any other(s) mentioned in any of the referred patent applications) using any of the techniques and/or methodologies described in this or any of the referred patent applications, with an update frequency larger than a threshold; by way of example without limitation, the update frequency of determining the gait attribute may be greater than 2 Hz, or greater than 3 Hz, or greater than 4 Hz, or greater than the user's step frequency; typical examples of values of the update frequency for the current disclosure can be e.g. 0.2 Hz, 0.25 Hz, 0.5 Hz, 1 Hz, 2 Hz, 2.5 Hz, 3 Hz, 4 Hz, 5 Hz, 6.5 Hz, 8.1 Hz, 9.6 Hz, 12 Hz, 20 Hz, 30 Hz, 60 Hz, 120 Hz, or even larger (this will depend on the particular hardware capabilities of the mobile or wearable device, but it could be possible to have e.g. an accelerometer sampled at 190 Hz, and determine the gait attribute (e.g. velocity) at every determined accelerometer sample, thus achieving an update frequency for the gait attribute of 190 Hz). Some embodiments may determine the gait attribute(s) with an update frequency larger than any of said thresholds, but less than the device accelerometer's sampling rate (e.g. larger than 2 Hz, but less than e.g. 190 Hz if that is the accelerometer's sampling rate). Other embodiments may use any variations and/or combinations thereof. These determination update frequencies may be larger than the frequencies used in traditional approaches (e.g. traditional approaches delivering e.g. calories burned by the user, with a time resolution of e.g. 1 hour, may not need to determine said calories with a high update frequency), and provide an improvement to numerous technologies or technical fields (e.g. increase the resolution of the delivered solution, enable a more dynamic presentation of a solution in real time (e.g. a new data point may be shown to the user faster than traditional approaches which use lower update rates), enable a better user experience (e.g. faster and more dynamic and more accurate updates of data, in comparison with traditional/conventional approaches which provide slow and commonly erroneous updates of data), and enable a more accurate determination of the gait attribute because we can leverage the previously determined solution to resolve cases with doubt, because the close proximity in time of the previous solution can help enhance the contextual information about the instant time (e.g. if we are obtaining a doubtful solution at the instant time, we can rely on the previous solution to decide whether to support the doubtful solution or not)).

Some embodiments may determine, over a period of time, a first set of a first amount of values of a gait attribute. By way of example without limitation, a user of the mobile or wearable device may walk and/or run and/or perform any other activity for a period of time of e.g. 10 seconds (a sprint race), and/or 1 minute, and/or 5 minutes, and/or 50 minutes, and/or 90 minutes, and/or 2 hours, and/or 3 hours; in some embodiments, the user is performing a gait activity (or different gait activities such as walking, running, walking again, jogging for a few minutes, walking again, etc.) continuously over said period of time; in other embodiments, the user may rest in between activities, so the considered period of time will only include the periods of time in which the user is active; in other embodiments, the period of time will include periods in which the user is not performing a gait activity (e.g. resting); in other embodiments, the period of time will span long periods of activity and/or inactivity (e.g. the period of time may span several hours, or a whole day, or several days, weeks, months, etc.). Other embodiments may use any variations and/or combinations thereof. Some embodiments may leverage the capabilities of the mobile or wearable device to determine the user's gait attribute (e.g. velocity and/or cadence and/or calories burned per time unit and/or stride (or step) length (it is interesting to note that in some embodiments, step length and stride length may be considered synonyms, while in other embodiments a stride will consist of 2 steps (both uses have been commonly accepted by several authors)), and/or any other(s)) over said period of time. In some embodiments, as a result of determining the gait attribute in real time (e.g. by the device) over said period of time, the device may keep storing the determined values of the gait attribute(s) (e.g. using any of the well known data structures such as arrays, lists, etc.) in a memory of the device (e.g. internal memory or external memory such as SD card (e.g. using a file to store values)). By way of example without limitation, In some embodiments, the values of the gait attribute (e.g. gait cadence of the user) being determined in real time by the device, are stored in an array (e.g. an array of doubles in Java; please see any of the programming references incorporated by reference in this or any of the referred applications for detailed descriptions of programming concepts; e.g. https://developer.android.com, "Multithreaded Programming with Java Technology" by Bil Lewis, Prentice Hall, 2000, or "Taming Java Threads" by Allen Holub, Apress, Jun. 1, 2000, or "Multithreading Programming Techniques" by S. Prasad, McGraw-Hill, 1996, or "The art of multiprocessor programming" by Herlihy, Maurice, and Nir Shavit. Morgan Kaufmann, 2011, all of which are incorporated by reference for all purposes). In other words, in some embodiments, after a period of time determining the gait attribute in real time, the device is keeping a first set of values of the gait attribute; we can call the amount of values of said first set as first amount; for example, if the device is determining the gait attribute with an update frequency of 3 Hz, and the period of time is 1 hour, the number of values of the gait attribute determined over said 1 hour is 3600 seconds*3 values per second=10800 values; in other words, we have determined, over a period of 1 hour, a first set of a first amount of values of the gait attribute, wherein the first amount is 10800. Obviously, different embodiments may use different periods of time, different update frequencies, different attributes, etc. (e.g. an embodiment may simultaneously determine several gait attributes (e.g. calories burned per hour, velocity, cadence, and step length) and keep the values of said attributes in different arrays, one array for each attribute); other embodiments may use any variations and/or combinations thereof.

Some embodiments may decide to efficiently store said first set of a first amount of values of the gait attribute; by way of example without limitation, some embodiments may decide to create a second set of a second amount of values using the first set, wherein the second amount is a fixed quantity that is used for different so called "first sets"; in other words, regardless of the size of the first set (or regardless of the first amount, which depends on the length of the time period used for determining the gait attribute, and thus will be variable depending on how long the user decides to remain active), some embodiments may decide to store (and/or manage in any way) any of those "first sets", with a fixed size (fixed second amount of values); this will be helpful to prevent well-known memory segmentation problems (due to the use of blocks of memory of different sizes) that could lead to "out of memory errors" under certain circumstances (e.g. low memory conditions); for example, traditional approaches commonly obtain the amounts of data generated by the user, and store them in the device, requesting more memory resources from the device when the amount of data generated by the user increases; consequently, traditional approaches commonly use blocks of memory in the device with different sizes (depending, for example, on the length of time the user has been performing an activity) to store different activities; this is a problematic and inefficient way of using the memory resources of the device, because for example, if a block of 4 KB of memory used to store an activity is released (e.g. the user deletes that activity), and the next block of data generated by the user in a new activity is e.g. 5 KB, the previous 4 KB may remain unused; in other words, the new block of data doesn't fit into the existing available memory space, so the existing available memory space remains unused and a new block of memory is used to store the next 5 KB of data; over time, the memory of the device may be full of available but unused small chunks of memory in between other used chunks of memory; in other words, the memory of the device is not used efficiently, thus requesting larger amounts of memory than really needed, and leading to a faster exhaustion of the total available memory of the device; since the total available memory of the device is shared among the different applications running in the device, traditional approaches without taking care of memory segmentation issues deliver an inferior user experience and also negatively affect the performance of other applications in the device sharing the same memory resources (more details in memory segmentation issues and out-of-memory errors can be found online, and/or in "Advanced Topics in Types and Programming Languages" by Benjamin Pierce, MIT Press (2005), and/or "Garbage Collection: Algorithms for Automated Dynamic Memory Management" by Richard Jones and Rafael Lins, Wiley and Sons (1996), all of which are hereby incorporated by reference for all purposes); the current disclosure solves these issues by using a fixed amount (second amount) of values, which will occupy a fixed amount of memory, in such a way that if a block of memory is released (e.g. a user deleting data related to an activity), when a new block of memory needs to be stored, the empty space can be re-used because the size of the released block of memory equals the size of the newly requested block of memory; this brings a significant improvement in the management of the memory of a mobile or wearable device, translating into higher efficiency and performance of e.g. a health-monitoring application using this approach, and translating into higher efficiency and performance of the rest of applications in the mobile or wearable device which share the same memory resources; in other words, storing data in blocks of the same size provides improvements in memory management within the mobile or wearable device by enabling the reuse of said blocks of known size (e.g. if any of the second sets of known size is discarded, the block of memory released by said discarded second set can be used by a new set that needs to be stored); in other words, some embodiments may decide to create a second set of a second amount (fixed amount) of values using the first set, which will provide improvements in memory management in the mobile device, and help any of the applications running on the mobile device to have a better performance due to the efficient management of the memory of the device. By way of example without limitation, some embodiments may decide to use a "second amount of values" of e.g. 4000 values; the problem to solve now is fitting the first amount (10800 values in the previous example) into 4000 values; different techniques can be used for that, including downsampling by a rational factor, e.g. 10800/4000, (other embodiments may need upsampling by a rational factor, depending on the values of "first amount" and "second amount") as described for example in: Poularikas, Alexander D. (September 1998), Handbook of Formulas and Tables for Signal Processing (1 ed.), CRC Press; Mitra, Sanjit Kumar, and Yonghong Kuo. Digital signal processing: a computer-based approach. New York: McGraw-Hill, 2006; Milić, Ljiljana (2009). Multirate Filtering for Digital Signal Processing. N.Y.: Hershey, all incorporated by reference herein in their entirety for all purposes. As described in said references, downsampling (or upsampling) by a rational factor may comprise an interpolation (e.g. downsampling by a factor of B/A may be performed by: upsampling (interpolation) by a factor of A, and downsampling (or decimating) by a factor of B); on the other hand, if upsampling by a rational factor (e.g. A/B) is required, it may be achieved by: upsampling (interpolation) by a factor of A, and downsampling by a factor of B. Other embodiments may use any variations and/or combinations thereof; in other words, some embodiments may process the first set (using an interpolation on the first set), in order to obtain a second set of a second amount of values. Please note that the concepts of interpolation, downsampling, upsampling, and any of the other possible approaches that may use an interpolation on the first set to obtain the second set, are well-known in the art, and described in the incorporated references. In the same sense, some embodiments may (alternatively and/or in conjunction) use any other well-known technique and/or approach to create a second set of a second amount of values using the first set (e.g. filling in values into the second set, and/or discarding values from the first set, and/or downsampling, and/or upsampling, and/or resampling, and/or any filtering, and/or any other(s) described in any of the incorporated references, and/or any variation and/or combinations thereof). In some embodiments, interpolation refers to any operation(s) needed to obtain, from a first set of a "first amount" of values, a second set of a "second amount" of values, regardless of "first amount" and "second amount".

It is important to emphasize that in some embodiments, the approach described in the current disclosure, providing efficient memory management (e.g. avoiding memory segmentation problems), brings improvements not only to the functioning of the mobile and/or wearable device in which this approach is implemented (at least because the memory resources of the device are used in a more efficient way in comparison with other traditional approaches), but also to numerous other technical fields that may, for instance, use a mobile and/or wearable device to e.g. install and/or manage and/or deliver and/or control an application (e.g. a health-monitoring application, and/or a steps-counting application, and/or a sports activity monitoring application, and/or a game application, and/or an application displaying a virtual environment, and/or any other and/or any variations and/or combinations thereof), wherein the application will run smoothly and efficiently at least in terms of memory thanks to the approach described in the current disclosure, thus improving the user experience, and even the performance of the application (e.g. it is well known that poor memory management can lead to e.g. out-of-memory errors which can terminate an application running in a mobile device, and/or lead to performance errors in the application due to poor memory conditions in the device); additionally, the approach described in the current disclosure brings improvements to numerous other technical fields by e.g. enabling new applications which would not be able to run smoothly without an efficient management of the memory of the device (e.g. any new application which requires a lot of memory from the device in order to be able to run with a minimum level of smoothness and/or performance), and also helping other applications already installed in the device and which share memory with e.g. our new application, since the memory available to be shared among all the applications installed in the device will be efficiently managed (at least regarding our new application).

In some embodiments, the "second amount" of the second set may be chosen as a value greater than 3000, and wherein the mobile or wearable device is a smartphone; the chosen value of "second amount" as larger than 3000 (including, by way of example without limitation 4000, 10000, 36000, 50000, 100000, 500000, 1 million, or even up to a few millions (e.g. the total amount of pixels of a screen of a smartphone), and any value in between, and/or greater than 3000 and less than 2 million, and/or greater than 3000 and less than 1 million, and/or greater than 3000 and less than 500000, and/or greater than 3000 and less than 100000, and/or any other intervals and/or any variations and/or combinations thereof), has at least the functionality of making sure that the amount of points (please remember that there is a relationship between the points of the second set and the measurements of a gait characteristic of the first set, and that there is a relationship between the points of the second set and the pixels of the screen of the device (e.g. said pixels may display the colors represented by the points (values) of the second set)) we deal with in the second set is large enough to provide a high time resolution (e.g. a few seconds or less (e.g. approximately 2 seconds, or 1 second, or 0.5 seconds, or 0.25 seconds)) when displaying the colors related to the measurements of the gait characteristic; in other words, we want to make sure that, in opposition to traditional approaches which offer a time resolution of 1 hour or 1 day for the measured gait characteristic (e.g. calories burned or steps taken), our approach offers a time resolution of a few seconds or less for the measured gait characteristic (e.g. calories burned (including e.g. calories burned per hour) and/or velocity and/or step length and/or step frequency (cadence)); by way of example without limitation, for an activity such as walking performed during approximately 60 minutes, traditional approaches commonly offer a single figure (e.g. total calories burned=190 Cal, or total steps=6200); in contrast, our approach may e.g. determine gait characteristics (including e.g. calories burned per hour, and/or velocity, and/or step length, and/or frequency (or step frequency or cadence)), with an update frequency e.g. greater than e.g. 3 Hz (e.g. update frequency of 3.6 Hz, or 4.5 Hz, or 7.9 Hz, or 10 Hz, or 20 Hz, or 190 Hz, or any value in between) in order to obtain the first set of the first amount; for example, determining measurements for 1 hour at 3 Hz, would deliver 3600*3=10800 measurements (with time resolution of approximately 0.333 seconds); an interpolation of those 10800 values into a "second amount" of e.g. 10000 (or 3600, or 4000, or other values of "second amount" greater than 3000) for the second set would still maintain a high time resolution (e.g. a few seconds or less as mentioned above) at the time of displaying the colors related to the measurements of the gait characteristic (please remember the relationship between the colors from the second set and the measurements of the first set); consequently, our approach ensures that, by choosing a value of "second amount" greater than 3000, the time resolution provided for the gait characteristic is very high (e.g. a few seconds or less), even if the activity of the user spans for many minutes (e.g. 60 minutes or more), while traditional approaches offer a time resolution of 1 hour of 1 day. In other words, in some embodiments, the chosen value of "second amount" as larger than 3000, has at least the functionality of making sure that the time resolution provided for the presentation of the measurements of the gait characteristic is very close to the time intervals chosen to update the measurements of the gait characteristic (e.g. if the update frequency of the gait characteristic is 3 Hz, the time interval chosen to update the measurements of the gait characteristic is approximately 0.333 seconds); this has the additional improvement of minimizing distortions or inaccuracies at the time of presenting the data (ideally, the presented data would have a minimum distortion (e.g. distortion from the interpolation, which e.g. may need approximations for the second set, unless the first amount and the second amount coincide) with respect to the original raw measurement when the time resolution of the presented data coincides with the time resolution of the determining of the measurements, in such a way that the processing of the raw measurements is minimized in order to present (or display) the data); please note that in some embodiments, the closer the "time resolution provided for the presentation of the measurements of the gait characteristic" is to "the time intervals chosen to update the measurements of the gait characteristic", the lower the distortion (at least distortion from the interpolation). By way of example without limitation, some embodiments of our approach choose a value of "second amount" larger than 3000 (and up to the number of pixels of the screen of the mobile or wearable device), for instance 10000, which makes the "time resolution provided for the presentation of the measurements of the gait characteristic" to be close to "the time intervals chosen to update the measurements of the gait characteristic", at least when considering typical healthy activities (e.g. spanning many minutes (e.g. 60 minutes or more)), at least for embodiments in which the update frequency of the determining of the gait characteristic is approximately 1 Hz or higher (or a few tens of Hz (e.g. 0.2 Hz, 0.3 Hz, 0.5 Hz) or higher in other embodiments, or greater than the user's step frequency in other embodiments), e.g. 2 Hz, 3 Hz, 4 Hz, 5 Hz, 10 Hz, 20 Hz, or even 190 Hz or any value in between. Please note that in some embodiments, the value of "second amount" may be chosen between 3000 and 1 million, e.g. 500000, or between 3000 and the total number of pixels in the screen of the device, or any value between 3000 and 500000, or any value between 3000 and any other value larger than 3000 and less than 1 million (at least to optimize performance at the time of computing and displaying the "second amount" of the second set, so that we can manage amounts below approximately 1 million points, since managing 1 million points could impose an important computational burden for some mobile devices).

Next, some embodiments may decide to store the obtained second set of the second amount of values using techniques that improve memory management even more; for example, the following references: Banerjee, Sudipto; Roy, Anindya (2014), Linear Algebra and Matrix Analysis for Statistics, Texts in Statistical Science (1st ed.), Chapman and Hall/CRC; Horn, Roger A.; Johnson, Charles R. (1985)., Matrix Analysis. Cambridge University Press; Horn, Roger A.; Johnson, Charles R. (1991). Topics in Matrix Analysis. Cambridge University Press; Simon, C.; Blume, L. (1994). Mathematics for Economists. Norton; Choudhury, Dipa; Horn, Roger A. (April 1987). A Complex Orthogonal-Symmetric Analog of the Polar Decomposition. SIAM Journal on Algebraic and Discrete Methods; Meyer, C. D. (2000), Matrix Analysis and Applied Linear Algebra, SIAM; all of which are incorporated by reference herein in their entirety, describe techniques that can be used to improve memory management at the time of storing data (e.g. to try to minimize the amount of memory needed to store large amounts of data). This is also an important aspect in mobile or wearable devices which must optimize their memory resources in order to improve the performance of all the applications running on the device, including the application handling such large amounts of data, thus improving the user experience when handling large amounts of data. By way of example, some embodiments may use a matrix factorization to optimize memory resources at the time of storing the second set of the second amount of values (please note that some embodiments may use a matrix factorization at the time of storing the first set of the first amount of values, and later reverse the process to obtain an approximation of the first set of the first amount of values from which to obtain the second set of the second amount of values using any of the techniques described throughout this disclosure, or any other(s), while other embodiments may use any other techniques and/or amounts and/or approaches and/or sets and/or order(s) and/or any other(s) and/or any variations and/or any combinations thereof). By way of example, some embodiments may use a matrix factorization comprising a singular value decomposition to optimize memory resources at the time of storing the second set of the second amount of values (again, please note that some embodiments may use a matrix factorization comprising a singular value decomposition at the time of storing the first set of the first amount of values, and later reverse the process to obtain an approximation of the first set of the first amount of values from which to obtain the second set of the second amount of values using any of the techniques described throughout this disclosure, or any other(s), while other embodiments may use any other techniques and/or amounts and/or approaches and/or sets and/or order(s) and/or any other(s) and/or any variations and/or any combinations thereof); for this, some embodiments may use the second set of the second amount of values (which up to now may have been stored, for example, as an array of doubles within the application (the size of said array may be "second amount")), and convert said array of "second amount" of values, into a matrix of size m*n (e.g. m*n may be equal to "second amount", and m may be equal to n, or m may be different from n, or m*n may be different from "second amount", or some embodiments may use any other approach, and/or any variations and/or combinations thereof); the conversion of an array into a matrix (e.g. cutting as many chunks from the array as rows has the matrix, wherein each of the chunks has a length equal to the length of each row of the matrix, and pasting those chunks consecutively into the matrix as its rows) is a well-known process that is also described in some of the programming and/or algebra-related references mentioned in this or any of the incorporated references; additionally, the reader may consult the internet (e.g. https://stackoverflow.com) to search for additional details in these or other concepts and/or processes, and the contents of those websites are hereby incorporated by reference in their entirety for all purposes. Once the matrix has been obtained (e.g. said matrix can be called M, and can have an amount of values equal to m*n, which may be equal to "second amount"), said matrix M can be decomposed (using a factorization comprising a singular value decomposition) into 3 matrices. In some embodiments, the singular value decomposition of a m*n real or complex matrix M may be considered as a factorization of the form U*S*V', where U is an m*m real or complex unitary matrix, S is an m*n rectangular diagonal matrix with non-negative real numbers on the diagonal, and V is an n*n real or complex unitary matrix. The diagonal entries "si" of S are known as the singular values of M. The columns of U and the columns of V are called the left-singular vectors and right-singular vectors of M, respectively. The singular value decomposition can be computed using the following observations: 1) The left-singular vectors of M are a set of orthonormal eigenvectors of M*M'. 2) The right-singular vectors of M are a set of orthonormal eigenvectors of M'*M. 3) The non-negative singular values of M (found on the diagonal entries of S) are the square roots of the non-negative eigenvalues of both M'*M and M*M'. In some embodiments, the "'" may refer to the conjugate transpose; further details can be found in any of the incorporated references above, and in https://en.wikipedia.org/wiki/Singular_value_decomposition and any references therein, all of which are hereby incorporated by reference in their entirety. In some embodiments, once we have decomposed M into U, S, and V matrices, a reduced number of singular values (diagonal entries "si" of S) can be selected based on any criteria (e.g. selecting only the strongest or largest ones, or any other criteria using any of the properties that can be determined from any of the involved matrices and/or their elements); in some embodiments, for example, if matrix M is of size m*n=60*60=3600 ("second amount" may be equal to 3600), the number of selected singular values can be e.g. 1, 2, 3, 4, 5, 6, 7, 8, 9, 10, 20, or other number (obviously constrained by the size of the involved matrices, and depending on any criteria, including the size of the involved matrices, the quality of the values being stored, etc.); in some embodiments the number of selected singular values can be a number below a threshold, and in some embodiments, said threshold may be below 10 (e.g. 1, 2, 3, 4, 5, 6, 7, 8, 9); in some embodiments, once we have selected a reduced number of singular values (we can call said number "number_of_selected_singular_values"), some embodiments can select and store a reduced number of elements from the matrices resulting from the factorization; by way of example without limitation, instead of having to store a matrix M of m*n elements, some embodiments may choose to store only a number of selected singular values (e.g. first "number_of_selected_singular_values" diagonal elements from matrix S), together with first "number_of_selected_singular_values" columns of matrix U, together with first "number_of_selected_singular_values" rows of matrix V'; this is a well-known methodology allowing the compression of data (despite loosing some details of the data), and further details can be found at least in the following references:

https://en.wikipedia.org/wiki/Singular_value_decomposition;
https://en.wikipedia.org/wiki/Matrix_decomposition;
https://en.wikipedia.org/wiki/Principal_component_analysis;
https://en.wikipedia.org/wiki/Dimensionality_reduction;
https://en.wikipedia.org/wiki/Nonlinear_dimensionality_reduction;
https://intoli.com/blog/pca-and-svd/; books: Steven L. Brunton, J. Nathan Kutz, "Data-Driven Science and Engineering: Machine Learning, Dynamical Systems, and Control", Cambridge University Press, Feb. 28, 2019; Charles K. Chui, Qingtang Jiang, "Applied Mathematics", Springer Science & Business Media, 2013, ISBN 9789462390096; Masayuki Numao, Thanaruk Theeramunkong, Thepchai Supnithi, "Trends in Artificial Intelligence: PRICAI 2016 Workshops", Springer, 2017, ISBN 9783319606750, and references therein, all of which are hereby incorporated by reference in their entirety for all purposes (please note that depending on whether we consider transpose or not, some authors may refer to rows or columns of some of the involved matrices when selecting a reduced number of elements from said matrices). Consequently, in some embodiments, we are achieving an important reduction in the amount of memory needed to store the data (e.g. instead of having to store 60*60=3600 values, we can store (e.g. if number_of_selected_singular_values=5): 5+60*5+60*5=605 values); this optimization of memory resources frees an important amount of memory in the mobile or wearable device which can be used to better manage the applications running in the device; in other words, the important memory saving achieved through this methodology provides an improvement at least in the user experience of the user (e.g. the device has plenty of memory to better handle resources required by applications in the device). In some embodiments, the reduced amount of values (e.g. said 605 values of the previous example) can be stored in memory, and used when required to generate a set of 3600 values which can be an excellent approximation to the original 3600 values of the first set of the example. As described in the incorporated references, some embodiments can use said e.g. 605 values to generate new U, S, V' matrices from them (just reversing the previous steps), e.g. filling in with 0's the missing values of said matrices; for example, the 5 singular values are used to generate a new diagonal matrix S with said 5 singular values as the first 5 elements of its diagonal (rest of elements of new S will be 0); the 60*5 values from the original U are used to create a new matrix U containing said 60*5 values in its first 5 columns (rest of elements of new U will be 0); the 60*5 values from the original V' are used to create a new matrix V' containing said 60*5 values in its first 5 rows (rest of elements of new V' will be 0); (M, U, S and V' (and the new ones) are considered square matrices (e.g. 60*60) in this example); eventually, a new matrix M can be obtained from the newly generated matrices U, S, V' as: M=U*S*V', as described in the incorporated references. In other words, now we have again 3600 values which are a good approximation of the original 3600 values. Some embodiments may obtain e.g. an array of e.g. 3600 values holding the 3600 values of the new matrix (converting a matrix into an array (e.g. one-dimensional array) is well-known and also described in the references incorporated above; for example, some embodiments can reverse the process used to obtain a matrix from a one-dimensional array (described above, using chunks, as also described in any of the references)). It is interesting to note that some embodiments may use different numbers, and/or different dimensions of matrices, and/or different techniques and/or methodologies, and/or any variations and/or combinations thereof. By way of example, instead of 3600 as the amount ("second amount") of values of the second set (from which matrix M is generated), some embodiments may use 9000 or 90000 or 1000000 (1 Million) or other values in between (e.g. 9500, 10000, 50000, 200000, 400000, etc.) or even larger than 1 Million, depending on the hardware specifications of the mobile or wearable device (e.g. it could be possible to assign each one of said values to each one of the pixels of the screen of the device, so theoretically we could handle, by way of example without limitation, a number of values equal to the total number of pixels of the screen of the device (e.g. current state-of-the-art smartphones have screens with e.g. 2160*1080=2332800 pixels, so we could handle e.g. 2332800 values)). In some embodiments, the previously called "second amount" can be selected based on the size and density of the screen of the device in order to try to handle as many values as the physical size of the screen allows, but also keeping a good user experience considering the specific density of the screen (e.g. if the density is very high, we can reduce the total number of values, because the human eye may have difficulty distinguishing different pixels in a very dense screen, while other embodiments may use any other approaches and/or variations and/or combinations thereof).

Next, some embodiments may determine metadata from (or corresponding to) the obtained second set of the second amount of values; some embodiments may use the original second set of the second amount of values (before using matrix factorization), while other embodiments may use the second set of the second amount of values resulting after using the matrix factorization (again, the differences between both "second sets" are generally small); other embodiments may instead determine the metadata using the first set of the first amount of values representing measurements of the gait attribute, while other embodiments may use any other approaches and/or methodologies and/or sets and/or values and/or amounts and/or any other(s) and/or any variations and/or combinations thereof; in some embodiments, the determined metadata may comprise: the average value of the second set of the second amount of values, the most common value, the minimum, the maximum, the middle value, other statistics, the total time of activity accounted for with said second set of values (e.g. how long is the time interval spanned by the values contained in the second set; this time length can be determined in some embodiments as: e.g. knowing the frequency of determination of the values contained in a set, and the total number of values contained in it (e.g. multiplying number of values by inverse of determination frequency), while other embodiments may use the original first set of values to determine this time length, or any other metadata); in some embodiments, the metadata may also comprise: the source (in terms of geographical location, which may be determined e.g. using GPS (as lat long coordinates, or in any other way) and/or other sensors of the device, at the time the activity was started, i.e. the values were started to be recorded) of the activity, the destination (in terms of geographical location, which may be determined e.g. using GPS (as lat long coordinates, or in any other way) and/or other sensors of the device, at the time the activity was finished, i.e. the recording of values ended) of the activity, an identification of the followed route (e.g. GPS coordinates determined during the activity may identify a route previously identified by the user as one of the common routes used by the user when exercising), whether the route is a frequent or less common route for the user, how the determined gait parameters for this set of data compare with other sets of data previously determined for this and/or other routes, and other information. In some embodiments, e.g. when access to GPS is not possible (e.g. indoor environments), or when the user selects "airplane mode" in his/her device so that localization methodologies based on radio-frequency can not be used, we can estimate the likely destination of the user by processing the data (e.g. by determining statistics from the first set of data, or from the second set of data, and comparing the determined statistics with other statistics previously determined for other sets of other days (which can be stored in the device) for which the destination is known, and assigning the likely destination to be the destination from the set of data whose statistics are closest to the statistics of current data); for example, if the mean and/or standard deviation and/or skewness and/or kurtosis, and/or any others and/or any variations and/or combinations thereof, determined from the current second set of data have values which are very close (e.g. their differences are smallest among all possible cases) to the values determined for the day Jan. 18, 2020 (e.g. a day for which the source and the destination and the whole route coordinates were known and recorded thanks to the use of GPS), some embodiments may consider that the likely destination for the current second set of data may correspond with the destination recorded for Jan. 18, 2020. In these embodiments, we can determine and display additional metadata corresponding to the likely destination, such as an average time to travel the route, whether the destination of the route is a frequent or less traveled destination for the device (or user), an estimated average caloric consumption for the route (or to arrive at the likely destination), the average air quality for the route (including the likely destination) which may be obtained e.g. by checking internet websites providing air quality for particular locations (e.g. googling "air quality California" provides a list of possible websites), and other information; in other words, in some embodiments, the metadata is specific to the likely destination and displaying the metadata is a technical activity that is not a longstanding human practice; and it provides an improvement to numerous technical fields such as e.g. health monitoring, by allowing doctors and/or users to better estimate caloric consumption and/or air quality breathed during the activity. It is also interesting to note that displaying the data and the additional metadata provides an improvement at least to the field of medical condition diagnosis (e.g. allowing doctors to better diagnose potential medical conditions using metadata), and the metadata provides an improvement also at least to the field of fitness performance monitoring (e.g. allowing athletes to better assess their workouts and compare with other workouts in different conditions using metadata).

Next, some embodiments may determine a set of thresholds specific to each gait attribute (or gait characteristic) of the user (please note that some embodiments may simultaneously determine several gait characteristics, such as "velocity", and/or "step length", and/or "calories/hour" (or calories burned per hour), and/or "frequency" (or cadence)); by way of example without limitation, some embodiments may determine a number (e.g. 3 or 4 or 5 or 6 or 7 or 10 or 20 or any other number) of thresholds for the gait attribute "velocity" (and/or "step length", and/or "calories/hour" (or calories burned per hour), and/or "frequency" (or cadence)) as follows: first_threshold=coef_1* metadata_parameter; second_threshold=coef_2*metadata_parameter; third_threshold coef_3*metadata_parameter; etc., where coef_1, coef_2, coef_3 are coefficients that can be determined using any values and/or any of the determined metadata of the second set of the second amount of values, or using any other criteria and/or values (e.g. a simplistic example of embodiment could choose coef_1=0.05; coef_2=0.15; coef_3=0.25, etc. and/or any other values and/or any variations and/or combinations thereof), while metadata_parameter can be e.g. the average value of the values of the second set of the second amount of values, or the most common value of the values of the second set of the second amount of values (e.g. 234.5 Cal/h), or the standard deviation of the values of the second set of the second amount of values, or any statistical parameter of the values of the second set of the second amount of values, or any other type of parameter determined using the values of the second set of the second amount of values (said values representing measurements of the gait attribute); please note that some embodiments may use values of the first set of the first amount of values, instead of values of the second set of the second amount of values, while other embodiments may use any variations and/or combinations thereof.

Next, some embodiments may create an array (or populate, or fill in a previously created array) or a list (or any other data structure) or a set of values representing colors; in some embodiments, the colors are represented as integer numbers (e.g. 0xffffff for white color); in some embodiments, said array (we can call it "array_of_intColors_for_setpixels") may have a size equal to the previously referred "second amount" (e.g. 3600 in a previous example), and it can be populated (or filled in) with values representing colors; in other words, we are obtaining a second set of a "second amount" of values representing colors (the values represent colors), wherein the "second amount" of this second set (of colors) is the same as the previously referred "second amount" of the previously referred second set (whose values did not represent colors, but were related to measurements of the gait characteristic); in order to avoid confusing the reader, we have 2 second sets of "second amount" of values (the first one previously mentioned, whose values were related to gait attribute measurements, and the second one whose values represent colors); an example of embodiment may obtain said second set of the second amount of values representing colors using code that can be described with the help of the schematic Java-style pseudocode (please see coding explanations in any of the programming related references incorporated in this application or in any incorporated reference of the incorporated applications) shown next (please remember that in this example of embodiment: "second_amount"=3600; "second_set" represents the array of the first second set of the "second amount" of values (e.g. whose values are related to gait attribute measurements obtained e.g. after the matrix factorization process); "meta_param" represents a parameter of the determined metadata (e.g. any of the previously mentioned); first_threshold, second_threshold, and third_threshold represent the previously mentioned thresholds; first_color, second_color, third_color represent colors; and array_of_intColors_for_setpixels represents an array holding the values of the second set of the second amount of values representing colors (in other words, said second set of the second amount of values representing colors, is obtained next, using a first "second set" (it was also called "second set" in a previous example, but it is different from the second "second set" of the second amount of values representing colors, in the sense that its values represent measurements of a gait attribute) of the second amount of values representing measurements of a gait attribute)):

```
for (int i=0; i<second_amount; i++) {
  if (Math.abs(second_set[i]-meta_param)<first_threshold)
    array_of_intColors_for_setpixels[i]=first_color;
  else if (first_threshold<=(second_set[i]-meta_param)
    && (second_set[i]-meta_param)<second_threshold)
    array_of_intColors_for_setpixels[i]=second_color;
  else if (second_threshold<=(second_set[i]-meta_param)
    && (second_set[i]-meta_param)<third_threshold)
    array_of_intColors_for_setpixels[i]=third_color;
  }
  . . .
}
```

In other words, some embodiments obtain a second set of a "second amount" of values representing colors, by using a second set of a "second amount" of values representing measurements of the gait attribute (please note that the "second amount" of both second sets, is the same), wherein the second set of the second amount of values representing measurements of the gait attribute has been previously determined (or obtained) using a first set of a first amount of values representing measurements of the gait attribute (e.g. using an interpolation on said first set, and/or leveraging a matrix factorization). In other words, some embodiments obtain, using an interpolation on the first set of the first amount of values (said values representing measurements of the gait attribute), a second set of a second amount of values representing colors. And some embodiments obtain, using the first set of the first amount of values (said values representing measurements of the gait attribute) and leveraging a matrix factorization, a second set of a second amount of values representing colors.

As can be seen in the pseudocode above, some embodiments are creating ranges of a width controlled by thresholds (first_threshold, second_threshold, third_threshold, . . . ), wherein said thresholds (and consequently the ranges too) can be varied arbitrarily (e.g. can be made dependent on the previously determined "metadata_parameter" or "meta_param"); therefore, some embodiments may use ranges of different sizes (e.g. using "metadata_parameter" to control said sizes as shown in the pseudocode above). The pseudocode above shows the creation of ranges (of values of the second set of the second amount of values representing measurements of the gait parameter) for which values of another second set (the values of this other second set (array_of_intColors_for_setpixels) representing colors) will be assigned a particular color, and the use of "meta_param" (or "metadata_parameter") together with the values of the second set of values representing measurements of the gait attribute, for the creation of said ranges; the skilled reader will understand that a similar approach can be followed to obtain the ranges below "meta_param"; e.g.: else if (first_threshold<=(meta_param-second_set[i]) && (meta_param-second_set[i])<second_threshold) array_of_intColors_for_setpixels[i]=fourth_color; . . . and so on. The skilled artisan will also understand with the help of the pseudocode above that some embodiments can make use of a variable number of ranges (depending at least on the values of the thresholds, and/or the actual range of the values present in the second set of the second amount of values representing measurements of the gait attribute). Please note that in some embodiments, 2 different sets are called "second set", because both have the same amount of values ("second amount"); however, they are different because one of them ("second_set" in the pseudocode above) contains values representing measurements of the gait attribute, while the other one (array_of_intColors_for_setpixels) contains values representing colors.

Next, some embodiments may create an image using a one-to-one correspondence between: the values representing colors (e.g. values of the second set of the second amount of values representing colors), and pixels of the image. This can be described with the help of the schematic Java-style pseudocode (please see coding explanations in any of the programming related references incorporated in this application or in any incorporated reference of the incorporated applications, including https://en.wikipedia.org/wiki/Bitmap; https://developer.android.com/; https://developer.android.com/reference/android/graphics/Bitmap; Raydelto Hernandez "Building Android Games with Cocos2d-x" (2015), Packt Publishing Ltd; Mir Nauman Tahir "Learning Android Canvas" (2013), Packt Publishing Ltd; and references therein, all of which are hereby incorporated by reference in their entirety for all purposes) shown next:

RectF whereToDraw=new RectF(0, 0, 480, 608);
  Bitmap new_bitmap;
  new_bitmap=Bitmap.createBitmap(bitmap_width, bitmap_height, Bitmap.Config.RGB_565); //ARGB_8888);
  new_bitmap.setPixels(array_of_intColors_for_setpixels, 0, bitmap_width, 0, 0, bitmap_width, bitmap_height);
  canvas.drawBitmap(new_bitmap, null, whereToDraw, null);

Focusing on the schematic Java-style pseudocode above, some embodiments may create a rectangle (e.g. specifying coordinates of the device screen where the image will be displayed): "RectF whereToDraw=new RectF(0, 0, 480, 608);" in an example of embodiment, the rectangle can be specified by its left, top, right, bottom coordinates, e.g. (0, 0, 480, 608) which may specify a rectangle of e.g. 480*608 pixels in the screen of the device, with its left top point coinciding with the left top origin (0,0) of the screen of the device; other embodiments may use different numbers (e.g.: (0,0,60,60), or (0,0,300,400), or (100,100,400,500), or other values depending on the hardware specifications of the device screen (e.g. screen resolution, density, etc.), and other criteria) and/or methods and/or any variations and/or combinations thereof (for additional details, please see https://developer.android.com and https://developer.android.com/reference/android/graphics/RectF, the contents of which are hereby incorporated by reference in their entirety for all purposes).

Next, some embodiments may create a Bitmap that may represent the image to be displayed. A bitmap may be considered in some embodiments as a type of memory organization or image file format used to store digital images, or to refer to the concept of a spatially mapped array of pixels; raster images in general may be referred to as bitmaps; many graphical user interfaces use bitmaps; in some contexts and/or embodiments, a bitmap may refer to an image with at least one bit per pixel, while in other embodiments, a bitmap is generally considered as an image. Please see https://en.wikipedia.org/wiki/Bitmap and references therein (all of which are hereby incorporated by reference in their entirety for all purposes) for more details.

By way of example without limitation, focusing on the pseudocode above: "Bitmap new_bitmap; new_bitmap=Bitmap.createBitmap(bitmap_width, bitmap_height, Bitmap.Config.RGB_565);" creates a bitmap with dimensions bitmap_width and bitmap_height (e.g. some embodiments may use bitmap_width=60 and bitmap_height=60 in order to use 60*60=3600 pixels in the bitmap or image, which may correspond (e.g. using a one-to-one correspondence) with the previously determined 3600 values representing colors, which may themselves correspond (e.g. using a one-to-one correspondence) with the previously determined 3600 values representing measurements of the gait attribute); other embodiments may use other numbers (e.g. bitmap_width=300 and bitmap_height=300 in order to use 300*300=90000 pixels, bitmap_width=500 and bitmap_height=1000 in order to use 500*1000=500000 pixels, and/or values for bitmap_width and/or bitmap_height ranging from e.g. 30 to 2000 (e.g. 50, 80, 100, 150, 190, 280, 1024, 1900, etc.) and/or any other values and/or subranges in between (or above in other embodiments), etc.), and/or different methods and/or different techniques and/or any variations and/or combinations thereof. Focusing on the pseudocode above: "Bitmap new_bitmap; new_bitmap=Bitmap.createBitmap(bitmap_width, bitmap_height, Bitmap.Config.RGB_565);" creates a bitmap with a configuration of RGB_565 (each pixel is stored on 2 bytes and only the RGB channels are encoded: red is stored with 5 bits of precision (32 possible values), green is stored with 6 bits of precision (64 possible values)

and blue is stored with 5 bits of precision); other embodiments may use different configurations, e.g. ARGB_8888 (each pixel is stored on 4 bytes. Each channel (RGB and alpha for translucency) is stored with 8 bits of precision (256 possible values)).

Next, some embodiments may assign or set or replace the pixels of the created image (new_bitmap) using a one-to-one correspondence between the values representing colors (e.g. values of the second set of the second amount of values representing colors (e.g. array_of_intColors_for_setpixels)), and the pixels of the created image (new_bitmap); for this, some embodiments may use: "new_bitmap.setPixels(array_of_intColors_for_setpixels, 0, bitmap_width, 0, 0, bitmap_width, bitmap_height);", wherein the "setPixels" method (this example of embodiment is using Android operating system, but any other methods and/or operating systems can be used in other embodiments) replaces the pixels in the bitmap (new_bitmap) with the colors in the array (array_of_intColors_for_setpixels, which represents the values of the second set of the second amount of values representing colors). The rest of parameters used by the "setPixels" method (explained in detail in the incorporated references (e.g. https://developer.android.com/reference/android/graphics/Bitmap)) can be controlled in some embodiments following different criteria (in general, the "setPixels" method can be described by its parameters as follows: setPixels (int[ ] pixels, int offset, int stride, int x, int y, int width, int height), wherein each parameter is described as follows: pixels: colors to write to the bitmap; offset: index of the first color to read from pixels[ ]; stride: number of colors in pixels[ ] to skip between rows; normally this value will be the same as the width of the bitmap, but it can be larger (or negative); x: x coordinate of the first pixel to write to in the bitmap; y: y coordinate of the first pixel to write to in the bitmap; width: number of colors to copy from pixels[ ] per row; height: number of rows to write to the bitmap).

Next, some embodiments may display the created image on the screen of the mobile or wearable device (e.g. to generate a user interface that displays at least said image), by way of example without limitation, as follows: "canvas.drawBitmap(new_bitmap, null, whereToDraw, null);", which e.g. may be included in the "doDraw" method (this is a well-known procedure, please see incorporated references (at least application Ser. Nos. 16/275,323 and 16/505,629, or any other incorporated reference) if additional details are needed).

As conveyed at least throughout the rest of this application's Specification, we have created a useful image (e.g. in a single screenshot (e.g. a single screen in a user interface) we can present e.g. 3000 values (or less or more) resulting from a correspondence from measurement of a gait attribute, providing a very high time resolution (e.g. even sub-second time resolution, because each pixel in the created image may correspond to each measurement of the gait attribute determined with an update frequency of e.g. 3 Hz or other frequency; for example, one embodiment could determine a gait attribute continuously through a whole day at 3 Hz, thus obtaining approximately 259200 measurements, which could be fit in a square image of approximately 510*510=260100 pixels, which could fit in the screen of some devices (current state-of-the-art devices may have screen of e.g. 2160*1080=2332800 pixels); anyway, this is just an example, and other examples may use different numbers; for example, a workout of an athlete during 1 day may last approximately 1 hour, which could generate approximately 10000 measurements, which could be fit in a 100*100=10000 pixels image, which will easily fit in most screens of mobile or wearable devices to present a pleasantly colorful and detailed evolution of the gait attribute, with many more measurements and much higher time resolution than conventional approaches, thus providing an improvement at least to e.g. an athlete to better monitor his/her workouts and better plan his future training plans leveraging the detailed information (e.g. the athlete may decide he/she needs to focus on particular time intervals of his/her 1 hour workout at which he/she observes a significant drop in the value of the gait attribute). In other words, the created image is a useful, colorful and easy to understand image which improves the user experience in comparison with conventional approaches (which use monotonous numbers or histograms conveying the total amount of steps taken or calories burned by the user with a time resolution of 1 hour or 1 day); this created useful image provides improvements to numerous fields: e.g. at least: provides a better user experience than conventional approaches (at least because the user enjoys a colorful display presenting a larger amount of data with a higher time resolution), and provides doctors and/or health related professionals with more data and higher resolution in the data to better diagnose potential medical conditions.

In some embodiments, displaying the created useful image is all which is needed to generate a user interface; other embodiments may display additional elements besides the created useful image to generate a more elaborate user interface; other embodiments may add other capabilities to the user interface (e.g. device screen), such as enable touch gestures to control elements displayed in the user interface; other embodiments may use any other elements, and/or techniques, and/or variations and/or combinations thereof. Consequently, some embodiments may generate a user interface that displays at least the created image; other embodiments may generate a user interface that displays at least the created image and additional metadata corresponding to the created image; for example, it is well known to display text on the screen of the device, using e.g. canvas.drawText (metadata_text, 280, 240, textPaint); this example makes use of the method "drawText(String text, float x, float y, Paint paint)", which draws the text with origin at (x,y) using the specified paint; (for more details, please see https://developer.android.com/reference/android/graphics/Canvas, hereby incorporated by reference in its entirety for all purposes). Other embodiments may use other methods, and/or techniques, and/or elements to be displayed on the screen (thus generating a more sophisticated user interface), and/or any variations and/or combinations thereof.

Figure 14:
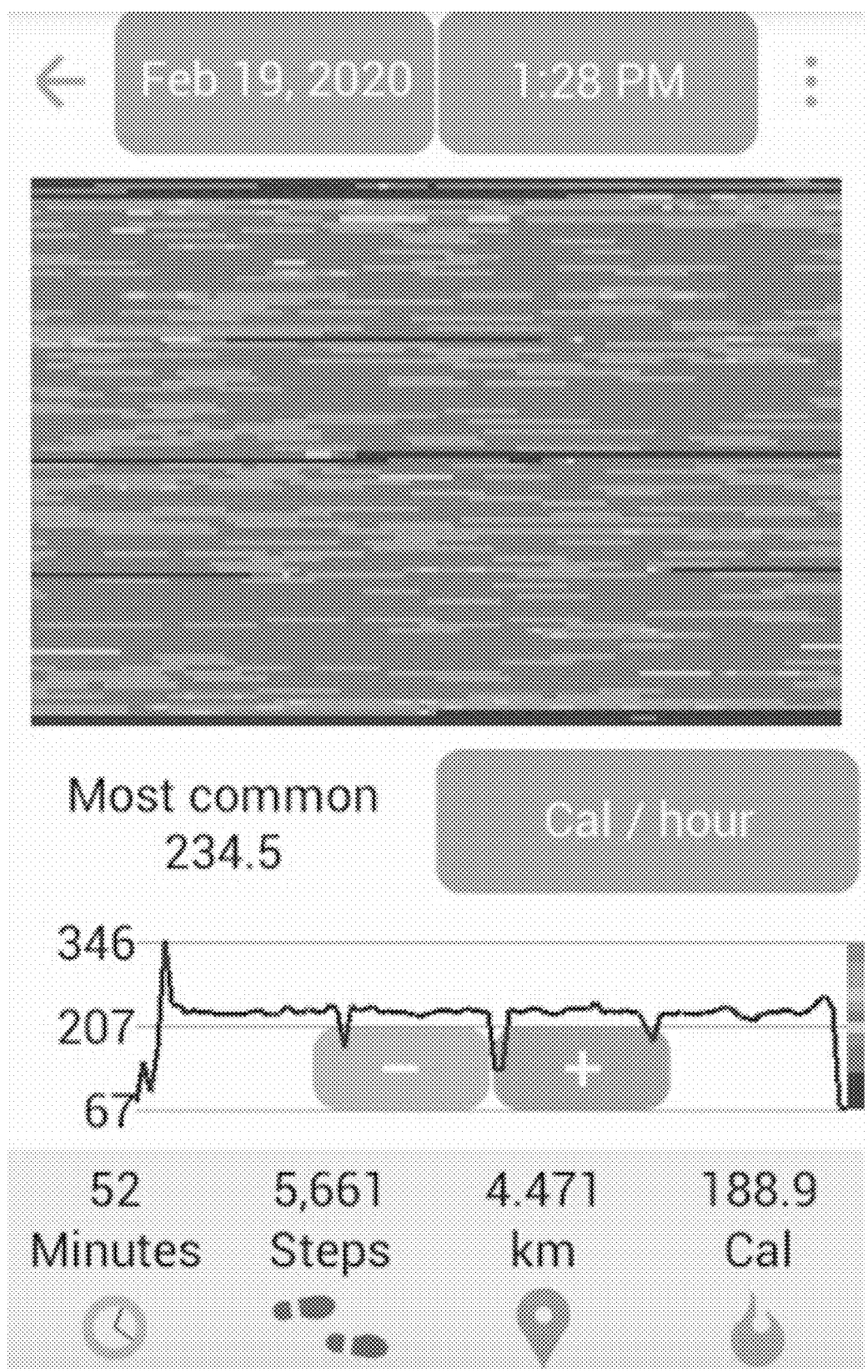
FIG. 14 shows an example of a user interface of an embodiment, displaying at least data related to the mobile or wearable device user's gait.

FIG. 14 represents an example of an embodiment of a user interface in a mobile or wearable device; in some embodiments, FIG. 14 may represent a screenshot from a smartphone (e.g. an Android phone, although any other type of operating system and/or device can be also applicable and/or used). By way of example without limitation, the top stripe of the user interface may comprise 4 elements: an arrow on the left, followed by a rectangular box displaying a date, followed by a rectangular box displaying a time, followed by three dots vertically aligned. The arrow on the left may be used to navigate away from the current screen; in other words, when the user touches the area containing the arrow, the user interface currently displayed disappears, and a new user interface is displayed; typically, the user is brought back to the previous screen from where he/she accessed the current screen (user interface). This is a typical element in many browsers. To the right of the arrow, we can find a rectangular (e.g. with rounded corners) box containing a date; the date may correspond to the date the displayed activity took place; when the user touches this box, some embodiments may display a calendar from where the user can select a new date; in some embodiments, the calendar will display the days containing recorded activities (for example, a smiley face around the number of the day may be used to indicate the days containing recorded activities); the user may touch (or select) a day number with a smiley face in the calendar, which will have the effect of displaying the user interface of FIG. 14 with the selected date. To the right, we can find a rectangular (e.g. with rounded corners) box containing a time; the time may correspond to the time the displayed activity took place; in some embodiments, the user may touch this box in order to display a list of activities recorded for the date displayed in the current user interface; for example, if "Feb. 19, 2020" has 3 activities recorded (e.g. one ending at "1:28 PM", which is the one being displayed in FIG. 14, another one ending at "3:32 PM", and another one ending at "6:54 PM"), by touching the box containing the time, the user interface will generate a list of the recoded activities; the user will be able to touch any of the listed times in order to select the particular activity he/she want to display. To the right, we can find three dots vertically oriented; when the user touches these 3 dots, a menu may pop up with options regarding the current activity (e.g. "Delete it", or "Save it" (e.g. in case it was not previously saved, and it was just the current activity being recorded (e.g. in RAM memory) but without having been saved to disk memory (e.g. SD card))). Other embodiments may use any other elements and/or any variations and/or combinations thereof. Continuing with the description of FIG. 14, below the top stripe, we can see a big rectangle (which can be a square in some embodiments, or a trapezoid in other embodiments) occupying most of the top half of FIG. 14's user interface (please note that a square is a special case of a rectangle, which is a special case of a parallelogram, which is a special case of a trapezoid, so we can refer to the previously mentioned "big rectangle" as "trapezoidal image" throughout this whole disclosure); this big rectangle contains dots of different colors, aligned in rows and columns (giving the appearance of narrow stripes for some of the rows); although FIG. 14 has been gray-scaled for submission to the USPTO, the reader should note that different colors (e.g. red, orange, yellow, light green, green, cyan, light blue, blue, dark blue) can be used in some embodiments for this big rectangle (and for the rest of elements of the user interface); in some embodiments, this big rectangle corresponds to the previously referred useful image created using the second set of the second amount of values representing colors; in other words, this big rectangle represents the measurements of the gait characteristic (e.g. calories burned per hour, and/or velocity, and/or step length, and/or frequency) which were recorded in the first set of the first amount of values, by means of colors, the colors being scaled (e.g. from red (largest value) to dark blue (smallest value)); this big rectangle can also be seen as representing a matrix of dots of color, with the dots ordered from top to bottom and from left to right, creating horizontal rows flowing from the top to the bottom; in other words, the dots of this big rectangle are organized and ordered in time, as in a matrix, or as the dots in a television screen, or as the characters in this writing (from top to bottom and from left to right, so that the first dot in time is place at the left of the top row, with the next dots in time following along the same top row until the right edge of the top row is reached, at which point the next dots are placed on the left of the second row and continue towards the right, and so on until the bottom row is reached, which is also filled from left to right); in this example of embodiment, there are 100 rows, each containing 100 dots, so the total amount of dots in this big rectangle is 10000; the activity represented in this FIG. 14 took 52 minutes, and the gait characteristic (in this example, calories burned per hour, although other embodiments may use velocity, or frequency or step length) was determined with an update frequency larger than 3 Hz (e.g. 4 Hz, although other embodiments may use other frequencies, larger or smaller), so that the previously mentioned "first amount" of the first set of measurements of the gait characteristic may be e.g. 52 minutes*60 seconds/minute*4 measurements/second=12480; consequently, in some embodiments, from those 12480 values we obtained the 10000 values representing colors as previously described, and the 10000 values representing colors are displayed as each one of the 10000 dots of the big rectangle of FIG. 14; as can be observed in said big rectangle (useful image) the dots usually follow long lines with a same color (e.g. a time interval of several seconds in which the gait characteristic took a same value), although occasionally we can see single dots of different color (e.g. a short time interval of approximately less than a second in which the gait characteristic took a value different from the surrounding time intervals); in other words, by looking at this big rectangle, we can visually observe the time evolution of the gait characteristic with a very high time resolution (e.g. sub-second time resolution (e.g. approximately 0.25 sec, or 0.3 sec, or 0.5 sec, or any other value), or a time resolution of a threshold number of seconds or less (e.g. approximately 4 seconds or less, or 2 seconds or less, or 1.5 seconds or less, or 1 second or less, or any other value)); for example, the top first row and the bottom last row are the same color (dark blue), which represents lowest values of the gait characteristic (e.g. approximately 67 Cal/hour, which corresponds to the user being still (without moving), which occurred at the beginning and at the end of the activity); there is also a dark blue line approximately at the middle of this big rectangle, which corresponds to the user having stopped for a while at the middle of the activity; the same dark blue color can be observed approximately at the first and third quarters of this big rectangle (the user stopped for shorter time intervals); on the other hand, after the very first rows at the top, the user run for a little while, which translates into a red color (although the red color may not be clearly appreciated in this gray-scaled version of FIG. 14, the time chart displayed below (with top axis indicating 346, middle axis indicating 207, and bottom axis indicating 67) displays a peak (346) in the measured gait activity, which corresponds to the red color in the big rectangle); during the rest of the activity, the gait characteristic fluctuated around a value of 234.5 Cal/hour, which was the most common value for the gait characteristic during this activity. In conclusion, this big rectangle (useful image) occupying most of the top half of FIG. 14, provides an easy visualization (in terms of scaled colors) of the measurements of the gait characteristic, with a high time resolution (even sub-second time resolution), in contrast with traditional approaches which provide a low time resolution (e.g. 1 hour or 1 day time resolution).

Following with the description of the rest of elements of FIG. 14, below the previously described big rectangle, we can see text "Most common 234.5" and another rectangle (with rounded corners) displaying "Cal/hour". The text "Most common 234.5" is an example of the data and/or metadata that can be displayed in some embodiments; in this particular example, we are displaying the value of the most common measurement of the gait characteristic for this particular activity (234.5 Cal/hour, corresponding to a typical user during a walking activity); other embodiments may display any other statistics and/or any other data and/or metadata as previously described. To the right of the text, we see the rectangle displaying "Cal/hour"; in some embodiments, the user can touch (or press) this rectangle, and a menu will pop up displaying a list of gait characteristics that the user can select for display (e.g. instead of Calories/hour, the user can select to display "velocity", "step length", "frequency", and/or any other gait characteristic, and/or any variations and/or combinations thereof). Please note that in some embodiments, the gait characteristic or attribute displayed in the "big rectangle" (e.g. calories burned per hour, and/or velocity, and/or step length and/or frequency (or cadence) and/or any other and/or any variations and/or combinations thereof) may be determined leveraging a determined gait cadence of the user, using any of the methodologies and/or techniques described in this patent application and/or in any of the incorporated references (by way of example without limitation, using a machine learning algorithm to determine the desired gait characteristic, using the determined user's cadence as a feature, as described at least in the incorporated references). Following with the description of the rest of elements of FIG. 14, below we can see a time chart, with top axis indicating 346, middle axis indicating 207, and bottom axis indicating 67; obviously these values (346, 207, 67) are activity specific, and will change accordingly with every activity; this time chart represents a time evolution of the measurements of the gait characteristic; in this particular example of embodiment, this time chart (or the thick black line in the time chart) contains 100 points, and each point has been computed as the average of values of measurements of the gait characteristic corresponding to each one of the 100 rows of the big rectangle above; in other words, the average of values related to measurements of the gait characteristic corresponding to each one of the rows in the big rectangle has been computed to create each point of the time chart; consequently, this time chart is a simplified numeric (in terms of values of measurements of the gait characteristic) version of the big rectangle.

In some embodiments, the number of points in the black think line of the time chart, or the number of points in the time chart, is equal to the number of rows in the "big rectangle", while in other embodiments it may greater than (or less than, in other embodiments) the number of rows in the "big rectangle". In some embodiments, the number of points in the time chart, is at least a third of the number of rows in the "big rectangle"; in some embodiments, the number of points in the time chart, being at least a third of the number of rows in the "big rectangle", has the functionality of trying to keep a visible correlation and/or a visual relationship between the rows in the "big rectangle" and the points in the time chart; assuming, for example, 100 rows in the "big rectangle", and that each point in the time chart represents the average of the measurements of the gait attribute linked to the points of 3 rows in the "big rectangle", would still manage to secure a visual correlation between the rows of the "big rectangle" and the points in the time chart; however, our tests show that larger numbers of rows being considered for each point in the time chart, may jeopardize said visual correlation, and the user may find it difficult to easily connect colors in the "big rectangle" with points in the time chart. In other embodiments, the number of points in the time chart, is greater than a maximum between: 30, and a third of the number of rows in the "big rectangle". In other embodiments, any other values and/or numbers and/or any variations and/or combinations thereof may be possible.

On the right of this time chart, we can see a vertical column of colors (or a vertical scale of colors, or a scale of colors), which, in some embodiments, represent the scale of colors applicable to both this time chart and the "big rectangle" above; although this gray-scaled document may not allow to clearly see the colors, we can tell the reader that the top color is red (assigned to values which include the maximum of the gait characteristic measurement, in this case, 346), followed towards the bottom by orange, followed by yellow, light-green, green, cyan, light blue, blue, and dark blue at the very bottom (assigned to values which include the minimum of the gait characteristic measurement, in this case, 67). In some embodiments, the schematic Java-style pseudo-code presented next, may be used to implement the time chart and the scale of colors applicable also to the "big rectangle" above; by way of example without limitation, the array of y coordinates to be displayed in the screen (as the black thick line in the time chart) can be created as follows (using e.g. the averages or values to be displayed, which may be contained in "array_of_averages_for_timeChart"):

```
for (int i=0; i<length_of_array_of_averages_for_timeChart; i++) {
    array_of_y_coordinates_for_points_in_timeChart[I]
    =
    y_coord_of_bottomGridAxisOfTimeChart
    -(float)(scaling_factor_forTimeChart*
      (array_of_averages_for_time Chart[I]-
minimum_of_array_of_averages_for_timeChart)
    );
}
```

Where length_of_array_of_averages_for_timeChart is the number of points of the black thick line in the time chart, array_of_y_coordinates_for_points_in_timeChart represents the array of y coordinates for the points of the time chart, which will be used to display the line of the time chart; for example, it is well-known and well-documented in the programming references incorporated in this disclosure how to draw a line in a chart once we have the y coordinates of the points of the line (the reader is given the freedom to choose the x coordinates, (e.g. in a simplistic example, an array of integers from 1 to 100)); for example, the "drawLine" method can be used in some embodiments as described in any of the incorporated references; the pseudo-code included uses names of variables which are self explanatory; the reader can find additional details in any of the programming references incorporated in this disclosure, since this is a very well-known area; for example, "y_coord_of_bottomGridAxisOfTimeChart" may represent the y coordinate of the bottom axis of the time chart (axis linked to value 67); "scaling_factor_forTimeChart" may represent a scaling factor to appropriately plot the values in the screen (e.g. it can be computed leveraging the available space in the screen for the chart, and the range of values to be plotted); "minimum_of_array_of_averages_for_timeChart" may be the minimum of the array of averages for the time chart (e.g. 67); in the pseudo-code above, "(float)" is used to convert the result of an operation into a float number.

Next, we include pseudo-code to obtain the y coordinates of a couple of rectangles of the vertical scale of colors displayed on the right of the time chart in FIG. 14; again, this is a very well-known area and very well documented in the programming references incorporated in this disclosure, so the skilled artisan will easily understand how to build the scale using this pseudo-code provided; first, some embodiments may define the thresholds that can also be used for the correspondence between measurements of the gait attribute and colors of points in the "big rectangle", as follows (and/or using any other values, and/or operations, and/or variations and/or combinations thereof):

double first_threshold=0.05*metadata_parameter;
    double second_threshold=3*first_threshold;
    double third_threshold=5*first_threshold;
    double fourth_threshold=10*first_threshold;
    double fifth_threshold=3500;

Next, making use of the previously determined "metadata_parameter" (e.g. most common value (e.g. 234.5 Cal/h), or average, or any other), we can go color by color, or rectangle of color by rectangle of color, deciding which rectangle of which color is going to be drawn; starting for example by the values closest to the "metadata_parameter", which may be assigned, for example, the "green" color, we can start by testing the first condition of the pseudo-code below, which is equivalent to checking if "metadata_parameter" is within certain boundaries; again, the names of the variables used in the pseudo-code are self explanatory; if said condition is true, we will draw a green rectangle in the vertical scale of colors, and said green rectangle will be defined using the y coordinates included in the pseudo-code (the reader is given the freedom to choose the x coordinates of said green rectangle (e.g. in a simplistic example, the x coordinate of the top left point of the rectangle may be 100, and the x coordinate of the bottom right point of the rectangle may be 101)); it is interesting to note that determining "scaling_factor_forTimeChart" is a very well-known topic, and very well documented in the incorporated references; for example, the scaling factor in a chart can be determined by dividing the y space available for the whole chart, by the range of the values that are going to be represented in the chart; and the y space available for the whole chart can be determined as the difference of the y coordinates of the bottom and top axes of the chart. It should also be noted that drawing a rectangle is a very well-known topic; for example, we can use the drawRect method, with a couple of points defining the rectangle: leftStart point (or left top point), and rightEnd point (or bottom right point); it is also well known that a point may be defined by an x coordinate and a y coordinate; the included pseudo-code provides the y coordinate, which is the difficult one; the reader is given the freedom to choose the x coordinate.

if (metadata_parameter>minimum_of_array_of_averages_for_timeChart
    && metadata_parameter<
maxToBeDisplayedFor_array_of_averages_for_timeChart
    )
    {
    draw_green_rectangle=true; //boolean for doDraw method.
    y_coord_leftStart_greenRectangle_vtcalScale
=Math.max(y_coord_of_topGridAxisOfTimeChart,
      (y_coord_of_bottomGridAxisOfTimeChart
        -(float)(scaling_factor_forTimeChart
        ((metadata_parameter+first_threshold)
      -minimum_of_array_of_averages_for_timeChart
      )
      )
    )
    );
    y_coord_rightEnd_greenRectangle_vtcalScale
=Math.min(y_coord_of_bottomGridAxisOfTimeChart,
      (y_coord_of_bottomGridAxisOfTimeChart
        -(float)(scaling_factor_forTimeChart
        *((metadata_parameter-first_threshold)
      minimum_of_array_of_averages_for_timeChart
      )
      )
    )
    );
    }

The process can be easily extended for the rest of rectangles of the scale of colors; the skilled artisan will easily understand how to apply the provided pseudo-code for the rest of rectangles of color of the vertical scale; just in case some reader might need more help (help in this area can easily be found in any of the incorporated references), next we provide pseudo-code for a second rectangle (the rectangle next to the green one, towards the top, which is the lightGreen rectangle):

if (maxToBeDisplayedFor_array_of_averages_for_timeChart>
    (metadata_parameter+first_threshold)
    )
    {
    draw_lightGreen_rectangle=true; //boolean for doDraw method.
    y_coord_leftStart_lightGreenRectangle_vtcalScale
=Math.max(y_coord_of_topGridAxisOfTimeChart,
      (y_coord_of_bottomGridAxisOfTimeChart
        -(float)(scaling_factor_forTimeChart
      *((metadata_parameter+second_threshold)
      minimum_of_array_of_averages_for_timeChart
      )
      )
    )
    );
    y_coord_rightEnd_lightGreenRectangle_vtcalScale
=y_coord_leftStart_greenRectangle_vtcalScale;
    }

Consequently, we are displaying (or providing): the "big rectangle", a time chart (since the points of the thick black line of the chart are related to measurements of the gait characteristic, which were determined orderly in time, and since we display them respecting their time order, those points are ordered in time, and thus, the chart is a time chart) correlated with the "big rectangle", and a vertical scale of colors; wherein said vertical scale of colors links the values of the time chart and the colors of the "big rectangle"; for instance, in the example shown in FIG. 14, the maximum of the time chart (346) corresponds with the top rectangle of the vertical scale of colors (in this case, a red rectangle), the minimum of the time chart (67) corresponds with the bottom rectangle of the vertical scale of colors (in this case, a dark blue rectangle), and a large number of points of the time chart (e.g. the points around the most common value of 234.5) corresponds with the middle rectangle of the vertical scale of colors (in this case, a green rectangle).

In some embodiments, said vertical scale of colors is composed of a number of rectangles of different colors (e.g. 1, 2, 3, 4, 5, 8, 9, 15, 30, or any other number of rectangles); it should be noted that in some embodiments, each one of the rectangles of said vertical scale may have different size, or different height (e.g. different spread along the y axis of the screen) due to the use of different thresholds; in the particular example of embodiment shown in FIG. 14, the vertical scale is composed of 9 rectangles (red on top, followed by orange towards the bottom, followed by yellow, light green, green, cyan, light blue, blue, and dark blue at the very bottom); for those 9 rectangles, we are using 5 different thresholds (e.g. first_threshold, second_threshold, third_threshold, fourth_threshold, fifth_threshold), and although FIG. 14 is gray-scaled, we can see 9 different rectangles, and we can see that some of them have clearly larger heights (e.g. the 2 rectangles at the very bottom have larger height than the rectangles by the middle).

Consequently, in some embodiments, the image created using a one-to-one correspondence between: the values representing colors, and pixels of the image (commonly referred to as "big rectangle" in this Specification), is displayed together with a time chart (which displays values of (or related to) measurements of a gait characteristic), and a scale of colors; wherein the scale of colors links values of the time chart with the colors of the created image ("big rectangle"); and in some embodiments, the scale of colors is composed of a number of rectangles of different colors, wherein the size of each one of the rectangles of different colors is proportional to a range of values of the time chart. Please note that the size of each one of the rectangles of different colors may be proportional to a range of values of the time chart, because we can use thresholds (e.g. different thresholds: first_threshold, second_threshold, etc.) which are employed in the determination of the y coordinates (and thus, the size) of the rectangles (as shown in the pseudo-code above), and those thresholds define ranges of values in the time chart (because as shown in the pseudo-code, the thresholds are e.g. added to "metadata_parameter", thus defining ranges of values of the time chart (e.g. in the pseudo-code above, "metadata_parameter+first_threshold" is responsible for the range of values between metadata_parameter, and "metadata_parameter+first_threshold")). Please also note that since we can use different thresholds (or different values for each threshold), the size (or height) of each rectangle of the scale of colors can be different (as can be seen e.g. in FIG. 14, which shows 9 rectangles, some of which have different heights (or sizes)). Consequently, in some embodiments, the height of the rectangles of the scale of colors follows a linear scale (or a proportional relationship) with values (or range of values) of the time chart; for example, in FIG. 14, the top rectangle (red) has a height linearly proportional to the range of values it represents in the time chart (e.g. from the maximum, 346, to a lower value in between 346 and 207); for example, in FIG. 14, the bottom rectangle (dark blue) has a height linearly proportional to the range of values it represents in the time chart (e.g. from the minimum, 67, to a higher value in between 67 and 207). Again, the colors of the scale of colors are also the colors of the created image ("big rectangle"), since the scale of colors links the values of the time chart with the colors of the created image ("big rectangle").

In some embodiments, the user can zoom in and out this time chart in order to more clearly see the range of values of the gait characteristic measured during the activity; for example, some embodiments include a couple of rectangles ("−" and "+" in FIG. 14 (within the time chart)) which the user can press to minimize or zoom out ("−"), or to maximize or magnify or zoom in ("+"); by way of example without limitation, if the user touches "+", the range of values displayed by this time chart will be: from the top (346) to the middle (207); in other words, we will omit the lower half of the values, and magnify the upper half of the values; in some embodiments, the rectangles of the vertical scale of colors will adapt accordingly (e.g. the lower rectangles will not be displayed after pressing "+", and the upper rectangles will have increased their sizes); if the user touches the "+" again, the range of values displayed by this time chart will be: from the top (346) to the new middle ((346+207)/2); in other words, we will again omit the lower half of the currently displayed values, and magnify the upper half of the currently displayed values; and so on for a number of times (e.g. 3 times in some embodiments, although other embodiments may continue for more times, e.g. 7 or 10, or more); the zooming out, or minimizing, is achieved in the opposite way, by pressing "−". Other embodiments may use any other elements and/or approaches and/or any others and/or any variations and/or combinations thereof. Below this time chart, we can see a rectangular area at the bottom displaying data and/or metadata; by way of example without limitation, some embodiments may display the time-duration of the activity (e.g. in minutes), the number of steps taken, the distance travelled, and the total Calories burned during the activity; again, other embodiments may display any other data, and/or metadata, and/or elements and/or any others and/or any variations and/or combinations thereof.

Consequently, some embodiments may display the second set of the second amount of values representing colors as an image, or as a created image (e.g. a rectangular image, or a square image, or a trapezoidal image (please note that a square is a special case of a rectangle, which is a special case of a parallelogram, which is a special case of a trapezoid, so we can refer to the previously mentioned "big rectangle" regarding FIG. 14 as "trapezoidal image" throughout the whole of this disclosure)), together with a time chart (for example, the time chart shown in FIG. 14 below the "big rectangle", or "trapezoidal image").

Please note that in some embodiments, said time chart contains a line of points evolving in the time domain (e.g. the thick black line shown in FIG. 14 in said time chart, fluctuating from 67 to 346). Please also note that in some embodiments, each point of said thick black line in said time chart represents a result of an operation (e.g. a computation of a statistical parameter such as an average, and/or a mean, and/or a standard deviation, and/or any others and/or any combinations thereof) using a group of values from the first set of the first amount of values of the gait attribute; in other words, each point of said line of points in said time chart is determined using an operation that uses a group of values from the first set of the first amount. By way of example without limitation, the first point of said thick black line in said time chart may represent an average of e.g. the first 80 values from the first set of the first amount of values (representing measurements) of the gait attribute; the second point of said thick black line in said time chart may represent an average of e.g. the second 80 values from the first set of the first amount of values (representing measurements in the time domain) of the gait attribute; and so on (assuming for example that the first set of the first amount of values contains a number of values at least 80 times the number of points in the line of the time chart). In other embodiments, we may instead use values from the second set of the second amount of values resulting from the interpolation of the first set of the first amount of values; by way of example without limitation, if the interpolation from the first set into the second set results in obtaining 100 values for the second set from each 80 values of the first set, we may use use groups of 100 values from the second set to compute their average in order to obtain each one of the points of the line of the time chart; in other words, some embodiments may just substitute a group of e.g. 80 values from the first set of the first amount of values, by a group of e.g. 100 values from the second set of the second amount of values (e.g. assuming that the second set of the second amount of values results from interpolating each group of 80 values from the first set of the first amount of values into a group of 100 values). In other words, in some embodiments, the first point of said thick black line in said time chart may represent an average of e.g. the first 100 values from the second set of the second amount of values; the second point of said thick black line in said time chart may represent an average of e.g. the second 100 values from the second set of the second amount of values; and so on (assuming for example that the second set of the second amount of values contains a number of values at least 100 times the number of points in the line of the time chart); please note that in this case in which each point of said thick black line in said time chart represents a result of an operation (e.g. a computation of a statistical parameter such as an average, and/or a mean, and/or a standard deviation, and/or any others and/or any combinations thereof) using a group of values from the second set of the second amount of values, we are implicitly using a group of values from the first set of the first amount of values representing measurements of the gait attribute, because the values of the second set of the second amount have been obtained using the values from the first set of the first amount of values representing measurements of the gait attribute (e.g. using an interpolation); in this particular example of embodiment, we can say that each point of said thick black line in said time chart represents a result of an operation (in this example the operation may be a more complex operation, e.g. an operation comprising at least an interpolation (in order to obtain the values of the second set using values from the first set) and a computation of a statistical parameter such as an average, and/or a mean, and/or a standard deviation, and/or any others and/or any combinations thereof, being applied to values of the second set), but the operation still uses a group of values from the first set of the first amount of values of the gait attribute, at least implicitly, because the values from the first set have been used to obtain the values from the second set.

It is interesting to note that in some embodiments, by way of example without limitation, since there is a relationship between: the second set of the second amount of values representing colors displayed as a created image, and the first set of the first amount of values representing measurements of the gait characteristic, we can use a group of values from the second set of the second amount of values representing colors in order to compute each point of said thick black line in said time chart; for example, assuming that the image created using the "big rectangle" (or using the second set of the second amount of values representing colors) has 10000 pixels (e.g. 100 rows*100 columns), and assuming that the line of the time chart has 100 points, we can use the 100 elements of each one of the 100 rows of the "big rectangle" in order to compute each one of the 100 points of the line in the time chart; for example, we can use the 100 elements of the first row of the "big rectangle" (or "trapezoidal image") in order to retrieve the corresponding values representing measurements of the gait attribute from the first set of the first amount of values (e.g. simply reversing the process described above to obtain the elements of the "big rectangle" from the first set of the first amount of values), and compute the first point of the line of the time chart using the retrieved values (e.g. as their average); and we can use the 100 elements of the second row of the "big rectangle" (or of the second set of the second amount of values representing colors) in order to retrieve the corresponding values representing measurements of the gait attribute from the first set of the first amount of values, and compute the second point of the line of the time chart using the retrieved values (e.g. as their average); and so on; in other words, we are using a correspondence between groups of pixels in the image created using values from the second set of the second amount of values representing colors (from which the "big rectangle" is obtained), and points in the line of the time chart.

Consequently, in some embodiments we can create an image using a one-to-one correspondence between: the values from the second set of the second amount representing colors, and pixels of the image; and generate an interface that displays at least: the created image, and a time chart with a line of points, wherein each point of the line of points is determined using an operation that uses a group of values related to a group of values of the first set of the first amount. In one example, we can use a group of 80 values of the first set of the first amount (e.g. "first amount"=8000) of values representing measurements of the gait characteristic, and determine a point of the line of points of the time chart as the average of those 80 values; in this example, the group of values related to a group of values of the first set of the first amount, is said "group of values of the first set of the first amount" itself (the group of 80 values used); and in this example, the operation that uses the group of values comprises an average. In another example, we can use the first set of the first amount (e.g. "first amount"=8000) of values representing measurements of the gait characteristic, and perform an interpolation to generate a second set of a second amount (e.g. "second amount"=10000) of values related to the measurements of the gait characteristic; next, we can use a group of 100 values of the second set of the second amount (e.g. "second amount"=10000) of values related to measurements of the gait characteristic, and determine a point of the line of points of the time chart as the average of those 100 values; in this example, the group of values related to a group of values of the first set of the first amount, is said group of 100 values of the second set of the second amount (because implicitly, every group of 80 values of the first set of the first amount has been used to generate a group of 100 values of the second set of the second amount (through interpolation)); and in this example, the operation that uses the group of values comprises: an interpolation (to generate the values of the second set) and an average (of the values of the second set).

In some embodiments, in its simplest form, generating a user interface comprises displaying an image on the screen of the device; for example, displaying the created useful image previously mentioned. It is interesting to note that in some embodiments, the expression "generating an interface that displays an image", is equivalent to expressions comprising: generating a user interface that displays an image, or generating a display that comprises an image, or displaying an image, or other variations and/or combinations. For example, in some embodiments, generating an interface (or a user interface) that displays an image, comprises: displaying the image on a screen of a device (e.g. displaying the image on a screen of a device which may be running an application (e.g. a fitness application that uses the displayed image as an interface (or user interface) or within an interface (or user interface))). By way of example without limitation, an application (e.g. a fitness application, or a health application, or any other type of application) in a mobile or wearable device may generate an interface (or user interface) that displays an image for the user to see; in other words, the device may generate an interface (or user interface) of an application (e.g. a fitness application, or a health application, or any other type of application) in a screen of the device, wherein the interface displays an image; in other words, an interface (or user interface) of an application (e.g. a fitness application, or a health application, or any other type of application) may be generated in a screen of the device, wherein the interface displays an image; in other words, an application may display an image (e.g. on a screen of the device) for the user to see; in other words, an application may display an image for the user to see it; in other words, an image may be displayed for the user to see it; in other words, an image may be displayed; in other words, an image may be displayed on the mobile or wearable device carried by the user. These are all examples of equivalent expressions in some embodiments. It is interesting to note that in some embodiments, generating an interface (or user interface) that displays an image is equivalent to displaying an image; in some embodiments, the user may simply look at the image (which may be displayed on a screen of the mobile or wearable device, or in any other place), and in some embodiments the user may additionally interact with the displayed image (e.g. using touch sensitivity capabilities of a screen), or make some selection or decision (e.g. by touching some part of the screen, or by pressing some button, or in any other way) based on the displayed image. In some embodiments, the generated interface may comprise additional elements besides the image, and all (or some) of them may be displayed (e.g. on a screen of the device) for the user to interact with (e.g. touching an element (e.g. a button, or an icon, or a text written (or displayed) on the screen) displayed on a screen, or simply looking at it) some or all of them. Please note that throughout this whole disclosure (including this Specification and incorporated references), the term "gait attribute" and/or the term "gait characteristic" and/or the term "Cal/hour" may be substituted by: "Calories burned per time unit", and/or "Calories burned per hour", and/or "velocity", and/or "step length" (or stride length), and/or "frequency" (or step frequency), and/or "cadence", and/or any other information related to gait, and/or any variations and/or combinations thereof; the skilled artisan will also understand that adaptations may be needed to address the different terms, but those adaptations are obvious and/or well-known and/or easy-to-tackle making use of the incorporated references and/or any other well-known concepts in this area. Other embodiments may use any other elements and/or methodologies and/or technologies and/or any variations and/or combinations thereof.

Although the foregoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

The invention claimed is:

1. A method for generating an interface in a mobile or wearable device, the method comprising:
    determining, over a period of time, a first set of a first amount of values of a gait attribute;
    using an interpolation on the first set of the first amount of values to generate a second amount of numbers;
    obtaining, using said second amount of numbers, a second set of the second amount of values representing colors;
    creating an image composed of pixels, by assigning each one of the values representing colors to each one of the pixels of the image;
    generating the interface that displays at least the created image.

2. The method of claim 1, wherein the values of the gait attribute are determined with an update frequency greater than 3 Hz.

3. The method of claim 1, wherein the second amount is greater than 3000, and wherein the mobile or wearable device is a smartphone.

4. The method of claim 1, wherein the gait attribute is a length of a gait step.

5. The method of claim 1, wherein the obtaining the second set of the second amount of values representing colors comprises: determining a parameter related to the first set of the first amount of values, and using said parameter to compute each one of the values representing colors.

6. The method of claim 1, wherein the interface further displays additional metadata corresponding to the created image.

7. A method for generating an interface in a mobile or wearable device, the method comprising:
    determining, over a period of time, a first set of a first amount of values of a gait attribute;
    using an interpolation on the first set of the first amount of values to generate a second amount of numbers;
    leveraging a matrix factorization on the second amount of numbers to generate and store a third amount of numbers;
    retrieving from the stored third amount of numbers, an approximation of the second amount of numbers;
    obtaining, using said approximation of the second amount of numbers, a second set of the second amount of values representing colors;
    creating an image composed of pixels, by assigning each one of the values representing colors to each one of the pixels of the image;
    generating the interface that displays at least the created image.

8. The method of claim 7, wherein the values of the gait attribute are determined with an update frequency greater than 3 Hz.

9. The method of claim 7, wherein the second amount is greater than 3000, and wherein the mobile or wearable device is a smartphone.

10. The method of claim 7, wherein the gait attribute is a length of a gait step.

11. The method of claim 7, wherein the obtaining the second set of the second amount of values representing colors comprises: determining a parameter related to the first set of the first amount of values, and using said parameter to compute each one of the values representing colors.

12. The method of claim 7, wherein the interface further displays additional metadata corresponding to the created image.

13. The method of claim 7, wherein the matrix factorization comprises a singular value decomposition.

14. The method of claim 1, wherein the values of the gait attribute are determined with an update frequency greater than 3 Hz;
    wherein the second amount is greater than 3000;
    wherein the mobile or wearable device is a smartphone;
    wherein the gait attribute is a length of a gait step;

wherein the obtaining the second set of the second amount of values representing colors comprises: determining a parameter related to the first set of the first amount of values, and using said parameter to compute each one of the values representing colors; and wherein the interface further displays additional metadata corresponding to the created image.

15. The method of claim 7, wherein the values of the gait attribute are determined with an update frequency greater than 3 Hz;

wherein the second amount is greater than 3000, and wherein the mobile or wearable device is a smartphone;

wherein the gait attribute is a length of a gait step;

wherein the obtaining the second set of the second amount of values representing colors comprises: determining a parameter related to the first set of the first amount of values, and using said parameter to compute each one of the values representing colors;

wherein the interface further displays additional metadata corresponding to the created image; and wherein the matrix factorization comprises a singular value decomposition.

16. A system comprising:

a processor;

a processor-readable medium including instructions which, when executed by the processor, cause the processor, for generating an interface in a mobile or wearable device, to perform functions comprising:

determining, over a period of time, a first set of a first amount of values of a gait attribute;

using an interpolation on the first set of the first amount of values to generate a second amount of numbers;

obtaining, using said second amount of numbers, a second set of the second amount of values representing colors;

creating an image composed of pixels, by assigning each one of the values representing colors to each one of the pixels of the image;

generating the interface that displays at least the created image.

17. The system of claim 16, wherein the obtaining the second set of the second amount of values representing colors comprises: determining a parameter related to the first set of the first amount of values, and using said parameter to compute each one of the values representing colors.

18. The system of claim 16, wherein the values of the gait attribute are determined with an update frequency greater than 3 Hz;

wherein the second amount is greater than 3000;

wherein the mobile or wearable device is a smartphone;

wherein the gait attribute is a length of a gait step;

wherein the obtaining the second set of the second amount of values representing colors comprises: determining a parameter related to the first set of the first amount of values, and using said parameter to compute each one of the values representing colors; and wherein the interface further displays additional metadata corresponding to the created image.

19. A system comprising:

a processor;

a processor-readable medium including instructions which, when executed by the processor, cause the processor, for generating an interface in a mobile or wearable device, to perform functions comprising:

determining, over a period of time, a first set of a first amount of values of a gait attribute;

using an interpolation on the first set of the first amount of values to generate a second amount of numbers;

leveraging a matrix factorization on the second amount of numbers to generate and store a third amount of numbers;

retrieving from the stored third amount of numbers, an approximation of the second amount of numbers;

obtaining, using said approximation of the second amount of numbers, a second set of the second amount of values representing colors;

creating an image composed of pixels, by assigning each one of the values representing colors to each one of the pixels of the image;

generating the interface that displays at least the created image.

20. The system of claim 19, wherein the values of the gait attribute are determined with an update frequency greater than 3 Hz;

wherein the second amount is greater than 3000;

wherein the mobile or wearable device is a smartphone;

wherein the gait attribute is a length of a gait step;

wherein the obtaining the second set of the second amount of values representing colors comprises: determining a parameter related to the first set of the first amount of values, and using said parameter to compute each one of the values representing colors; and wherein the interface further displays additional metadata corresponding to the created image.

* * * * *